(12) United States Patent
Purohit et al.

(10) Patent No.: US 11,241,509 B2
(45) Date of Patent: Feb. 8, 2022

(54) LIGANDS FOR IMAGING CARDIAC INNERVATION

(71) Applicant: Lantheus Medical Imaging, Inc., North Billerica, MA (US)

(72) Inventors: Ajay Purohit, Sudbury, MA (US); Thomas D. Harris, Salem, NH (US); Heike S. Radeke, South Grafton, MA (US); Simon P. Robinson, Stow, MA (US); Ming Yu, Chelmsford, MA (US); David S. Casebier, Carlisle, MA (US); Michael T. Azure, Renlop, AL (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

(21) Appl. No.: 15/986,680

(22) Filed: May 22, 2018

(65) Prior Publication Data

US 2018/0339070 A1 Nov. 29, 2018

Related U.S. Application Data

(63) Continuation of application No. 13/916,205, filed on Jun. 12, 2013, now Pat. No. 10,010,631, which is a continuation of application No. 12/448,575, filed as application No. PCT/US2007/088500 on Dec. 21, 2007, now Pat. No. 8,491,868.

(60) Provisional application No. 60/877,211, filed on Dec. 26, 2006.

(51) Int. Cl.
| | |
|---|---|
| A61K 51/04 | (2006.01) |
| C07C 217/70 | (2006.01) |
| C07B 59/00 | (2006.01) |
| C07C 215/60 | (2006.01) |
| C07C 279/06 | (2006.01) |
| C07C 279/08 | (2006.01) |

(52) U.S. Cl.
CPC .......... *A61K 51/04* (2013.01); *A61K 51/0453* (2013.01); *A61K 51/0459* (2013.01); *C07B 59/001* (2013.01); *C07C 215/60* (2013.01); *C07C 217/70* (2013.01); *C07C 279/06* (2013.01); *C07C 279/08* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 4,094,881 A | 6/1978 | Berges | |
| 4,258,188 A * | 3/1981 | Bagli | C07D 307/24 544/139 |
| 4,270,537 A | 6/1981 | Romaine | |
| 4,275,074 A | 6/1981 | Langham | |
| 4,596,556 A | 6/1986 | Morrow et al. | |
| 4,622,217 A | 11/1986 | Wieland | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |

(Continued)

FOREIGN PATENT DOCUMENTS

| | | |
|---|---|---|
| CN | 101555232 A | 10/2009 |
| EP | 1 749 815 A1 | 2/2007 |

(Continued)

OTHER PUBLICATIONS

Parcal et al. European Journal of Medicinal Chemistry (1990), 25(1), 81-5.*
Zhou et al. Hejishu (1985), (9), 31-2.*
Hanson et al. Journal of Heterocyclic Chemistry (1985), 22(1), 47-8.*
Thornber, Chem. Soc. Rev.,1979, 563-580.*
Extended European Search Report for EP 12152815.2 dated Jun. 20, 2012.
Extended European Search Report for EP 12152816.0 dated Jun. 20, 2012.
Extended European Search Report for EP 12152817.8 dated Jun. 22, 2012.
Extended European Search Report for EP 12152818.6 dated Jun. 22, 2012.
Invitation to Pay Additional Fees for PCT/US2007/088500 dated Dec. 19, 2008.

(Continued)

*Primary Examiner* — Ana Z Muresan
(74) *Attorney, Agent, or Firm* — Wolf, Greenfield & Sacks, P.C.

(57) ABSTRACT

Novel compounds that find use as imaging agents within nuclear medicine applications (PET imaging) for imaging of cardiac innervation are disclosed. These PET based radiotracers may exhibit increased stability, decreased NE release thereby reducing side effects, improved quantitative data, and/or high affinity for VMAT over prior radiotracers. In some instances the compounds are developed by derivatizing certain compounds with 18F in a variety of positions: aryl, alkyl, a keto, benzylic, beta-alkylethers, gamma-propylalkylethers and beta-proplylalkylethers. Alternatively or additionally, a methyl group a is added to the amine, and/or the catechol functionality is either eliminated or masked as a way of making these compounds more stable.

4 Claims, 2 Drawing Sheets

(56) References Cited

U.S. PATENT DOCUMENTS

| | | | |
|---|---|---|---|
| 5,649,912 A | | 7/1997 | Peterson |
| 5,650,411 A | * | 7/1997 | Heeres .............. A61K 31/445 514/63 |
| 5,674,863 A | * | 10/1997 | Blackburn ........... C07D 223/16 514/150 |
| 5,704,911 A | | 1/1998 | Parsons |
| 5,874,573 A | | 2/1999 | Winchell et al. |
| 5,879,657 A | | 3/1999 | DeGrado et al. |
| 5,893,397 A | | 4/1999 | Peterson et al. |
| 5,993,412 A | | 11/1999 | Deily et al. |
| 6,511,648 B2 | | 1/2003 | Harris et al. |
| 8,491,868 B2 | | 7/2013 | Purohit et al. |
| 8,653,282 B2 | | 2/2014 | Frutos et al. |
| 9,388,125 B2 | | 7/2016 | Purohit et al. |
| 9,550,000 B2 | | 1/2017 | Radeke et al. |
| 9,682,927 B2 | | 6/2017 | Purohit et al. |
| 10,010,631 B2 | | 7/2018 | Purohit et al. |
| 2004/0018162 A1 | | 1/2004 | Bimczok et al. |
| 2006/0127309 A1 | | 6/2006 | Raffel et al. |
| 2010/0221182 A1 | | 9/2010 | Purohit et al. |
| 2013/0149244 A1 | | 6/2013 | Purohit et al. |
| 2014/0030189 A1 | | 1/2014 | Purohit et al. |
| 2014/0328756 A1 | | 11/2014 | Cesati et al. |
| 2016/0362362 A1 | | 12/2016 | Purohit et al. |
| 2017/0266326 A1 | | 9/2017 | Radeke et al. |
| 2017/0355669 A1 | | 12/2017 | Purohit et al. |

FOREIGN PATENT DOCUMENTS

| | | |
|---|---|---|
| EP | 2 671 575 A1 | 12/2013 |
| FR | 2 343 732 A1 | 10/1977 |
| GB | 672 048 A | 5/1952 |
| GB | 1 215 255 A | 12/1970 |
| JP | 3-023203 A | 1/1991 |
| JP | 2017-131851 A | 8/2017 |
| WO | WO 97/13537 A1 | 4/1997 |
| WO | WO 97/37705 A1 | 10/1997 |
| WO | WO 98/23565 A2 | 6/1998 |
| WO | WO 99/18053 A1 | 4/1999 |
| WO | WO 99/34850 A1 | 7/1999 |
| WO | WO 99/52861 A1 | 10/1999 |
| WO | WO 00/09115 A1 | 2/2000 |
| WO | WO 01/060416 A2 | 8/2001 |
| WO | WO 02/11715 A2 | 2/2002 |
| WO | WO 2004/037166 A2 | 5/2004 |
| WO | WO 2005/009479 A1 | 2/2005 |
| WO | WO 2005/053615 A2 | 6/2005 |
| WO | WO 2005/079391 A2 | 9/2005 |
| WO | WO 2005/095345 A2 | 10/2005 |
| WO | WO 2005/115971 A1 | 12/2005 |
| WO | WO 2006/032705 A2 | 3/2006 |
| WO | WO 2006/044280 A1 | 4/2006 |
| WO | WO 2006/136846 A1 | 12/2006 |
| WO | WO 2008/071574 A1 | 6/2008 |
| WO | WO 2008/075040 A2 | 6/2008 |
| WO | WO 2008/082305 A1 | 7/2008 |
| WO | WO 2008/083056 A2 | 7/2008 |
| WO | WO 2008/115593 A1 | 9/2008 |
| WO | WO 2010/015387 A1 | 2/2010 |
| WO | WO 2010/115881 A1 | 10/2010 |
| WO | WO 2010/120368 A2 | 10/2010 |
| WO | WO 2011/005322 A2 | 1/2011 |
| WO | WO 2011/097649 A2 | 8/2011 |
| WO | WO 2011/143360 A2 | 11/2011 |
| WO | WO 2013/036869 A2 | 3/2013 |

OTHER PUBLICATIONS

International Search Report and Written Opinion for PCT/US2007/088500 dated Mar. 13, 2009.
International Preliminary Report on Patentability for PCT/US2007/088500 dated Jul. 9, 2009.
Partial Supplementary European Search Report for EP 11781241.2 dated Jul. 1, 2015.
International Search Report and Written Opinion for PCT/US2011/036142 dated Dec. 22, 2011.
International Preliminary Report on Patentability for PCT/ US2011/036142 dated Nov. 22, 2012.
Extended European Search Report for EP 12829763.7 dated Jun. 22, 2015.
International Search Report and Written Opinion for PCT/US2012/054309 dated Feb. 27, 2013.
International Preliminary Report on Patentability for PCT/US2012/054309 dated Mar. 20, 2014.
[No Author Listed] "Pharmaceutical Salts." May 1, 1958. p. 334-45. Retrieved on Aug. 26, 2014 from http://phoenix.tuwien.ac.at/pdf/pharmaceutical_salts/Pharmaceutical_salts.pdf.
[No Author Listed] Hejishu. 1985:9;31-2.
[No Author Listed] Zonghua Heyixue Zazhi. Chinese J Nucl Med. 1984 4(3) 157-9.
Adams et al., Nucleophilic routes to selectively fluorinated aromatics. Chem Soc Rev. 1999;28:225-31.
Adams et al., The formation of 4,4'-difluorobenzophenone from 4,4'-dinitrodiphenylmethane. J Fluorine Chem. 1998;92:127-129.
Akgun et al., N1'-(p-[18F]Fluorobenzyl)naltrindole (p-[18F]BNTI) as a potential PET imaging agent for DOP receptors. J Labelled Comp Radiopharm. 2006;49:857-866.
Amartey et al., An efficient batch preparation of high specific activity. Appl Radiat Isot. May 2001;54(5):711-4.
Anbarasan et al., Efficient synthesis of aryl fluorides. Angew Chem Int Ed Engl. Mar. 15, 2010;49(12):2219-22.
Angelini et al., Nucleophilic aromatic substitution of activated cationic groups by 18F-labeled Fluoride. A useful route to no-carrier-added (NCA) 18F-labeled aryl fluorides.. J Fluorine Chem. 1985;27:177-91.
Armour, Myocardial ischaemia and the cardiac nervous system. Cardiovasc Res. 1998;41:41-54.
Badiang et al., One-Step Conversion of Aldehydes to Oxazolines and 5,6-Dihydroxy-4 H-1,3-oxazines Using 1,2- and 1,3-Azido Alcohols. J Org Chem. 1996;61:2484-87.
Barlin et al., Useful preparations involving the reactions of nucleophiles with some trimethylammonio-derivatives of nitrogen heterocycles.. J Chem Soc., Perkin Trans 1. 1972:1269-72.
Bax et al., [123]I-mIBG scintigraphy to predict inducibility of ventricular arrhythmias on cardiac electrophysiology testing: a prospective multicenter pilot study. Circ Cardiovasc Imaging. Sep. 2008;1(2):131-40. Epub Jul. 30, 2008.
Beletskaya et al., Catalytic sandmeyer bromination. Synthesis. 2007; (No. 16):2534-38.
Bengel et al., Assessment of cardiac sympathetic neuronal function using PET imaging. J Nucl Cardiol. Sep.-Oct. 2004;11(5):603-16.
Berge et al., Pharmaceutical salts. J Pharm Sci. Jan. 1977;66(1):1-19.
Beringer et al., Diaryliodonium Salts. II. The Phenylation of Organic and Inorganic Bases. J. Am. Chem. Soc. 1953;75(11):2708-2712.
Berry et al., Para-[18F]fluorobenzylguanidine kinetics in a canine coronary artery occlusion model. J Nucl Cardiol. Mar.-Apr. 1996;3(2):119-29.
Berry et al., Uptake and retention kinetics of para-fluorine-18-fluorobenzylguanidine in isolated rat heart. J Nucl Med. Dec. 1996;37(12):2011-6.
Böhm et al., Evidence for reduction of norepinephrine uptake sites in the failing human heart. J Am Coll Cardiol. Jan. 1995;25(1):146-53.
Bolster et al., Synthesis of DL-[1-11C]methionine. Int J Rad Appl Instrum A. 1986;37(10):1069-70.
Boogers et al., Cardiac sympathetic denervation assessed with 123-iodine metaiodobenzylguanidine imaging predicts ventricular arrhythmias in implantable cardioverterdefibrillator patients. J Am Coll Cardiol. Jun. 15, 2010;55(24):2769-77.
Bozek et al., 18F PET imaging of cardiac sympathetic denervation with LMI1195, a new neuronal imaging agent. J Nucl Med. 2010;51(S2):1701.

(56) References Cited

OTHER PUBLICATIONS

Bozek et al., Abstract 570: Heart Failure Imaging in the Rat with LMI1195: A New PET Cardiac Neuronal Imaging Agent. AHA Scientific Session 2009. Orlando, FL. Nov. 15-17, 2009. Circulation. 2009;120:S362.

Broekema et al., Synthesis of leukotriene B4 antagonists labeled with In-111 or Tc-99m to image infectious and inflammatory foci. J Med Chem. Oct. 6, 2005;48(20):6442-53.

Bryce et al., Electrophilic fluorination of aryltrialkyltin derivatives with caesium fluoroxysulphate. J Chem Soc., Chem Commun. 1986:1623-4.

Buck et al., Specific uptake of m-[125I]iodobenzylguanidine in the human neuroblastoma cell line SK-N-SH. Cancer Res. Dec. 1985;45(12 Pt 1):6366-70.

Calkins et al., Correlation between scintigraphic evidence of regional sympathetic neuronal dysfunction and ventricular refractoriness in the human heart. Circulation. Jul. 1993;88(1):172-9.

Carrío, Cardiac neurotransmission imaging. J Nucl Med. Jul. 2001;42(7):1062-76.

Castanet et al., Mild and regioselective iodination of electron-rich aromatics with N-iodosuccinimide and catalytic trifluoroacetic acid. Tetrahedron Lett. 2002;43:5047-48.

Cazorla et al., Metal-free electrophilic fluorination of alkyl trifluoroborates and boronic acids. Tetrahedron Lett. 2009;50:3936-8.

Chen et al., New perspectives on the role of autonomic nervous system in the genesis of arrhythmias. J Cardiovasc Electrophysiol. Jan. 2007;18(1):123-7. Epub Aug. 14, 2006.

Comar et al., Labelling and metabolism of methionine-methyl-11 C. Eur J Nucl Med. 1976;1(1):11-4.

Dae et al., Heterogeneous sympathetic innervation in German shepherd dogs with inherited ventricular arrhythmia and sudden cardiac death. Circulation. Aug. 19, 1997;96(4):1337-42.

Dahmen et al., A novel solid-phase synthesis of highly diverse guanidines: reactions of primary amines attached to the T2 linker. Org Lett. Nov. 16, 2000;2(23):3563-5.

Daly et al., The chemorelease of norepinephrine from mouse hearts. Structure-activity relationships. I. Sympathomimetic and related amines. J Med Chem. May 1966;9(3):273-80.

Degrado et al., Myocardial kinetics of carbon-11-meta-hydroxyephedrine: retention mechanisms and effects of norepinephrine. J Nucl Med. Aug. 1993;34(8):1287-93.

Degrado et al., Uptake mechanisms of meta-[123I]iodobenzylguanidine in isolated rat heart. Nucl Med Biol. Jan. 1995;22(1):1-12.

Ding et al., Synthesis of high specific activity (+)- and (−)-6-[18F]fluoronorepinephrine via the nucleophilic aromatic substitution reaction. J Med Chem. Feb. 1991;34(2):767-71.

Ding et al., Synthesis of high specific activity 6-[18F]fluorodopamine for positron emission tomography studies of sympathetic nervous tissue. J Med Chem. Feb. 1991;34(2):861-3.

Ermert et al., Comparison of pathways to the versatile synthon of no-carrier-added 1-bromo-4-[18F]fluorobenzene. J Labelled Comp Radiopharm. 2004;47:429-41.

Esler et al., The 2009 Carl Ludwig Lecture: Pathophysiology of the human sympathetic nervous system in cardiovascular diseases: the transition from mechanisms to medical management. J Appl Physiol. Feb. 2010;108(2):227-37. Epub Nov. 25, 2009.

Estep et al., Indole Resin: A Versatile New Support for the Solid-Phase Synthesis of Organic Molecules. J Org Chem. 1998;63(16):5300-1.

Ewing, Diabetic autonomic neuropathy and the heart. Diabetes Res Clin Pract. Feb. 1996;30 Suppl:S31-6.

Farde et al., Positron emission tomography shows high specific uptake of racemic carbon-11 labelled norepinephrine in the primate heart. Eur J Nucl Med. Apr. 1994;21(4):345-7.

Filimonov et al., Unusually stable, versatile, and pure arenediazonium tosylates: their preparation, structures, and synthetic applicability. Org Lett. Sep. 18, 2008;10(18):3961-4. Epub Aug. 23, 2008.

Fowler et al., Radiopharmaceuticals. 12. A new rapid synthesis of carbon-11 labeled norepinephrine hydrochloride. J Med Chem. Feb. 1974;17(2):246-8.

Fowler et al., Synthesis and preliminary evaluation in animals of carrier-free 11C-1-dopamine hydrochloride: X. J Nucl Med. Nov. 1973;14(11):867-9.

Furuya et al., Carbon-Fluorine Bond Formation for the Synthesis of Aryl Fluorides. Synthesis (Stuttg). Jun. 1, 2010;2010(11):1804-1821.

Furuya et al., Fluorination of boronic acids mediated by silver(I) triflate. Org Lett. Jul. 2, 2009;11(13):2860-3.

Furuya et al., Palladium-mediated fluorination of arylboronic acids. Angew Chem Int Ed Engl. 2008;47(32):5993-6.

Furuya et al., Silver-mediated fluorination of functionalized aryl stannanes. J Am Chem Soc. Feb. 11, 2009;131(5):1662-3.

Galea et al., Synthesis of [$^{76}$Br]RPR 104632 for in Vivo Studies of the NMDA Receptor Channel Complex. J Labelled Comp Radiopharm. 1997;40:608-610. BIOSIS Abstract Accession No. PREV199800109838.

Ganguly et al., Ecofriendly iodination of activated aromatics and coumarins using potassium iodide and ammonium peroxodisulfate.. Synthesis. 2010;(9):1467-72.

Ganguly et al., Mild regioselective monobromination of activated aromatics and heteroaromatics with N-bromosuccinimide in tetrabutylammonium bromide.. Synthesis. 2005;(7):1103-08.

Garg et al., Synthesis and preliminary evaluation of para- and meta-[18F]fluorobenzylguanidine. Nucl Med Biol. Jan. 1994;21(1):97-103.

Glowniak et al., Evaluation of metaiodobenzylguanidine heart and lung extraction fraction by first-pass analysis in pigs. J Nucl Med. May 1992;33(5):716-23.

Grushin et al., Fluorination of Nonactivated Haloarenes via Arynes under Mild Conditions, Resulting from Further Studies toward Ar-F Reductive Elimination from Palladium(II). Organometallics. 2008;27(19):4825-4828.

Hanson et al., Radioiodinated 1-carboxamidino-4-phenylpiperazine: a potential adrenal and myocardial imaging radiopharmaceutical. Int J Appl Radiat Isot. Aug. 1982;33(8):629-32.

Henneman et al., Cardiac neuronal imaging: application in the evaluation of cardiac disease. J Nucl Cardiol. May-Jun. 2008;15(3):442-55. Epub Apr. 16, 2008.

Hilliard et al., Multiple Mechanisms of Action for Inhibitors of Histidine Protein Kinases from Bacterial Two-Component Systems. Antimicrob Agents Chemother. 1999;43:1693-99.

Högberg et al., Bioisosteric modification of PETT-HIV-1 RT-inhibitors: synthesis and biological evaluation. Bioorg Med Chem Lett. Feb. 7, 2000;10(3):265-8.

Horwitz et al., Some 6-substituted uracils. J Org Chem. 1961;26:3392-5.

Hubbard et al., Halo- and azidodediazoniation of arenediazonium tetrafluoroborates with trimethylsilyl halides and trimethylsilyl azide and sandmeyer-type bromodediazoniation with Cu(I)Br in [BMIM][PF6] ionic liquid. J Org Chem. Jan. 4, 2008;73(1):316-9. Epub Dec. 8, 2007.

Iskra et al., Nonmetal-catalyzed iodination of arenes with iodide and hydrogen peroxide. Synthesis. 2004;(11):1869-73.

Jacobson et al., Myocardial iodine-123 meta-iodobenzylguanidine imaging and cardiac events in heart failure. Results of the prospective ADMIRE-HF (AdreView Myocardial Imaging for Risk Evaluation in Heart Failure) study. J Am Coll Cardiol. May 18, 2010;55(20):2212-21. Epub Feb. 25, 2010.

Jang et al., 4-[18F]Fluoro-m-hydroxyphenethylguanidine: a radiopharmaceutical for quantifying regional cardiac sympathetic nerve density with positron emission tomography. J Med Chem. Sep. 26, 2013;56(18):7312-23. doi: 10.1021/jm400770g. Epub Sep. 5, 2013.

Jang et al., Synthesis and bioevaluation of [(18)F]4-fluoro-m-hydroxyphenethylguanidine ([(18)F]4F-MHPG): a novel radiotracer for quantitative PET studies of cardiac sympathetic innervation. Bioorg Med Chem Lett. Mar. 15, 2013;23(6):1612-6. doi: 10.1016/j.bmcl.2013.01.106.

Kabalka et al., Synthesis of organic bromides via organotrifluoroborates. Organometallics. 2004;23:4519-21.

(56) References Cited

OTHER PUBLICATIONS

Keen et al., In vivo cerebral protein synthesis rates with leucyl-transfer RNA used as a precursor pool: determination of biochemical parameters to structure tracer kinetic models for positron emission tomography. J Cereb Blood Flow Metab. Aug. 1989;9(4):429-45.
Kim et al., Evaluation of m-([18F]fluoropropyl)benzylguanidine ([18F]FPBG) for myocardial imaging in rat. J Nucl Med. 2009; 50 (Supplement 2):1940.
Kim et al., Expanding the substrate scope for C—H amination reactions: oxidative cyclization of urea and guanidine derivatives. Org Lett. Mar. 1, 2006;8(6):1073-6.
Klapars et al., Copper-catalyzed halogen exchange in aryl halides: an aromatic Finkelstein reaction. J Am Chem Soc. Dec. 18, 2002;124(50):14844-5.
Ko et al., Effects of anesthetic agents on cellular 123I-MIBG transport and in vivo 123I-MIBG biodistribution. Eur J Nucl Med Mol Imaging. Mar. 2008;35(3):554-61. Epub Oct. 13, 2007.
Krasikova et al., Asymmetric synthesis of 6-[18F]Fluoro-L-DOPA using a chiral nickel complex of the Schiff base of (S)-o-[(N-benzylprolyl)-amino]benzophenone and glycine. J Labelled Comp Radiopharm. 1999;42:S102-S104.
Krasnokutskaya et al., A new, one-step, effective protocol for the iodination of aromatic and heterocyclic compounds via aprotic diazotization of amines. Synthesis. 2007;(1):81-84.
Kraszkiewicz et al., Oxidative iodination of deactivated arenes in concentrated sulfuric acid with I2/NaIO4 Iodinating Systems. Synthesis. 2006;(7):1195-99.
Kumar eta l., Bromination of aromatic compounds using ammonium bromide and oxone. Synthesis. 2010;(10):1629-32.
Lamoy et al., Cardiac imaging and uptake mechanism of 18F LMI1195, a novel PET cardiac neuronal imaging agent. J Nucl Med 51 (S2) 2010. Abstract 262.
Langer et al., High specific radioactivity (1R,2S)-4-[(18)F]fluorometaraminol: a PET radiotracer for mapping sympathetic nerves of the heart. Nucl Med Biol. Apr. 2000;27(3):233-8.
Langer et al., PET and SPET tracers for mapping the cardiac nervous system. Eur J Nucl Med Mol Imaging. Mar. 2002;29(3):416-34.
Lazewatsky et al., Radiation dosimetry of LMI1195, first-in-human study of a novel F-18 labeled tracer for imaging myocardial innervation.. J Nucl Med. 2010;51(S2):1432.
Lee et al., New potential and practical MIBG analogs for PET: meta-(3-(18F)fluoroalkyl)benzylguanidines'. J Labelled Comp Radiopharm. 2001;44:S404-S406.
Lee et al., Potential and practical adrenomedullary PET radiopharmaceuticals as an alternative to m-iodobenzylguanidine: m-(omega-[18F]fluoroalkyl)benzylguanidines. Bioconjug Chem. Jan.-Feb. 2004;15(1):104-11.
Lee, Syntheses and Development of Novel PET and SPECT Radiotracers for Adrenomedullar, Fatty acid metabolism, and Tumor Imaging. Thesis. Dspace at INHA University. College of Natural Science. 2004. 109 pages.
Lenz et al., Dofetilide, a new class III antiarrhythmic agent. Pharmacotherapy. Jul. 2000;20(7):776-86.
Lepore et al., Recent advances in heterolytic nucleofugal leaving groups. Tetrahedron. Jun. 11, 2007;63(24):5103-5122.
Liang et al., Decreased adrenergic neuronal uptake activity in experimental right heart failure. A chamber-specific contributor to beta-adrenoceptor downregulation. J Clin Invest. Oct. 1989;84(4):1267-75.
Loc'H et al., Preparation and pharmacological characterization of [76Br]-meta-bromobenzylguanidine ([76Br]MBBG). Nucl Med Biol. Jan. 1994;21(1):49-55.
Lothian et al., Rapid fluorodesilylation of aryltrimethylsilanes using xenon difluoride: an efficient new route to aromatic fluorides. Synlett. Oct. 1993:753-5.
Lulinski et al., Eco-friendly oxidative iodination of various arenes with a urea-hydrogen peroxide adduct (UHP) as the oxidant. Synthesis. 2004; (3):441-45.

Maddahi et al., Phase I, first-in-human study of BMS747158, a novel 18F-labeled tracer for myocardial perfusion PET: dosimetry, biodistribution, safety, and imaging characteristics after a single injection at rest. J Nucl Med. Sep. 2011;52(9):1490-8. Epub Aug. 17, 2011.
Martinez-Barrasa et al., Pyridinium N-(2'-Azinyl)Aminides: Regioselective Synthesis of 2-Alkylaminoazines. Tetrahedron. 2000;56:2481-90.
Matsunari et al., Iodine-123 metaiodobenzylguanidine imaging and carbon-11 hydroxyephedrine positron emission tomography compared in patients with left ventricular dysfunction. Circ Cardiovasc Imaging. Sep. 2010;3(5):595-603. Epub Jun. 9, 2010.
Matsunari et al., Phantom studies for estimation of defect size on cardiac (18)F Spect and PET: implications for myocardial viability assessment. J Nucl Med. Oct. 2001;42(10):1579-85.
Menzel et al., An improved method for the bromination of metalated haloarenes via lithium, zinc transmetalation: a convenient synthesis of 1,2-dibromoarenes. J Org Chem. Mar. 3, 2006;71(5):2188-91.
Minardo et al., Scintigraphic and electrophysiological evidence of canine myocardial sympathetic denervation and reinnervation produced by myocardial infarction or phenol application. Circulation. Oct. 1988;78(4):1008-19.
Mistry et al., Dosimetry in nonhuman primates of [18F]LMI1195, a novel PET tracer for imaging the cardiac sympathetic nervous system. J Nucl Med 51 (S2)2010. Abstract 1447.
Mitani et al., $^{123}$I-MIBG myocardial imaging in hypertensive patients: abnormality progresses with left ventricular hypertrophy. Ann Nucl Med. Aug. 1996;10(3):315-21.
Mitrani et al., Regional cardiac sympathetic denervation in patients with ventricular tachycardia in the absence of coronary artery disease. J Am Coll Cardiol. Nov. 1, 1993;22(5):1344-53.
Münch et al., Cardiac overexpression of the norepinephrine transporter uptake-1 results in marked improvement of heart failure. Circ Res. Oct. 28, 2005;97(9):928-36. Epub Sep. 15, 2005.
Münch et al., Evaluation of sympathetic nerve terminals with [(11)C]epinephrine and [(11)C]hydroxyephedrine and positron emission tomography. Circulation. Feb. 8, 2000;101(5):516-23.
Murphy et al., Meta halogenation of 1,3-disubstituted arenes via iridium-catalyzed arene borylation. J Am Chem Soc. Dec. 19, 2007;129(50):15434-5. Epub Nov. 21, 2007.
Nakajo et al., Iodine-131 metaiodobenzylguanidine intra- and extravesicular accumulation in the rat heart. J Nucl Med. Jan. 1986;27(1):84-9.
Namavari et al., Regioselective radiofluorodestannylation with [$^{18}$F]F$_2$ and [$^{18}$F]CH$_3$COOF: a high yield synthesis of 6-[$^{18}$F]Fluoro-L-dopa. Int J Rad Appl Instrum A. Aug. 1992;43(8):989-96.
Nattel, The molecular and ionic specificity of antiarrhythmic drug actions. J Cardiovasc Electrophysiol. Feb. 1999;10(2):272-82.
Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.
Netscher, Sulfonate leaving groups for nucleophilic substitution reactions—improved structures and procedures. Recent Res Dev Org Chem. 2003;7:71-83.
Odaka et al., Reappearance of cardiac presynaptic sympathetic nerve terminals in the transplanted heart: correlation between PET using (11)C-hydroxyephedrine and invasively measured norepinephrine release. J Nucl Med. Jul. 2001;42(7):1011-6.
Ozawa et al., Pharmacological properties of heterocyclic amidine derivatives. II. Pharmacological studies of phenylguanylpiperazine derivatives. Chem Pharm Bull (Tokyo). Dec. 1968;16(12):2482-7.
Packer, The neurohormonal hypothesis: a theory to explain the mechanism of disease progression in heart failure. J Am Coll Cardiol. Jul. 1992;20(1):248-54.
Paik et al., Validation of $^{18}$F Fluoropropyl-benzylguanidine as a novel positron emitting analogue of MIBG. J Nucl Med. 2002;43:363P. No. 1460.
Paixao et al., 1,3-Diphenylguanidinium Trifluoroacetate. Acta Cryst. 1998;C54:1484-6.
Pauwels et al., Fluorine-18-radiolabeled pharmaceuticals for imaging with positron emission tomography, excluding [18F]-fluorodeoxyglucose. Drugs of the Future. 2002;27:655-67.

(56) References Cited

OTHER PUBLICATIONS

Pietilä et al., Reduced myocardial carbon-11 hydroxyephedrine retention is associated with poor prognosis in chronic heart failure. Eur J Nucl Med. Mar. 2001;28(3):373-6.

Pike et al., Reactions of cyclotron-produced [18F]fluoride with diaryliodonium salts—a novel single-step route to no-carrier-added [18] fluoroarenes. J Chem Soc., Chem Commun. 1995:2215-6.

Podrid et al., Role of the sympathetic nervous system in the genesis of ventricular arrhythmia. Circulation. Aug. 1990;82(2 Suppl):I103-13.

Prakash et al., N-halosuccinimide/BF3-H2O, efficient electrophilic halogenating systems for aromatics. J Am Chem Soc. Dec. 8, 2004;126(48):15770-6.

Qin et al., Iodine-Mediated Guanidine Formation through Arylsulfonyl-Activated Thioureas. Synlett. 2009. Advanced Online Publication. 4 pages.

Raffel et al., Assessment of cardiac sympathetic nerve integrity with positron emission tomography. Nucl Med Biol. Jul. 2001;28(5):541-59.

Raffel et al., Influence of Vesicular Storage and Monoamine Oxidase Activity on [$^{11}$C]Phenylephrine Kinetics: Studies in Isolated Rat Heart. J Nucl Med. 1990;40:323-30.

Raffel et al., Radiolabeled phenethylguanidines: novel imaging agents for cardiac sympathetic neurons and adrenergic tumors. J Med Chem. May 3, 2007;50(9):2078-88. Epub Apr. 10, 2007.

Rajesh et al., Bromination of deactivated aromatics: a simple and efficient method. J Org Chem. Jul. 20, 2007;72(15):5867-9. Epub Jun. 23, 2007.

Reifenrath et al., Synthesis and biological activity of fluoro alkylamine derivatives of narcotic analgesics. J Med Chem. Sep. 1980;23(9):985-90.

Rimoldi et al., Basal and hyperaemic myocardial blood flow in regionally denervated canine hearts: an in vivo study with positron emission tomography. Eur J Nucl Med Mol Imaging. Feb. 2007;34(2):197-205. Epub Sep. 2, 2006.

Rise et al., Sodium 2-Mercaptoethanesulfonate in Reversible Adduct Formation and Water Solubilization. Acta Chemica Scandinavica. 1989;43:489-92.

Robins et al., Synthesis and in vitro evaluation of (18)F-labelled S-fluoroalkyl diarylguanidines: Novel high-affinity NMDA receptor antagonists for imaging with PET. Bioorg Med Chem Lett. Mar. 1, 2010;20(5):1749-51. doi: 10.1016/j.bmcl.2010.01.052. Epub Jan. 20, 2010.

Ross et al., Nucleophilic 18F-fluorination of heteroaromatic iodonium salts with no-carrier-added [18F]fluoride. J Am Chem Soc. Jun. 27, 2007;129(25):8018-25. Epub May 31, 2007.

Rundqvist et al., Increased cardiac adrenergic drive precedes generalized sympathetic activation in human heart failure. Circulation. Jan. 7, 1997;95(1):169-75.

Sahul et al., Targeted imaging of the spatial and temporal variation of matrix metalloproteinase activity in a porcine model of postinfarct remodeling: relationship to myocardial dysfunction. Circ Cardiovasc Imaging. Jul. 2011;4(4):381-91. doi: 10.1161/CIRCIMAGING.110. 961854. Epub Apr. 19, 2011.

Sakata et al., Cardiac sympathetic nervous system in early essential hypertension assessed by $^{123}$I-MIBG. J Nucl Med. Jan. 1999;40(1):6-11.

Sasano et al., Abnormal sympathetic innervation of viable myocardium and the substrate of ventricular tachycardia after myocardial infarction. J Am Coll Cardiol. Jun. 10, 2008;51(23):2266-75.

Scholte et al., Cardiac autonomic neuropathy in patients with diabetes and no symptoms of coronary artery disease: comparison of 123I-metaiodobenzylguanidine myocardial scintigraphy and heart rate variability. Eur J Nucl Med Mol Imaging. Aug. 2010;37(9):1698-705. Epub Apr. 22, 2010.

Schoster et al., Contributions to the coordination chemistry of technetium. J Radioanalytical Nuclear Chem. 1996;211(2):403-24.

Schwartz, The autonomic nervous system and sudden death. Eur Heart J. Jun. 1998;19 Suppl F:F72-80.

Shah et al., The synthesis of [18F]fluoroarenes from the reaction of cyclotron-produced [18F]fluoride ion with diaryliodonium salts. J Chem Socs, Perkin Trans 1. 1998;2043-6.

Sherif et al., Evaluation of a novel (18)F-labeled positron-emission tomography perfusion tracer for the assessment of myocardial infarct size in rats. Circ Cardiovasc Imaging. Mar. 2009;2(2):77-84. Epub Jan. 26, 2009.

Simões et al., Presence of sympathetically denervated but viable myocardium and its electrophysiologic correlates after early revascularised, acute myocardial infarction. Eur Heart J. Apr. 2004;25(7):551-7.

Smith et al., Autonomic tone attenuates drug-induced QT prolongation. J Cardiovasc Electrophysiol. Sep. 2007;18(9):960-4. Epub Jul. 30, 2007.

Stevens et al., Cardiac sympathetic dysinnervation in diabetes: implications for enhanced cardiovascular risk. Circulation. Sep. 8, 1998;98(10):961-8.

Stoll et al., Application of n.c.a. 4-[$^{18}$F]fluorophenol in diaryl ether syntheses of 2-(4-[$^{18}$F]fluorophenoxy)-benzylamines. J Labelled Comp Radiopharm. 2004;47:443-55.

Su et al., Noninvasive targeted imaging of matrix metalloproteinase activation in a murine model of postinfarction remodeling. Circulation. Nov. 15, 2005;112(20):3157-67. Epub Nov. 7, 2005.

Sun et al., Room-temperature nucleophilic aromatic fluorination: experimental and theoretical studies. Angew Chem Int Ed Engl. Apr. 21, 2006;45(17):2720-5.

Tavakoli et al., Matrix metalloproteinase activation predicts amelioration of remodeling after dietary modification in injured arteries. Arterioscler Thromb Vase Biol. Jan. 2011;31(1):102-9. doi: 10.1161/ATVBAHA.110.216036. Epub Oct. 14, 2010.

Tekabe et al., Noninvasive monitoring the biology of atherosclerotic plaque development with radiolabeled annexin V and matrix metalloproteinase inhibitor in spontaneous atherosclerotic mice. J Nucl Cardiol. Dec. 2010;17(6):1073-81. doi: 10.1007/s12350-010-9276-5. Epub Aug. 11, 2010.

Thiebes et al., Mild preparation of haloarenes by ipso-substitution of arylboronic acids with N-halosuccinimides. Synlett. Feb. 1998:141-42.

Thompson et al., The conversion of phenols to the corresponding aryl halides under mild conditions. Synthesis. 2005; (4)547-50.

Tius et al., Synthetic communications: an international journal for rapid communication of synthetic organic chemistry. Synth Commun. 1992;22(10):1461-71.

Travin, Cardiac neuronal imaging at the edge of clinical application. Cardiol Clin. May 2009;27(2):311-27.

Vaidyanathan et al., (4-[18F]fluoro-3-iodobenzyl)guanidine, a potential MIBG analogue for positron emission tomography. J Med Chem. Oct. 14, 1994;37(21):3655-62.

Vaidyanathan et al., Biological evaluation of ring- and side-chain-substituted m-odobenzylguanidine analogues. Bioconjug Chem. Sep.-Oct. 2001;12(5):798-806.

Vaidyanathan et al., No-carrier-added iodine-131-FIBG: evaluation of an MIBG analog. J Nucl Med. Feb. 1997;38(2):330-4.

Vaidyanathan et al., No-carrier-added synthesis of a 4-methyl-substituted metaiodobenzylguanidine analogue. Appl Radiat Isot. Mar. 2005;62(3):435-40.

Vaidyanathan et al., Validation of 4-[fluorine-18]fluoro-3-iodobenzylguanidine as a positron-emitting analog of MIBG. J Nucl Med. Apr. 1995;36(4):644-50.

Valette et al., Bromine-76-metabromobenzylguanidine: a PET radiotracer for mapping sympathetic nerves of the heart. J Nucl Med. Oct. 1993;34(10):1739-44.

Wagner et al., Synthesis of an 18F-labelled high affinity β1-adrenoceptor PET radioligand based on ICI 89,406. J Label Compd Radiopharm. Feb. 2006;49(2):177-95.

Wang et al., Synthesis and preliminary biological evaluation of O6-[4-(2-[18F]fluoroethoxymethyl)benzyl]guanine as a novel potential PET probe for the DNA repair protein O6-alkylguanine-DNA alkyltransferase in cancer chemotherapy. Bioorg Med Chem. Oct. 15, 2005;13(20):5779-86.

Watson et al., Formation of ArF from LPdAr(F): catalytic conversion of aryl triflates to aryl fluorides. Science. Sep. 25, 2009;325(5948):1661-4. Epub Aug. 13, 2009. Erratum: Jul. 2, 2010.

(56) References Cited

OTHER PUBLICATIONS

Wieland et al., Adrenal medulla 1,2,7,11 imaging agents: a structure-distribution relationship study of radiolabeled aralkylguanidines. J Medic Chem. Feb. 1, 1984;27(2):149-55.

Wiesel et al., The Transport of Tyrosine into the Human Brain as Determined with L-[1-11C]Tyrosine and PET. J Nucl Med. 1991;32:2043-49.

Wilen et al., Strategies in Optical Resolutions. Tetrahedron. 1977;33:2725-36.

Wilen, Tables of Resolving Agents and Optical Resolutions. E.L. Eliel, ed. University of Notre Dame Press, Notre Dame, IN. 1972:268-98.

Wu et al., Studies on Synthesis of the new Precursors of 18F Labelled Amino Acids Radiopharmaceuticals for Positron Emission Tomography. Chinese Doctoral Dissertations Full-text Database (Medicine and Health Sciences). 2009;7:E79-12, pp. 7-10.

Yamada et al., Convenient electrophilic fluorination of functionalized aryl and heteroaryl magnesium reagents. Angew Chem Int Ed Engl. Mar. 15, 2010;49(12):2215-8.

Yu et al., BMS-747158-02: a novel PET myocardial perfusion imaging agent. J Nucl Cardiol. Nov.-Dec. 2007;14(6):789-98. Epub Oct. 22, 2007.

Yu et al., Cardiac imaging and safety evaluation of BMS747158, a novel PET myocardial perfusion imaging agent, in chronic myocardial compromised rabbits. J Nucl Cardiol. Aug. 2010;17(4):631-6. Epub Mar. 26, 2010.

Yu et al., Evaluation of LMI1195, a novel 18F-labeled cardiac neuronal PET imaging agent, in cells and animal models. Circ Cardiovasc Imaging. Jul. 2011;4(4):435-43. Epub May 9, 2011.

Yu et al., LMI1195: A New 18F Benzylguanidine Analog for PET Cardiac Sympathetic Neuronal Imaging. AHA Scientific Session 2009. Orlando, FL. Nov. 15-17, 2009. Abstract Only.

Yu et al., The next generation of cardiac positron emission tomography imaging agents: discovery of flurpiridaz F-18 for detection of coronary disease. Semin Nucl Med. Jul. 2011;41(4):305-13. doi: 10.1053/j.semnuclmed.2011.02.004.

Zhdankin et al., Chemistry of polyvalent iodine. Chem Rev. Dec. 2008;108(12):5299-358.

Zhou et al., An efficient and regioselective monobromination of electron-rich aromatic compounds using catalytic hypervalent iodine (III) reagent. Synthesis. 2011;(2):207-09.

Zipes, Cardiac Electrophysioloigy: From Cell to Bedside. Zipes et al., eds. W.B. Saunders, Philadelphia. 1995:441-53.

U.S. Appl. No. 15/593,540, filed May 12, 2017, Purohit et al.
U.S. Appl. No. 15/364,678, filed Nov. 30, 2016, Radeke et al.
EP 12152815.2, Jun. 20, 2012, Extended European Search Report.
EP 12152816.0, Jun. 20, 2012, Extended European Search Report.
EP 12152817.8, Jun. 22, 2012, Extended European Search Report.
EP 12152818.6, Jun. 22, 2012, Extended European Search Report.
PCT/US2007/088500, Dec. 19, 2008, Invitation to Pay Additional Fees.
PCT/US2007/088500, Mar. 13, 2009, International Search Report and Written Opinion.
PCT/US2007/088500, Jul. 9, 2008, International Preliminary Report on Patentability.
U.S. Appl. No. 16/828,119, filed Mar. 24, 2020, Radeke et al.
EP 19200889.4, Mar. 30, 2020, Extended European Search Report.
Extended European Search Report for EP 19200889.4 dated Mar. 30, 2020.

* cited by examiner

LIGANDS FOR IMAGING CARDIAC INNERVATION

RELATED APPLICATIONS

This application is a Continuation of U.S. application Ser. No. 13/916,205, filed Jun. 12, 2013, entitled "LIGANDS FOR IMAGING CARDIAC INNERVATION", which is a Continuation of U.S. application Ser. No. 12/448,575, filed May 14, 2010, entitled "LIGANDS FOR IMAGING CARDIAC INNERVATION", which is a national stage filing under 35 U.S.C. 371 of International Patent Application Serial No. PCT/US2007/088500, filed Dec. 21, 2007, entitled "LIGANDS FOR IMAGING CARDIAC INNERVATION", which is a Non-Prov of Prov (35 USC 119(e)) of U.S. application Ser. No. 60/877,211, filed Dec. 26, 2006, entitled "LIGANDS FOR IMAGING CONGESTIVE HEART FAILURE". The entire contents of these applications are incorporated herein by reference in their entirety.

FIELD OF THE INVENTION

Novel compounds that find use as imaging agents within nuclear medicine applications (e.g., PET imaging and SPECT imaging) are disclosed. Methods of using the compounds to image cardiac innervation are also provided.

BACKGROUND OF THE INVENTION

Heart failure (HF) is a condition that afflicts increasingly more people each year. This condition is defined as the common end-stage of many frequent cardiac diseases (e.g. myocardial infarction, pressure overload, volume overload, viral myocarditis, toxic cardiomyopathy), and is characterized by relentless progression. The resultant myocardial damage from such events in conjunction with neurohormonal and cytokine activation, is suspect for the causes of chamber remodeling of the heart, an initial phase of HF. Early diagnosis of HF is difficult because the remodeling process precedes the development of symptoms by months or even years. The current diagnostic tests (e.g. two dimensional echocardiogram coupled with Doppler flow studies) only reveal changes in the heart in the late stages of the disease. To date, no cure for HF exists. Early diagnosis is a key factor in achieving a good prognosis and management of this disease.

An imaging agent that identifies patients in early HF would enable immediate treatment and life-style improvements for those living with this disease. In the past, researchers have investigated a variety of biological markers found in HF to develop methods for detection of early stages of HF. The cardiac sympathetic nervous system (CSNS), which is part of the autonomic nervous system, was found to be one of the biological markers of interest.

The autonomic nerve system, which plays a crucial role in regulating cardiac function, consists of the CSNS and the cardiac parasympathetic nervous system (CPNS). In the two branches of the cardiac autonomic innervations, the CSNS and CPNS, postganglionic sympathetic neurons communicate with each other via the neurotransmitter norepinephrine (NE). These branches work in finely tuned opposition to each other in the heart. Thus stimulus to the sympathetic nerve system causes increased contractility, acceleration of heart rate and conduction, which is mediated by the action of NE on post synaptic $\beta_1$ adrenoceptors. Stimulation of the parasympathetic nerves on the other hand, leads to a decrease in heart rate and conduction. This is mediated by action of acetylcholine on postsynaptic $M_2$ muscarinic acctylcholine receptors.

NE is the neurotransmitter of postganglionic sympathetic neurons. NE is stored in vesicles within the neurons and is released by $Ca^{+2}$ mediated exocytosis into the synaptic cleft upon nerve depolarization. Most of the norepinephrine released is returned to the neuron by the norepinephrine transporter (NET; also known as "Uptake-1" mechanism) and repackaged into storage vesicles by the vesicular monoamine transporter (VMAT). The remaining amount of NE in the synaptic cleft binds to postsynaptic $\beta 1$ adrenoceptors controlling heart contractility, acceleration of heart rate and heart conduction. Tissue concentrations of NE in the normal heart are generally considered to be reliable markers of regional sympathetic nerve density, which are uniformly distributed throughout the heart.

Abnormalities in cardiac innervation have been implicated in the pathophysiology of many heart diseases, including sudden cardiac death, congestive heart failure, diabetic autonomic neuropathy, myocardial ischemia and cardiac arrhythmias. Heart failure is characterized by a hyperadrenergic state whereby increased systemic levels of NE and increased local spillover of catecholamines occurs. It has been documented that there is a reduction in cardiac uptake-1 density or function in tissue samples of both human patients and animal models, which may be the reason for the increased amount of systemic NE observed in myocardium tissue. Development of methods to assess physiological changes of NE uptake-1 in the myocardium are therefore highly desirable.

As disclosed in United States Patent Application Publication No. 20060127309 (herein incorporated by reference in its entirety), medical radionuclide imaging (e.g., Nuclear Medicine) is a key component of modern medical practice. This methodology involves the administration, typically by injection, of tracer amounts of a radioactive substance (e.g., radiotracer agents, radiotherapeutic agents, and radiopharmaceutical agents), which subsequently localize in the body in a manner dependent on the physiologic function of the organ or tissue system being studied. The radiotracer emissions, most commonly gamma photons, are imaged with a detector outside the body, creating a map of the radiotracer distribution within the body. When interpreted by an appropriately trained physician, these images provide information of great value in the clinical diagnosis and treatment of disease. Typical applications of this technology include detection of coronary artery disease (e.g., thallium scanning) and the detection of cancerous involvement of bones (e.g., bone scanning). The overwhelming bulk of clinical radionuclide imaging is performed using gamma emitting radiotracers and detectors known as "gamma cameras."

Recent advances in diagnostic imaging, such as magnetic resonance imaging (MRI), computerized tomography (CT), single photon emission computerized tomography (SPECT), and positron emission tomography (PET) have made a significant impact in cardiology, neurology, oncology, and radiology. Although these diagnostic methods employ different techniques and yield different types of anatomic and functional information, this information is often complementary in the diagnostic process. Generally speaking, PET uses imaging agents labeled with the positron-emitters such as $^{18}F$, $^{11}C$, $^{13}N$ and $^{15}O$, $^{75}Br$, $^{76}Br$ and $^{124}I$. SPECT uses imaging agents labeled with the single-photon-emitters such as $^{201}Tl$, $^{99}Tc$, $^{123}I$, and $^{131}I$.

Glucose-based and amino acid-based compounds have also been used as imaging agents. Amino acid-based compounds are more useful in analyzing tumor cells, due to their faster uptake and incorporation into protein synthesis. Of the amino acid-based compounds, [11]C- and $^{18}$F-containing compounds have been used with success. $^{11}$C-containing radiolabeled amino acids suitable for imaging include, for example, L-[1-$^{11}$C]leucine, L-[1-$^{11}$C]tyrosine, L-[methyl-$^{11}$C]methionine and L-[1-$^{11}$C]methionine.

PET scans involve the detection of gamma rays in the form of annihilation photons from short-lived positron emitting radioactive isotopes including, but not limited to $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method. For PET imaging studies of cardiac sympathetic innervation, carbon-11 ($^{11}$C) labeled compounds such as [$^{11}$C]meta-hydroxyephedrine (HED) are frequently used at major PET centers that have in-house cyclotrons and radiochemistry facilities. Recently the nuclear medicine market has seen a substantial increase in stand-alone PET imaging centers that do not have cyclotrons. These satellite-type facilities typically use 2-[$^{18}$F]fluoro-2-deoxy-D-glucose (FDG) for PET imaging of cancerous tumors.

SPECT, on the other hand, uses longer-lived isotopes including but not limited to $^{99m}$Tc with a half-life of approximately 6 hours and $^{201}$Tl with a half-life of approximately 74 hours. The resolution in present SPECT systems, however, is lower than that presently available in PET systems.

Radiotracers targeting each branch of cardiac autonomic innervation have been developed. The number of tracers developed for the sympathetic neurons however is far more than those developed for the parasympathetic neurons. There are two reasons for this. First, the NET is nonselective and will readily transport structural analogs of NE into the sympathetic varicosity. The choline uptake carrier on the other hand is highly selective. Second, there is a dense population of the sympathetic nerves in the left ventricular wall as compared to the parasympathetic neurons found in the thin walls of the atria and conduction nodes. This has therefore, made imaging the sympathetic neurons easier. The structures below are examples of radiolabel led catecholamines and catecholamine analogues, and guanadines used for studying cardiac sympathetic neurons.

Radiolabelled Catecholamines and Catecholamine Analogues, and Guanidines Used for Studying Cardiac Sympathetic Neurons Catecholamines

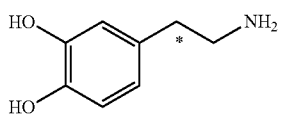

[$^{11}$C]Dopamine (DA)

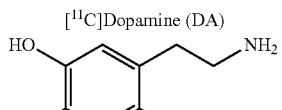

6-[$^{18}$F]Fluorodopamine (FDA)

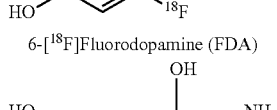

[$^{11}$C]Norepinephrine (NE)

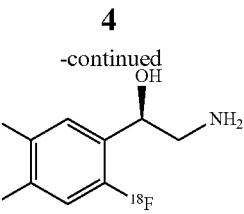

6-[$^{18}$F]Fluoronorepinephrine (FNE)

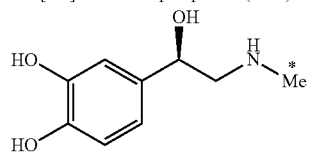

[$^{11}$C]Epinephrine (EPI)

Catecholamine analogues

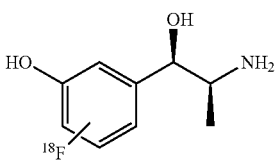

4- and 6-[18F]Fluormetaraminol (FMR)

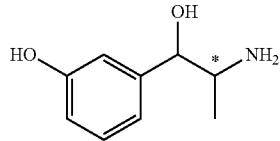

[$^{11}$C]Metaraminol (MR)

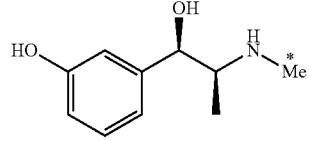

[$^{11}$C]meta-hydroxyephedrine (HED)

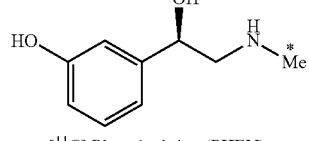

[$^{11}$C] Phenylephrine (PHEN)

Guanidines

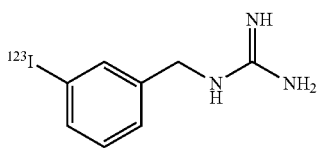

[$^{123}$I]-m-Iodobenzylguanidine (MIBG)

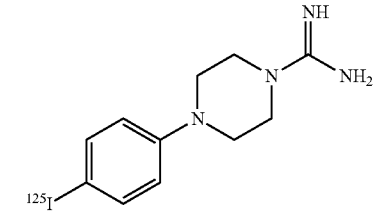

[$^{125}$I]-1-carboxamidino-4-phenylpiperazine (CAAP)

[$^{11}$C]Dopamine ([$^{11}$C]DA) and 6-[$^{18}$F]fluorodopamine (6-[$^{18}$F]FDA) have been used to image dogs and baboons respectively. 6-[$^{18}$F]FDA showed rapid uptake and clearance, and good images of the heart. [$^{11}$C]Norepinephrine ([$^{11}$C]NE) has been used to obtain planar images of canine heart and clearly visualized the left ventricular myocardium in a cynomologous monkey. 6-[$^{18}$F]Fluoronorepinephrine (6-[$^{18}$F]FNE) has also been used to image the baboon heart and showed high uptake and retention. Myocardial kinetics of [$^{11}$C]epinephrine ([$^{11}$C]EPI) has been extensively studied and is handled in a similar manner to NE and has been used to assess neuronal changes in cardiac transplant patients.

The catecholamine analogues like 1R,2S-6-[$^{18}$F]-fluoro-metaraminol (6-[$^{18}$F]FMR), [$^{11}$C]hydroxyephedrine ([$^{11}$C]HED) and [$^{11}$C]phenylephrine ([$^{11}$C]PHEN) have also been used very effectively to study the sympathetic nerve system. [$^{123}$]-meta-Iodobenzylguanidine (MIBG) is another extensively studied catecholamine analog that shows neuronal uptake as well as uptake by the cardiac myocytes, when studying sympathetic nerve fibers of the heart. Studies with MIBG allow clinicians to map the regional distribution of nerve fibers in the heart using imaging devices found in all nuclear medicine clinics. MIBG is also used for diagnostic imaging and radiotherapy of adrenergic tumors, such as neuroblastoma and pheochromocytoma. [$^{123}$I]MIBG has been used to delineate nerve damage while [$^{11}$C]HED has been used to demonstrate neuronal abnormalities in a number of heart conditions including transplanted hearts, cardiomyopathy, acute myocardial infarction and cardiac diabetic neuropathy. MIBG is a SPECT tracer, however, and therefore does not provide quantitative information.

Lastly, [$^{125}$I]-CAAP was the first $^{125}$I-radiolabeled 1-carboxamidino-4-phenyl-piperazine. Comparison studies of [$^{125}$I]-CAAP with [$^{125}$I]-MIBG in tissue distribution studies in rats demonstrated equivalent uptake of the radiotracer in heart tissue. The uptake and retention of the compounds in the myocardium tissue are speculated to be due to the same mechanism of action, which recognizes the guanidine functionality in both substrates. NET uptake-1 is a possible mode of action. Several positron emitting radiotracers were therefore developed as shown below.

MIBG and Positron Emitting Analogues

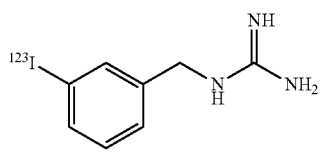

[$^{123}$I]-m-Iodobenzylguanidine (MIBG)

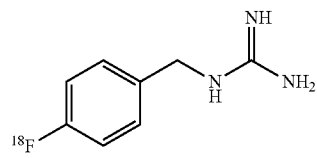

[$^{18}$F]-p-Fluorobenzylguanidine (PFBG)

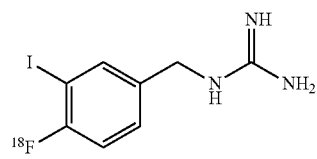

4-[$^{18}$F]-Fluoro-3-iodobenzylguanidine (FIBG)

-continued

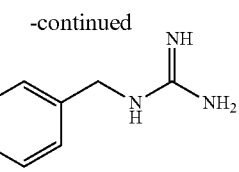

[$^{76}$Br]-m-Bromobenzylguanidine (MBBG)

Of the three benzylguanidine PET tracers developed only one, 4-[$^{18}$F]fluoro-3-iodobenzylguanidine ([$^{18}$F]FIBG) demonstrated uptake and behavior similar to MIBG in vivo.

All the tracers mentioned above give valuable information but have their limitations. These include metabolic instability (NE, FNE, DA, FDA, PHEN, EPI and CAAP) or pharmacologically active norepinephrine release (FMR). MIBG also has its drawbacks. It has considerable extraneuronal uptake mediated by passive diffusion and by the uptake-2 (membrane transport) mechanism. And, being a SPECT agent, like CAAP, MIBG does not give quantitative information and has other associated limitations. There is therefore a need for tracers that will show the following characteristics:
a) stability,
b) not cause NE release (thereby reducing side effects),
c) give quantitative information, and/or
d) high affinity for VMAT.

SUMMARY OF THE INVENTION

The present invention provides novel compounds that find use as imaging agents within nuclear medicine applications (e.g., PET imaging and SPECT imaging). Methods of using the compounds to image cardiac innervation are also provided. In some embodiments of the present invention, the PET based radiotracers exhibit increased stability, decreased NE release (thereby reducing side effects), improved quantitative information, and/or high affinity for VMAT. In certain embodiments, these tracers are based on compounds that are derivatized with $^{18}$F in a variety of positions: aryl, alkyl, a keto, benzylic, beta-alkylethers, gamma-propylalkylethers and beta-proplylalkylethers, as shown in their structures below. In alternative embodiments, a methyl group α is added to the amine, and/or the catechol functionality is either eliminated or masked as a way of making these molecules more stable.

One embodiment of the present invention provides PET based radiotracers as illustrated in the general structure I:

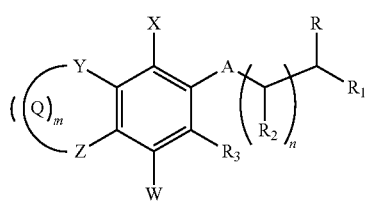

wherein m=0, 1, or 2; n=0, 1, 2, and A is O or absent. R, $R_1$, $R_2$, and $R_3$ are independently selected from the group consisting of H, $OR_4$, F, Cl, $CF_3$, Br, 1, alkyl ($C_1$-$C_4$), aryl, heteroaryl, C(=O)$R_4$, $CO_2R_4$, $N(R_4)_2$, CN, C(=NH)$NHR_5$, C(=O)$NHR_5$, NHC(=O)$NR_5$, $NHNR_5$, $SO_2OR_5$, and imaging moiety Im. Q consists of bridging groups that can be present between Y and Z, and to $R_2$. The Q bridging groups can independently be selected from the group consisting of $CH_2$, CH, $CR_5$, N, NH, $NR_5$, O and S in such a combination as to create a chemically stable structure. The substituents W, X, Y and Z may independently be selected from the group consisting of H, $OR_4$, $NR_4$, F, Cl, Br, I, Im, aryl, and heteroaryl. $R_4$ and $R_5$ may be H, alkyl, aryl or heteroaryl substituents. In an alternative embodiment, the alkyl, aryl or heteroaryl substituents may be substituted with various functional groups as hereinafter described.

In certain embodiments, the present invention provides a PET based radiotracer having structure II as follows:

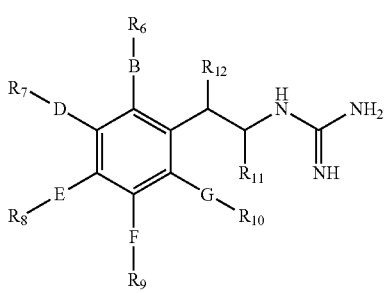

wherein linking groups B, D, E, F, and G are independently selected from the group consisting of a bond, alkyl ($C_1$-$C_5$; preferably $C_2$), aryl, aralkyl, alkylaryl, heteroaryl, alkoxy, alkylamino, aminoalkyl, aryloxy, alkoxyalkyl, thioalkyl, and heterocyclyl. $R_6$ through $R_{12}$ are independently selected from the group consisting of H, $OR_4$, F, Cl, $CF_3$, Br, I, alkyl ($C_1$-$C_4$), aryl, heteroaryl, C(=O)$R_4$, $CO_2R_4$, $N(R_4)_2$, CN, C(=NH)$NHR_5$, C(=O)$NHR_5$, NHC(=O)$NR_5$, $NHNR_5$, $SO_2OR_5$, and imaging moiety Im. $R_4$ and $R_5$ may be H, alkyl, aryl or heteroaryl substituents. And, Im is selected from the group consisting of $^{18}F$, $^{76}Br$, $^{124}I$, $^{99m}Tc$, $^{153}Gd$, $^{111}In$, and $^{90}Y$.

In certain embodiments, the present invention provides a PET based radiotracer compound having the following Structure Alpha:

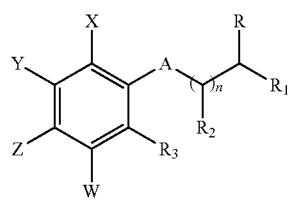

wherein n=0, 1, 2, 3 and A is O or absent. R, $R_1$, $R_2$ and $R_3$ are independently selected from the group consisting of H, $OR_4$, F, Cl, Br, I, $CF_3$, alkyl ($C_1$-$C_4$), aryl, heteroaryl, C(=O)$R_4$, $CO_2R_4$, $N(R_4)_2$, CN, C(=$NR_4$)$OR_5$, $NR_4$(C(=$NR_5$)$NHR_6$, C(=$NR_4$)$NHR_5$, C(=O)$NHR_4$, $NR_4$C(=O)$NR_5$, $NR_4NR_5$, $SO_2OR_4$, and Im. The substituents W, X, Y and Z can independently be selected from the group consisting of H, $OR_4$, $N(R_4)_2$, F, Cl, Br, I, $CF_3$, Im, aryl, and heteroaryl. $R_4$, $R_5$, and $R_6$ are H, alkyl, aryl or heteroaryl substituents. And, the imaging moiety, Im, can be selected from the group consisting of $^{18}F$, $^{76}Br$, $^{124}I$, $^{131}I$, $^{99m}Tc$, $^{153}Gd$, or $^{111}In$.

In addition, in a further embodiment, the invention also provides a PET radiotracer compound having Structure Beta:

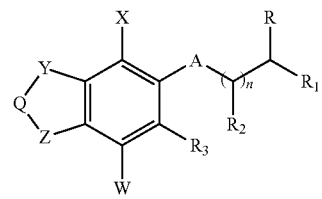

wherein n=0, 1, 2, 3 and A=O or is absent. R, $R_1$, $R_2$ and $R_3$ are independently selected from the group consisting of H, $OR_4$, F, Cl, Br, I, $CF_3$, alkyl ($C_1$-$C_4$), aryl, heteroaryl, C(=O)$R_4$, $CO_2R_4$, $N(R_4)_2$, CN, C(=$NR_4$)$OR_5$, $NR_4$(C(=$NR_5$)$NHR_6$, C(=$NR_4$)$NHR_5$, C(=O)$NHR_4$, $NR_4$C(=O)$NR_5$, $NR_4NR_5$, $SO_2OR_4$, and Im. The substituents W and X can independently be selected from the group consisting of H, $OR_4$, $N(R_4)_2$, F, Cl, Br, I, $CF_3$, Im, aryl, and heteroaryl. Y and Z can be selected from the group consisting of CH, $CH_2$, O, N, $NR_7$, and CH=CH. Bridging group Q is absent or selected from the group consisting of CH, $CR_4$, $CH_2$, N, $NR_4$, NH, S, and O. $R_4$, $R_5$, and $R_6$ are H, alkyl, aryl or heteroaryl substituents.

In certain embodiments, the present invention provides a PET based radiotracer having Structure Chi as follows:

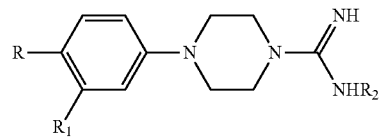

wherein R through $R_2$ are independently selected from the group consisting of H, $OR_3$, F, Cl, Br, I, $CH_2F$, $OCH_2CH_2F$, alkyl ($C_1$-$C_4$), aryl, heteroaryl, C(=O)$R_3$, $CO_2R_3$, and Im. Im is a imaging moiety and is selected from the group consisting of $^{18}F$, $^{76}Br$, $^{124}I$, and $^{131}I$. $R_3$ can be an H, alkyl, aryl or heteroaryl substituent.

In certain embodiments, the present invention provides a PET based radiotracer having Structure Delta as follows:

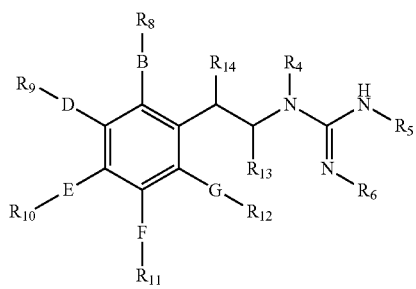

wherein linking groups B, D, E, F and G are independently selected from the group consisting of a bond, alkyl ($C_1$-$C_5$; preferably $C_2$), aryl, aralkyl, alkylaryl, heteroaryl, alkoxy, alkylamino, aryloxy, and alkoxyalkyl. $R_8$ through $R_{14}$ are independently selected from the group consisting of H, $OR_3$, F, Cl, Br, I, $CH_2F$, $OCH_2CH_2F$, alkyl ($C_1$-$C_4$), aryl, heteroaryl, C(=O)$R_3$, $CO_2R_3$, and Im. $R_3$, $R_4$, $R_5$, and $R_1$ can independently be selected from the group consisting of H, alkyl, aryl, aralkyl, heteroaryl, alkylamino, alkyloxy, and aryloxy. The imaging moiety, Im, can be selected from the group consisting of $^{18}F$, $^{76}Br$, $^{124}I$, $^{131}I$, $^{99m}TC$, $^{153}Gd$, and $^{111}In$.

A preferred embodiment describes the PET based radiotracer compound N-[3-bromo-4-(3-[$^{18}$F]fluoropropoxy)-benzyl]-guanidine hydrochloride, as illustrated in Structure Epsilon below:

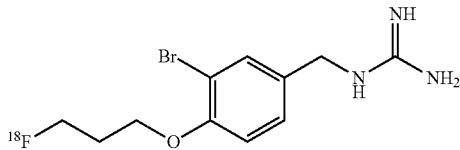 [SMILES: N=C(N)NCc1ccc(OCCC[18F])c(Br)c1]

A further embodiment describes a method of imaging cardiac innervation comprising the steps of: administering an effective amount of one or more of the compounds disclosed above, to a patient; detecting gamma radiation emitted by said compound; and forming an image therefrom.

The present invention is directed to these, as well as other important ends, hereinafter described.

DETAILED DESCRIPTION OF THE EMBODIMENTS

Definitions

Figure 1:
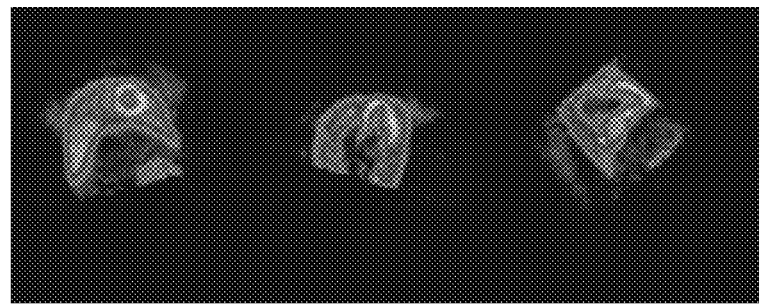
FIG. 1 is a first series of representative cardiac short- and long-axis images in a non-human primate according to an embodiment of the invention.

Unless otherwise indicated, the term "lower alkyl" as may be employed herein alone or as part of another group includes both straight and branched chain hydrocarbons containing 1 to 8 carbons, and the terms "alkyl" and "alk" as may be employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or CF$_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkylamino, alkanoylamino, arylcarbonylamino, nitro, cyano, thiol, haloalkyl, trihaloalkyl and/or alkylthio.

Unless otherwise indicated, the term "cycloalkyl" as may be employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

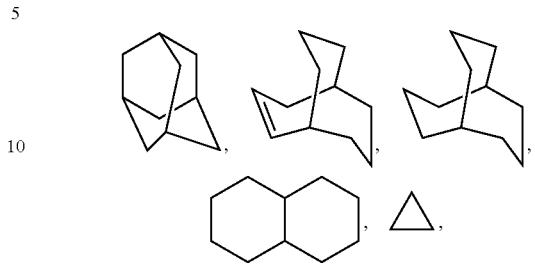

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

The term "heterocyclo", "heterocycle", "heterocyclyl" or "heterocyclic ring", as may be used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "alkanoyl" as may be used herein alone or as part of another group refers to alkyl linked to a carbonyl group.

The term "halogen" or "halo" as may be used herein alone or as part of another group refers to chlorine, bromine, fluorine, and iodine, with chlorine or fluorine or bromine sometimes being preferred.

Unless otherwise indicated, the term "aryl" or "Aryl" as may be employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings). For example

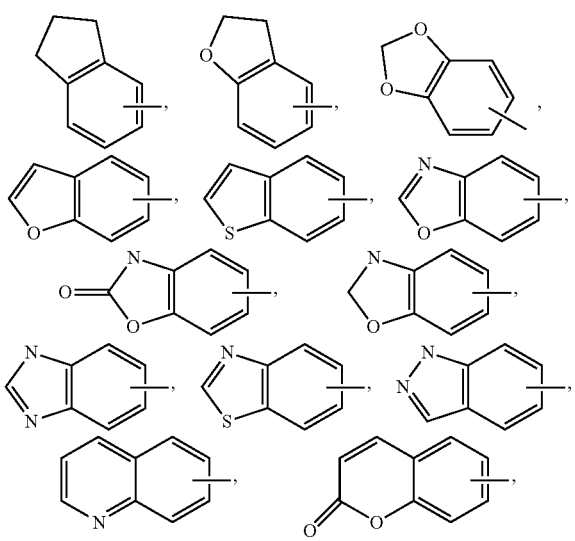

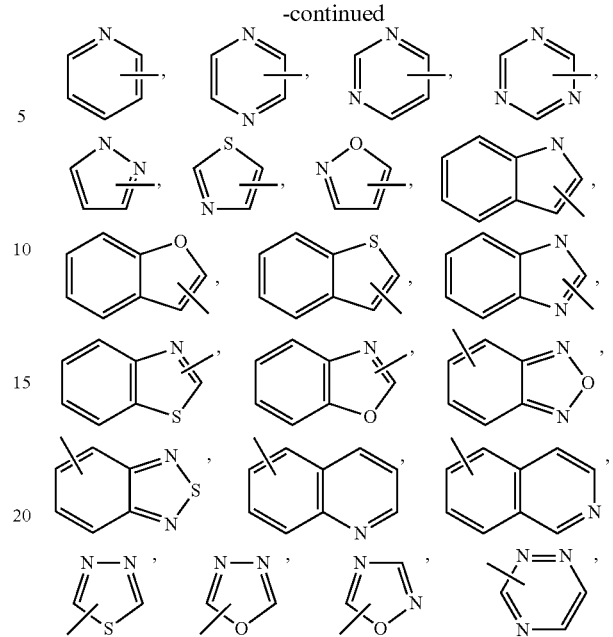

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "heteroaryl" as may be used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

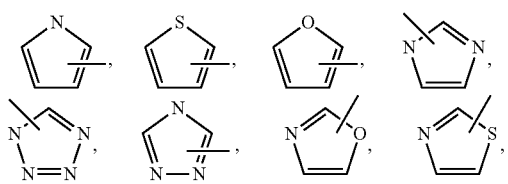

and the like.

Unless otherwise indicated, the term "lower alkoxy", "alkoxy", "aryloxy" or "aralkoxy" as may be employed herein alone or as part of another group includes any of the above alkyl, aralkyl or aryl groups linked to an oxygen atom.

Unless otherwise indicated, the term "lower alkylthio", "alkylthio", "arylthio" or "aralkylthio" as may be employed herein alone or as part of another group includes any of the above alkyl, aralkyl or aryl groups linked to a sulfur atom.

The term "polyhaloalkyl" as may be used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as may be used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The terms "$R_n$" as used herein are to be construed with reference to the specific structure in which are utilized and described, and may be used more than once.

PET based radiotracers for mapping the nervous system have been developed in an attempt to address the limitations of prior radiotracers. In some embodiments of the present invention, the PET based radiotracers are developed to exhibit increased stability, decreased NE release (thereby reducing side effects), improved quantitative information, and/or high affinity for VMAT. In certain embodiments, these tracers are based on compounds that are derivatized with $^{18}F$ in a variety of positions: aryl, alkyl, a keto, benzylic, beta-alkylethers, gamma-propylalkylethers and beta-proplylalkylethers, as shown in their structures below. In alternative embodiments, a methyl group a is added to the amine, and/or the catechol functionality is either eliminated or masked as a way of making these molecules more stable.

PET based radiotracers for mapping the cardiac sympathetic nerve system include General Structures I and II:

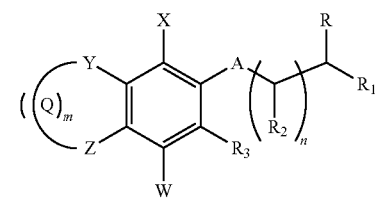

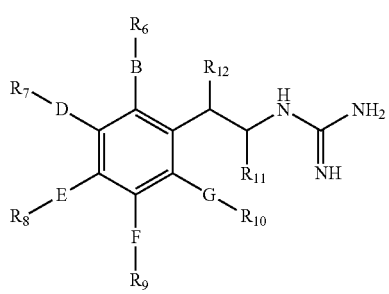

Examples of compounds represented by General Structures I & II include the following:

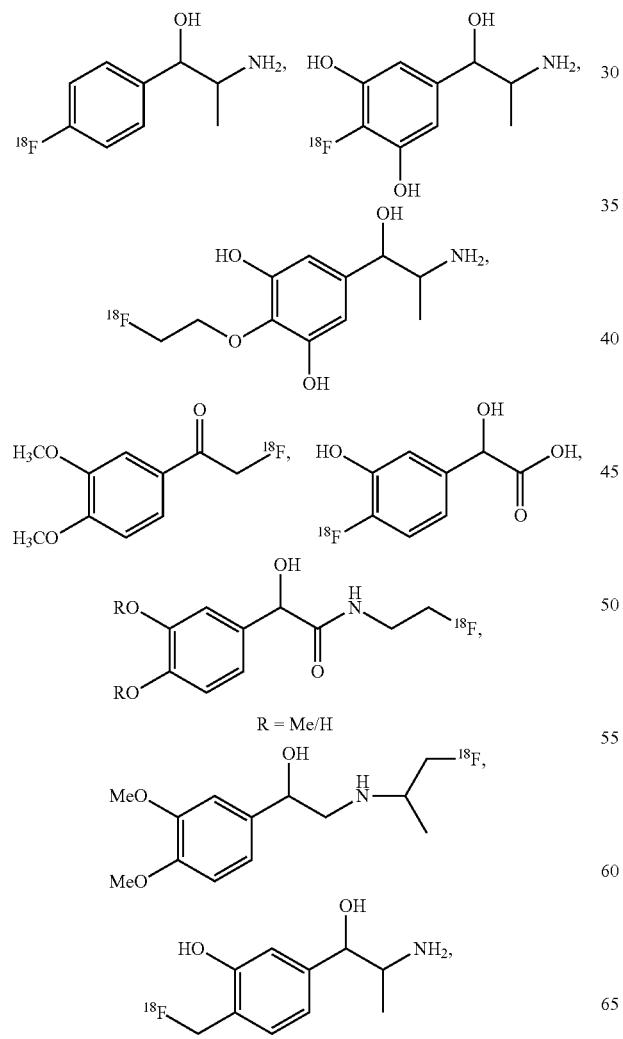

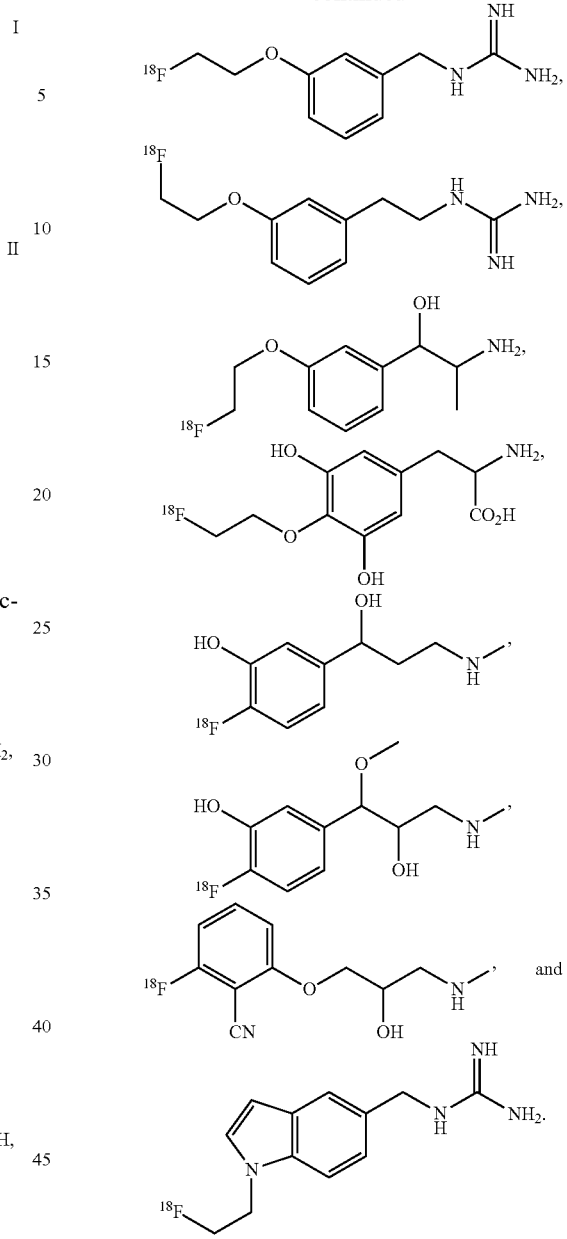

One embodiment of the present invention provides PET based radiotracers as illustrated in the General Structure I above, wherein m=0, 1, or 2; n=0, 1, 2, and A is O or absent. R, $R_1$, $R_2$, and $R_3$ are independently selected from the group consisting of H, $OR_4$, F, Cl, $CF_3$, Br, I, alkyl ($C_1$-$C_4$), aryl, heteroaryl, C(=O)$R_4$, $CO_2R_4$, N($R_4$)$_2$, CN, C(=NH)NH$R_5$, C(=O)NH$R_5$, NHC(=O)N$R_5$, NHN$R_5$, SO$_2$O$R_5$, and imaging moiety Im. Q comprises bridging groups that can be present between Y and Z, and to $R_2$. The Q bridging groups can independently be selected from the group consisting of $CH_2$, CH, C$R_5$, N, NH, N$R_5$, O and S in such a combination as to create a chemically stable structure. The substituents W, X, Y and Z may independently be selected from the group consisting of H, O$R_4$, N$R_4$, F, Cl, Br, I, Im, aryl, and heteroaryl. $R_4$ and $R_5$ may be H, alkyl, aryl or heteroaryl substituents. In an alternative embodiment, the alkyl, aryl or heteroaryl substituents may be substituted with various functional groups selected from the group consisting of, but not limited to, halogen (F, Cl, Br, I), OH, $NH_2$, COOH, Im, $COOR_{13}$, $CON(R_{13})_2$, $SR_{13}$, $OR_{13}$, $NHC(=NH)NH_2$, $NHC(=O)NH_2$, $NHC(=O)N(R_{13})_2$, $C(=NH)NH_2$, $C(=NR_{13})N(R_{13})_2$ and $N(R_{13})_2$, in which $R_{13}$ may be hydrogen, alkyl, aryl or alkylaryl.

Another embodiment provides PET based radiotracers as illustrated in the General Structure II above, wherein linking groups B, D, E, F and G are independently selected from the group consisting of a bond, alkyl ($C_1$-$C_5$; preferably $C_2$), aryl, aralkyl, alkylaryl, heteroaryl, alkoxy, alkylamino, aryloxy, alkoxyalkyl, and heterocyclic. $R_6$ through $R_{12}$ may be independently selected from the group consisting of H, $OR_4$, F, Cl, $CF_3$, Br, I, alkyl ($C_1$-$C_4$), aryl, heteroaryl, $C(=O)R_4$, $CO_2R_4$, $N(R_4)_2$, CN, $C(=NH)NHR_5$, $C(=O)NHR_5$, $NHC(=O)NR_5$, $NHNR_5$, $SO_2OR_5$, and Im. $R_4$ and $R_5$ may be H, alkyl, aryl or heteroaryl substituents, and Im is an imaging moiety that may be selected from the group consisting of $^{18}F$, $^{76}Br$, $^{124}I$, $^{131}I$, $^{99m}Tc$, $^{153}Gd$, $^{111}In$, and $^{90}Y$. And, provided that in the case where any one of $R_6$-$R_{10}$ equals Im, the linking group B, D, E, F or G, which attaches the imaging moiety to the phenyl ring, contains at least one atom.

Structure Alpha and Examples:

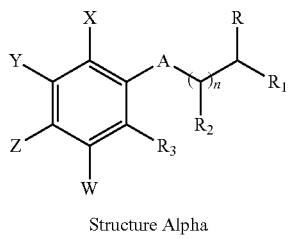

Structure Alpha

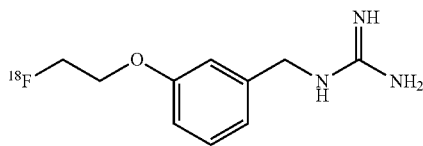

A = absent
n = 0
Im = $^{18}F$

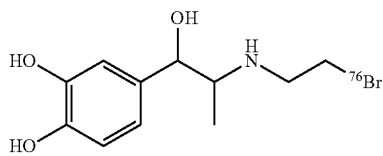

A = absent
n = 1
Im = $^{76}Br$

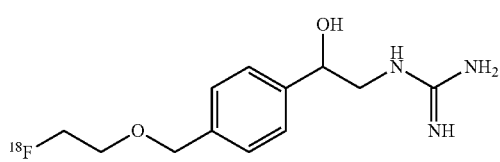

A = absent
n = 1
Im = $^{18}F$

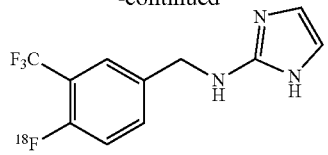

A = absent
n = 0
$R_4R_5 =$ —CH=CH—
Im = $^{18}F$

A further embodiment provides PET based radiotracers as illustrated in Structure Alpha and non-limiting Examples above, which in its simplest form may be considered a hybrid of structures I and II. In Structure Alpha n=0, 1, 2, 3 and A is O or absent. R, $R_1$, $R_2$ and $R_3$ are independently selected from the group consisting of H, $OR_4$, F, Cl, Br, I, $CF_3$, alkyl ($C_1$-$C_4$), aryl, heteroaryl, $C(=O)R_4$, $CO_2R_4$, $N(R_4)_2$, CN, $C(=NR_4)OR_5$, $NR_4C(=NR_5)NHR_6$, $C(=NR_4)NHR_5$, $C(=O)NHR_4$, $NR_4C(=O)NR_5$, $NR_4NR_5$, $SO_2OR_4$, and Im. The substituents W, X, Y and Z can independently be selected from the group consisting of H, $OR_4$, $N(R_4)_2$, F, Cl, Br, I, $CF_3$, Im, aryl, and heteroaryl. $R_4$, $R_5$, and $R_6$ are H, alkyl, aryl or heteroaryl substituents. In an alternative embodiment, any two of $R_4$, $R_5$, or $R_6$ may form a cyclic structure selected from the group consisting of —$CH_2$—$CH_2$—, —$CH_2$—$CH_2$—$CH_2$—, —CH=CH—, —X=CH—, and —X—CH=CH—, wherein X is O, NH, N=, or $NR_7$, and wherein $R_7$ is an alkyl, aryl or heteroaryl substituent. In a further alternative embodiment, the alkyl, aryl or heteroaryl substituents of $R_4$-$R_7$ may be substituted with various functional groups selected from the group consisting of but not limited to halogen (F, Cl, Br, I), OH, $NH_2$, COOH, Im, $COOR_8$, $CON(R_8)_2$, $SR_8$, $OR_8$, $NHC(=NH)NH_2$, $NHC(=O)NH_2$, $NHC(=O)N(R_8)_2$, $C(=NH)NH_2$, $C(=NR_8)N(R_8)_2$ and $N(R_8)_2$, in which $R_8$ may be hydrogen, alkyl, aryl or alkylaryl. The imaging moiety, Im, is selected from the group consisting of $^{18}F$, $^{76}Br$, $^{124}I$, $^{131}I$, $^{99m}Tc$, 153Gd, or 11In, and can be present in either W—Z or R-$R_7$.

Structure Beta and Examples:

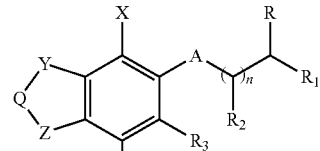

Structure Beta

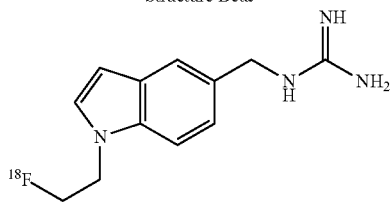

A = absent
n = 0
Y = —CH=CH—
Z = $NR_7$
Q = absent
Im = $^{18}F$

In yet a further embodiment, PET based radiotracers are described as illustrated in Structure Beta and non-limiting Examples above. In Structure Beta n=0, 1, 2, 3 and A=O or is absent. R, $R_1$, $R_2$ and $R_3$ are independently selected from the group consisting of H, $OR_4$, F, Cl, Br, I, $CF_3$, alkyl ($C_1$-$C_4$), aryl, heteroaryl, C(=O)$R_4$, $CO_2R_4$, N($R_4$)$_2$, CN, C(=N$R_4$)O$R_5$, $NR_4$(C(=N$R_5$)NH$R_6$, C(=N$R_4$)NH$R_5$, C(=O)NH$R_4$, $NR_4$C(=O)NR, $NR_4NR_5$, $SO_2OR_4$, and Im. The substituents W and X can independently be selected from the group consisting of H, $OR_4$, N($R_4$)$_2$, F, Cl, Br, I, $CF_3$, Im, aryl, and heteroaryl. Y and Z can be selected from the group consisting of CH, $CH_2$, O, N, $NR_7$, and CH=CH. Bridging group Q is absent or selected from the group consisting of CH, $CR_4$, $CH_2$, N, $NR_4$, NH, S, and O. $R_4$, $R_5$, and $R_6$ are H, alkyl, aryl or heteroaryl substituents. In an alternative embodiment, any two of $R_4$, $R_5$, or $R_6$ may form a cyclic structure selected from the group consisting of —$CH_2$—$CH_2$—, —$CH_2$—$CH_2$—$CH_2$—, —CH=CH—, —X=CH—, and —X—CH=CH—, wherein X is O, NH, N=, or $NR_7$, and wherein $R_7$ is an alkyl, aryl or heteroaryl substituents. In a further alternative embodiment, the alkyl, aryl or heteroaryl substituents of $R_4$-$R_7$ may substituted with various functional groups selected from the group consisting of but not limited to halogen (F, Cl, Br, I), OH, $NH_2$, COOH, Im, $COOR_8$, CON($R_8$)$_2$, $SR_8$, $OR_8$, NHC(=NH)$NH_2$, NHC(=O)$NH_2$, NHC(=O)N($R_8$)$_2$, C(=NH)$NH_2$, C(=$NR_8$)N($R_8$)$_2$ and N($R_8$)$_2$, in which $R_8$ may be hydrogen, alkyl, aryl or alkylaryl. The imaging moiety, Im, is selected from the group consisting of $^{18}$F, $^{76}$Br, $^{124}$I, $^{131}$I, $^{99m}$Tc, $^{153}$Gd, or $^{111}$In, and can be present in either W—Z or R-$R_7$.

Structure Chi:

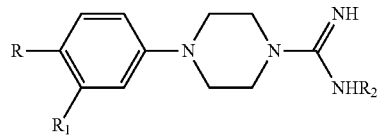

In an even further preferred embodiment, PET based radiotracers are described as illustrated in Structure Chi above. R through $R_2$ of Structure Chi are independently selected from the group consisting of H, $OR_3$, F, Cl, Br, I, $CH_2$F, OCH$_2$CH$_2$F, alkyl ($C_1$-$C_4$), aryl, heteroaryl, C(=O)$R_3$, $CO_2R_3$, and Im. Im is a imaging moiety and is selected from the group consisting of $^{18}$F, $^{76}$Br, $^{124}$I, and $^{131}$I. $R_3$ can be an H, alkyl, aryl or heteroaryl substituent. In an alternative embodiment the alkyl, aryl, aralkyl, alkylaryl or heteroaryl substituents of R-$R_3$ may be substituted with functional groups selected from the group consisting of but not limited to halogen (F, Cl, Br, I), OH, $NH_2$, COOH, Im, $COOR_4$, CON($R_4$)$_2$, $SR_4$, $OR_4$, NHC(=NH)$NH_2$, NHC(=O)$NH_2$, NHC(=O)N($R_4$)$_2$, C(=NH)$NH_2$, C(=$NR_4$)N($R_4$)$_2$ and N($R_4$)$_2$, in which $R_4$ may be hydrogen, alkyl, aryl or alkylaryl.

Structure Delta:

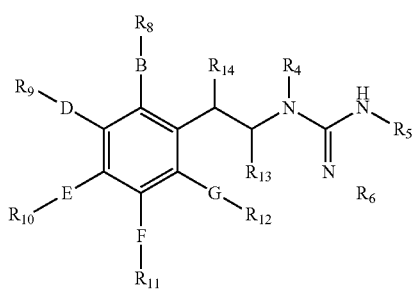

Structure Delta

A further embodiment describes PET based radiotracers as illustrated in Structure Delta above, wherein linking groups B, D, E, F and G are independently selected from the group consisting of a bond, alkyl ($C_1$-$C_5$; preferably $C_2$), aryl, aralkyl, alkylaryl, heteroaryl, alkoxy, alkylamino, aryloxy, and alkoxyalkyl. $R_8$ through $R_{14}$ are independently selected from the group consisting of H, $OR_3$, F, Cl, Br, I, $CH_2$F, OCH$_2$CH$_2$F, alkyl ($C_1$-$C_4$), aryl, heteroaryl, C(=O)$R_3$, $CO_2R_3$, and Im. $R_3$, $R_4$, $R_5$, and $R_6$ can independently be selected from the group consisting of H, alkyl, aryl, aralkyl, heteroaryl, alkylamino, alkyloxy, and aryloxy. In an alternative embodiment any two of $R_4$, $R_5$, $R_6$, $R_{13}$, or $R_{14}$ may form a cyclic structure selected from the group consisting of a bond, —$CH_2$—, —$CH_2$—$CH_2$—, —$CH_2$—$CH_2$—$CH_2$—, —CH=CH—, —X=CH—, and —X—CH=CH—, wherein X is O, NH, N=, or $NR_7$, and wherein $R_7$ is an alkyl, aryl or heteroaryl substituent. In a further alternative embodiment, the alkyl, aryl or heteroaryl substituents of $R_3$-$R_7$ may be substituted with various functional groups selected from the group consisting of but not limited to halogen (F, Cl, Br, I), OH, $NH_2$, COOH, Im, $COOR_{15}$, CON($R_{15}$)$_2$, $SR_{15}$, $OR_{15}$, NHC(=NH)$NH_2$, NHC(=O)$NH_2$, NHC(=O)N($R_{15}$)$_2$, C(=NH)$NH_2$, C(=$NR_{15}$)N($R_{15}$)$_2$ and N($R_{15}$)$_2$, wherein $R_{15}$ may be hydrogen, alkyl, aryl or alkylaryl. The imaging moiety, Im, can be selected from the group consisting of $^{18}$F, $^{76}$Br, $^{124}$I, $^{131}$I, $^{99m}$Tc, $^{153}$Gd, and $^{111}$In, and may be present in either W—Z or $R_4$-$R_7$. And, provided that in the case where any one of $R_8$-$R_{12}$ equals Im, the linking group B, D, E, F or G, which attaches the imaging moiety to the phenyl ring, contains at least one atom.

Structure Epsilon:

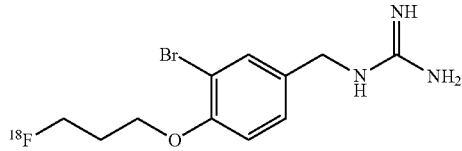 [SMILES: N=C(N)NCc1ccc(OCCC[18F])c(Br)c1]

A preferred embodiment describes the PET based radiotracer N-[3-bromo-4-(3-[$^{18}$F]fluoropropoxy)-benzyl]-guanidine hydrochloride, as illustrated in Structure Epsilon above. Structure Epsilon may be derived from Structure Alpha, wherein $R_1$, $R_3$, X and W are hydrogen, n is zero, R is guanidine (NHC(=NH)$NH_2$), Y is bromine and Z is OCH$_2$CH$_2$$^{18}$F.

Additional preferred compounds as part of the invention include the following:

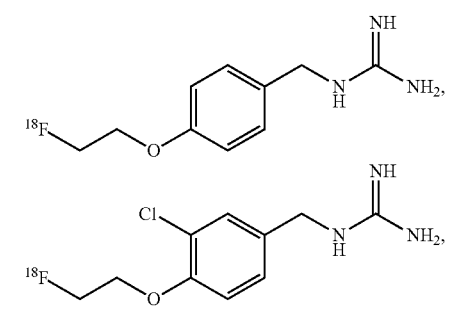

-continued

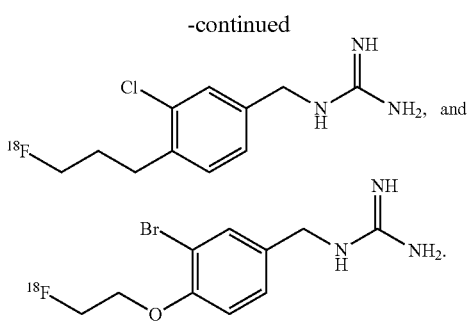

A further embodiment includes a method of imaging cardiac innervation comprising the steps of: administering an effective amount of one or more of the novel compounds herein set forth above, to a patient; detecting gamma radiation emitted by said compound; and forming an image therefrom. The method utilizes PET perfusion scanning or SPECT imaging techniques available to the skilled artisan, or other methods which may be employed.

There is also provided a composition useful in medical imaging which comprises one or more of the compounds hereinabove set forth, together with one or more excipients.

The compounds hereinabove described may be synthesized by methods available to the skilled artisan, which are in part further exemplified by the non-limiting Examples below.

EXAMPLES

The following examples are provided to demonstrate and further illustrate certain preferred embodiments of the present invention and are not to be construed as limiting the scope thereof.

General Experimental.

$^1$H NMR spectra were recorded on a Bruker Avance DRX 600 MHz spectrometer or on a Bruker Avance 300 MHz spectrometer. Chemical shifts are reported in ppm from tetramethylsilane with the residual solvent resonance resulting from incomplete deuteration as the internal standard (CDCl$_3$: δ 7.25 ppm, CD$_3$CN: δ 1.94 ppm, DMSO-d$_6$: δ 2.50 ppm). Data are reported as follows: chemical shift, multiplicity (s=singlet, d=doublet, t=triplet, q=quartet, quin=quintet, b or br=broad, m=multiplet), coupling constants, and integration. $^{13}$C NMR spectra were recorded on a Bruker Avance DRX 150 MHz or on a Bruker Avance 75 MHz spectrometer with complete proton decoupling. Chemical shifts are reported in ppm from tetramethylsilane with the solvent as the internal reference (CDCl$_3$: δ 77.0 ppm, CD$_3$CN: δ 118.1 ppm, DMSO-d$_6$: δ 39.5 ppm). $^{19}$F NMR spectra were recorded on a Bruker Avance DRX 565 MHz spectrometer. Chemical shifts are reported in ppm relative to an external standard (CCl$_3$F; δ=0.00 ppm). Low-resolution mass spectrometry was performed on an Agilent Technologies 1100 Series LC/MS EST-MS (positive mode). High-resolution mass spectrometry was performed on an Ionspec Ultima FTMS; ESI-MS (positive mode), or on an Agilent MSD-TOF; ESI-MS (positive mode). Melting points were determined using a Thomas-Hoover melting point apparatus and are uncorrected.

Unless otherwise stated, all reactions were conducted under an inert atmosphere of dry nitrogen. Indicated temperatures refer to those of the reaction bath, while ambient laboratory temperature is noted as 22° C. Anhydrous dimethylformamide (DMF), dimethylsulfoxide (DMSO), acetonitrile (McCN), pyridine, triethylamine (TEA), and diisopropylethylamine (DIEA) were obtained from Aldrich in SureSeal® bottles. Absolute ethanol was obtained from Quantum Chemical Corp. Merck silica gel, grade 9385, 230-400 mesh, 60 Å was used for flash chromatography. Ethyl acetate (EtOAc), chloroform (CHCl$_3$), methanol (MeOH), HPLC grade acetonitrile (MeCN), dichloromethane (DCM), ethyl ether, acetone, sodium hydroxide (NaOH), and hydrochloric acid (HCl) were obtained from Baker. 1-Trityl-1H-imidazole-2-amine was prepared according to a published procedure (U.S. Pat. No. 6,130,231, incorporated by reference in its entirety). 1-Bromo-2-fluoroethane was purchased from Alfa Aesar. 3-Methoxy-4-fluorobenzonitrile was purchased from TCI. MDCK cell membranes expressing human norepinephrine transporter, and [$^3$H]desipramine were purchased from Perkin-Elmer. [$^{18}$F]NaF was obtained from PETNET Pharmaceutical Services (Cummings Park, Woburn, Mass.) on a MP1 anion exchange resin (BioRad) cartridge. Other reagents were obtained from Lancaster Synthesis, Inc., Sigma-Aldrich Chemical Co, or Fluka Chemical Corp.

Example 1

Synthesis of N-(4-Fluoro-3-(trifluoromethyl)benzyl)-1H-imidazol-2-amine

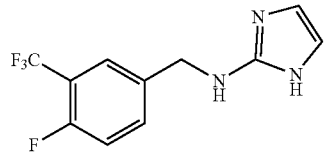 [SMILES: Fc1ccc(CNc2ncc[nH]2)cc1C(F)(F)F]

Part A—Preparation of N-(4-Fluoro-3-(trifluoromethyl)benzyl)-1-trityl-1H-imidazol-2-amine

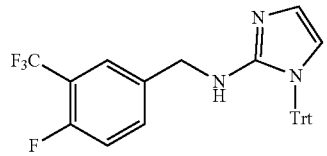

A solution of 4-fluoro-3-(trifluoromethyl)benzaldehyde (227 mg, 1.18 mmol) and 1-trityl-1H-imidazole-2-amine (462.3 mg, 1.42 mmol) in toluene (40 mL) was heated at reflux for 6 h while using a Dean-Stark apparatus to remove water. The mixture was cooled to room temperature, treated with sodium triacetoxyborohydride (1.00 g, 4.70 mmol), and stirred overnight. The reaction was quenched by the addition of water (150 mL), and the layers were separated. The aqueous layer was extracted with ethyl acetate (2×50 mL). The combined organic layers were dried (MgSO$_4$) and concentrated, and the resulting residue was purified by flash chromatography (40:60 EtOAc/hexanes) to yield the title compound as a pale yellow solid (266 mg, 45%). $^1$H NMR (CDCl$_3$, 300 MHz): δ 7.38-7.30 (m, 9H), 7.24-7.14 (m, 6H), 7.14-6.93 (m, 3H), 6.71 (d, J=3.0 Hz, 1H), 6.45 (d, J=3.0 Hz, 1H), 4.28 (d, J=6.0 Hz, 2H), 3.26 (t, J=6.0 Hz, 1H); $^{13}$C NMR (CDCl$_3$, 75 MHz): δ 158.69 (d, J=253.5), 149.54, 141.52, 135.56, 132.82 (d, J=8.2 Hz), 129.93, 128.16, 128.07, 125.86, 122.44, 118.19-117.60 (m), 117.30, 116.48 (d, J=20.25 Hz), 73.91, 46.54. MS (ESI): 243.2 (Trt carbocation, 100).

Part B—Preparation of N-(4-Fluoro-3-(trifluoromethyl)benzyl)-1H-imidazol-2-amine A solution of the product of Part A (150 mg, 0.30 mmol) in 5:95 triisopropylsilane/TFA (2.0 mL) was heated at 60° C. for 2 h, and concentrated. The residue was dissolved in DCM (20 mL) and washed with 5% Na₂CO₃ (10 mL). The organic layer was dried (Na₂SO₄) and concentrated. The resulting crude product was purified by flash chromatography (MeOH/DCM, 10/90-15/85) to yield the title compound as a light gray oil (49.7 mg, 64%). ¹H NMR (CDCl₃, 600 MHz): δ 7.51 (d, J=6.0 Hz, 1H), 7.50-7.46 (m, 1H), 7.10 (t, J=9.6 Hz, 1H), 6.57 (s, 2H), 5.31 (bs, 3H), 4.41 (s, 2H); ¹³C NMR (CDCl₃, 150 MHz): δ 159.21 (d, J=254.4), 149.86, 135.27, 132.82 (d, J=8.2 Hz), 126.04 (d, J=3.9 Hz), 122.69 (q, J=270.8 Hz), 119.02-118.36 (m), 117.55, 117.35 (d, J=20.7 Hz), 46.99; ¹⁹F NMR (CDCl₃, 565 MHz): δ −61.39 (d, J=12.4 Hz), −116.39 (t, J=6.2 Hz). MS (ESI): 260.2 (M+H, 100); HRMS calc'd for C₁₁H₁₀F₄N₃(M+H): 260.0805; Found: 260.0807.

Example 2

Synthesis of 1-(2-(4-(2-fluoroethoxy)phenyl)-2-hydroxyethyl)guanidinium Chloride

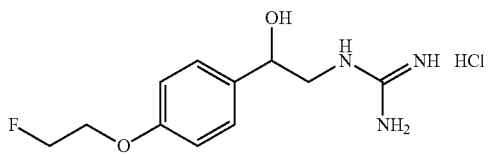 [SMILES: N=C(N)NCC(O)c1ccc(OCCF)cc1 ; Cl]

Part A—Preparation of 1-(2-Hydroxy-2-(4-hydroxyphenyl)ethyl)-2,3-bis(tert-butoxycarbonyl)guanidine

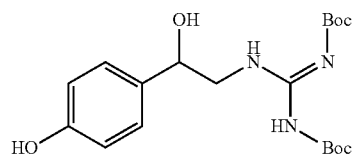 [SMILES: CC(C)(C)OC(=O)/N=C(\NCC(O)c1ccc(O)cc1)NC(=O)OC(C)(C)C]

A solution of (+/−)-octopamine hydrochloride (500 mg, 2.89 mmol) and N,N'-bis(Boc)-1H-pyrazole-1-carboxamidine (1.13 g, 3.60 mmol) in DMF (10 mL) was stirred for 1 h at ambient temperatures. The reaction mixture was concentrated, and the residue was dissolved in EtOAc (60 mL). The solution was washed with 1N KHSO₄ (2×30 mL) and 5% Na₂CO₃ (30 mL). The organic layer was dried (Na₂SO₄), concentrated, and purified by flash chromatography (EtOAc/hexane 30/70-50/50) to yield the title compound as a colorless solid (836 mg, 73%). ¹H NMR (CDCl₃, 600 MHz): δ 11.45 (bs, 1H), 8.76 (s, 1H), 7.15 (d, J=8.4 Hz, 2H), 6.77 (d, J=8.4 Hz, 2H), 6.52 (bs, 1H), 4.81-4.78 (m, 1H), 3.66-3.50 (m, 2H), 1.51 (s, 9H), 1.49 (s, 9H); ¹³C NMR (CDCl₃, 150 MHz): δ 162.86, 157.52, 156.04, 153.19, 133.52, 127.34, 115.65, 83.83, 80.07, 73.95, 49.49, 28.41, 28.26. MS (ESI): 396.4 (M+H, 100), 340.3 (M+H−tBu, 15).

Part B—Preparation 1-(2-(4-(2-Fluoroethoxy)phenyl)-2-hydroxyethyl)-2,3-bis(tert-butoxycarbonyl)guanidine

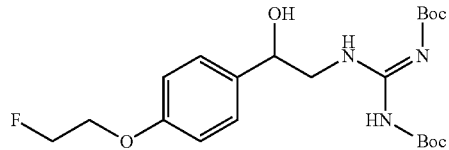 [SMILES: CC(C)(C)OC(=O)/N=C(\NCC(O)c1ccc(OCCF)cc1)NC(=O)OC(C)(C)C]

A mixture of the product of Part A (311 mg, 0.79 mmol), K₂CO₃ (163 mg, 1.18 mmol), KI (1.2 mg, 0.0070 mmol), and 2-bromofluoroethane (59 μL, 0.79 mmol) in DMSO (2.0 mL) was stirred at 50° C. for 3 h, followed by room temperature overnight. Water (15 mL) was added and the mixture was extracted with EtOAc (2×15 mL). The combined organic layers were washed with saturated NaCl (10 mL), dried (Na₂SO₄) and concentrated. The crude residue was purified with flash chromatography (EtOAc/hexane) to yield the title compound as a colorless solid (177 mg, 51%). ¹H NMR (DMSO-d₆, 300 MHz): δ 11.47 (s, 1H), 8.70 (s, 1H), 7.35-7.31 (m, 2H), 6.95-6.89 (m, 2H), 4.85-4.82 (m, 2H), 4.69-4.66 (m, 1H), 4.28-4.25 (m, 1H), 4.19-4.16 (m, 1H), 3.68-3.61 (m, 2H), 1.51 (s, 18H); ¹³C NMR (DMSO-d₆, 75 MHz): δ 162.91, 158.21, 157.73, 153.21, 135.18, 127.42, 114.85, 83.81, 82.13 (d, J=169.5 Hz), 79.96, 74.26, 67.42 (d, J=20.2 Hz), 49.82, 28.44, 28.25. MS (ESI): 464.1 (M+Na, 6), 442.1 (M+H, 100), 386.1 (M+H−tBu, 8).

Part C—Preparation of 1-(2-(4-(2-Fluoroethoxy)phenyl)-2-hydroxyethyl)guanidinium Chloride The product of Part B (15.0 mg, 0.034 mmol) was dissolved in a solution of dioxane (1.0 mL) and 37% aqueous HCl (4.0 mL), and allowed to stand at ambient temperature for 40 min. The mixture was concentrated and the resulting residue was purified by HPLC using a Phenomenex Luna C18(2) column (250×21.2 mm, 10μ, 100 Å) using a 0.72%/min gradient of 0-18% ACN containing 0.1% formic acid at a flow rate of 20 mL/min. Pure fractions were lyophilized to give a hygroscopic formate salt. This material was re-lyophilized from 0.5N HCl to give the title compound as a dry colorless solid (4.5 mg, 48%). ¹H NMR (1:1 CD₃CN/D₂O, 600 MHz): δ 7.31-7.27 (m, 2H), 6.95-6.92 (m, 2H), 4.74-4.73 (m, 2H), 4.69-4.66 (m, 1H), 4.25-4.17 (m, 2H), 3.34-3.28 (m, 2H); ¹³C NMR (1:1 CD₃CN/D₂O, 150 MHz): δ 159.01, 158.42, 134.89, 128.56, 115.70, 83.62 (d, J=164.4 Hz), 72.24, 68.44 (d, J=18.9 Hz), 49.31. MS (ESI): 224.3 (M+H−H₂O, 100); HRMS calc'd for C₁₁H₁₇FN₃O₂ (M+H): 242.1299; Found: 242.1297.

Example 3

Synthesis of 1-(4-(2-Fluoroethoxy)phenethyl)guanidinium Chloride

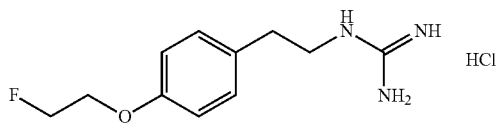 [SMILES: N=C(N)NCCc1ccc(OCCF)cc1 ; Cl]

The product of Example 2, Part B (88.4 mg, 0.20 mmol) was dissolved in a solution of TFA (1.9 mL), triisopropylsilane (0.05 mL), and water (0.05 mL). The reaction solution was heated at 55° C. for 10 min and concentrated. The crude mixture was purified by HPLC using the procedure of Example 2, Part B. The product fraction was lyophilized yielding a hygroscopic solid.

Relyophilization from 0.5N HCl gave the title compound as a dry colorless solid (12.4 mg, 24%). $^1$H NMR (1:1 CD$_3$CN/D$_2$O, 600 MHz): δ 7.18-7.14 (m, 2H), 6.90-6.87 (m, 2H), 4.75-4.65 (m, 2H), 4.22-4.15 (m, 2H), 3.31 (t, J=7.2 Hz, 2H), 2.76 (t, J=7.2 Hz, 2H); $^{13}$C NMR (1:1 CD$_3$CN/D$_2$O, 150 MHz): δ 158.08, 157.75, 132.00, 131.09, 115.82, 83.65 (d, J=164.6 Hz), 68.44 (d, J=18.8 Hz), 43.57, 34.36. HRMS calculated for C$_{11}$H$_{17}$FN$_3$O (M+H): 226.1350; Found: 226.1352.

Example 4

Synthesis of 4-(4-(2-Fluoroethoxy)phenyl)imidazolidin-2-iminium Chloride

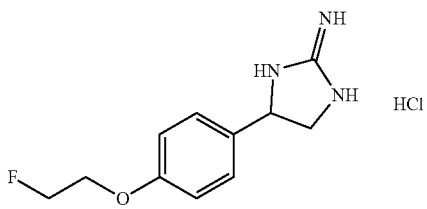 [SMILES: N=C1NCC(c2ccc(OCCF)cc2)N1 ; Cl]

Synthesis of the product of Example 3 also yielded the title compound as a colorless solid (14.2 mg, 27%). $^1$H NMR (1:1 CD$_3$CN/D$_2$O, 600 MHz): δ 7.29-7.26 (m, 2H), 6.98-6.94 (m, 2H), 5.03 (dd, J=7.8, 9.6 Hz, 1H), 4.78-4.66 (m, 2H), 4.26-4.18 (m, 2H), 4.00 (t, J=9.6 Hz, 1H), 3.41 (dd, J=7.2, 9.6 Hz, 1H); $^{13}$C NMR (1:1 CD$_3$CN/D$_2$O, 150 MHz): δ 160.52, 159.38, 133.73, 128.78, 116.04, 83.59 (d, J=164.7 Hz), 68.47 (d, J=18.8 Hz), 58.84, 52.07. HRMS calc'd for C$_{11}$H$_{15}$FN$_3$O (M+H): 224.1194; Found: 224.1197.

Example 5

Synthesis of (E)-1-(4-(2-Fluoroethoxy)styryl)guanidinium Chloride

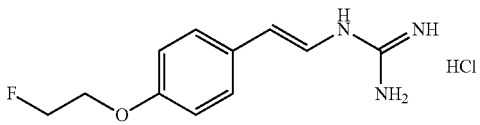 [SMILES: N=C(N)N/C=C/c1ccc(OCCF)cc1 ; Cl]

Synthesis of the product of Example 3 also yielded the title compound as a colorless solid (1.2 mg, 2.5%). $^1$H NMR (1:1 CD$_3$CN/D$_2$O, 600 MHz): δ 7.34-7.28 (m, 2H), 6.93-6.87 (m, 3H), 6.23 (d, J=14.4 Hz, 1H), 4.76-4.65 (m, 2H), 4.24-4.15 (m, 2H); $^{13}$C NMR (1:1 CD$_3$CN/D$_2$O, 150 MHz): δ 158.70, 155.21, 129.52, 128.20, 120.92, 117.08, 116.04, 83.58 (d, J=164.4 Hz), 68.46 (d, J=18.9 Hz). MS (ESI): 224.3 (M+H, 100).

Example 6

Synthesis of 5-(2-Amino-1-hydroxypropyl)-2-(2-fluoroethoxy)benzene-1,3-diol Hydrochloride

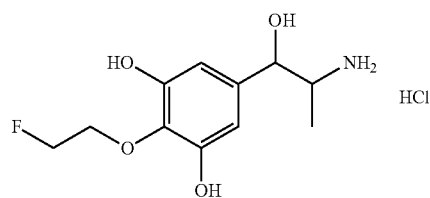 [SMILES: CC(N)C(O)c1cc(O)c(OCCF)c(O)c1 ; Cl]

Part A—Preparation of Methyl 4-(2-Fluoroethoxy)3,5-dihydroxybenzoate

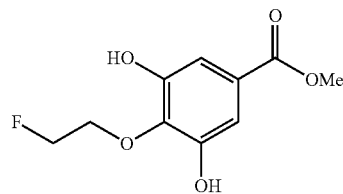 [SMILES: COC(=O)c1cc(O)c(OCCF)c(O)c1]

To a 100 mL round bottom flask was added methyl 3,4,5-trihydroxybenzoate (7.00 g, 88.0 mmol) followed by 25 mL of dimethyl sulfoxide. Potassium Carbonate (7.88 g, 57.0 mmol), potassium iodide (31.6 mg, 0.19 mmol) and 1-bromo-2-fluoroethane (5.79 g, 45.6 mmol) were successively added followed by 25 mL more of dimethyl sulfoxide. The reaction mixture was stirred for 18 h after which it was diluted by adding water (100 mL). The mixture was poured into a separatory funnel and extracted with DCM (3×40 mL). The organic layer was then washed with water (4×120 mL) and brine, and dried over magnesium sulfate. The organic layer was then concentrated to obtain an oil. The crude oil was purified using silica gel flash chromatography (DCM/ether 39:1) to obtain 1.9 g (22%) of the title compound (R$_f$~0.17 in 19:1 DCM/ether). $^1$H NMR (600 MHz, CDCl$_3$): δ 7.25 (s, 2H), 5.96 (s, 2H), 4.7 (t of d, 2H, J=48, 1.2 Hz), 4.37 (t of d, 2H, J=24, 1.2 Hz), 3.87 (s, 3H). $^{13}$C NMR (150 MHz, CDCl$_3$): δ 166.8, 149, 136.8, 126.4, 109.8, 82.16 (d, J=334 Hz), 72.6 (d, J=37.5), 52.3. MS (ESI): 231.4 (M+H, 100); HRMS: Calc'd for C$_{10}$H$_{11}$FO$_5$ (M+H): 231.06633; Found: 231.0664.

Part B—Preparation of Methyl 4-(2-Fluoroethoxy) 3,5-bis(methoxymethyloxy)benzoate

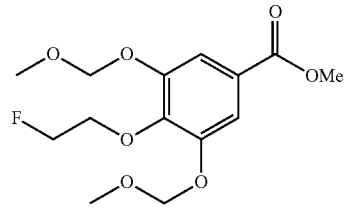 [SMILES: COCOc1cc(C(=O)OC)cc(OCOC)c1OCCF]

A flame dried 100 ml round bottom flask fitted with a reflux condenser was charged with sodium iodide (3.00 g, 20 mmol) and to this was added 1,2-dimethoxyethane (20 mL). Methoxymethyl chloride (2.09 g, 1.97 mL, 26.0 mmol) was then added drop-wise to this mixture. A colorless precipitate formed. This mixture was stirred for 5 min after which the product of Part A (1.5 g, 6.51 mmol) dissolved in dimethoxyethane (20 mL) was added to it. Diisopropylethylamine (3.36 g, 4.53 mL, 26.04 mmol) was added to the above mixture and the flask was immersed in an oil bath at 80° C. The resulting mixture was stirred at this temperature for 15 h after which it was cooled to room temperature. Water (20 mL) was added and the mixture was extracted with dichloromethane (2×40 mL). The combined organic layers were then washed with brine and dried over magnesium sulfate. Concentration of the organic layer in vacuo gave a pale red oil which was subjected to silica gel flash chromatography (hexanes/ether 4:1 to 7:3) to obtain 0.9 g (44%) of the product as a viscous oil. $^1$H NMR (600 MHz, CDCl$_3$): δ 7.5 (s, 2H), 5.25 (s, 4H), 4.7 (t of d, 2H, J=49, 1.2 Hz), 4.3 (d of t, 2H, J=24, 1.2 Hz), 3.88 (s, 3H), 3.5 (s, 6H). $^{13}$C NMR (150 MHz, CDCl$_3$): δ 166.3, 150.6, 142.9, 125.8, 112.1, 95.4, 82.61 (d, J=339 Hz), 72.3 (d, J=40.5 Hz), 56.4, 52.2. HRMS: Calc'd for $C_{14}H_{19}FO_7$ (M+H): 319.1187; Found: 319.1185.

Part C—Preparation of 4-(2-Fluoroethoxy)-3,5-bis(methoxymethyloxy)-benzaldehyde

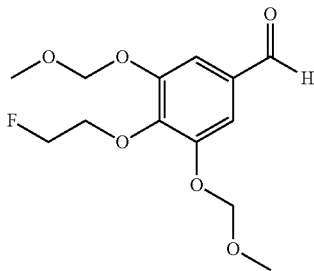 [SMILES: COCOc1cc(C=O)cc(OCOC)c1OCCF]

To a flame dried 50 ml round bottom flask was added a solution of Red-Al (3.29 mL; 65 wt % solution in toluene). Toluene (10 mL) was added to the flask and the solution was cooled to 0° C. in an ice bath. Morpholine (1.01 g, 1.01 mL, 11.6 mmol) was added drop-wise to keep the gas evolution under control. After completion of addition the mixture was stirred until gas evolution ceased (~15-20 min). This solution was added to a solution of the product of Part B (0.6 g, 1.88 mmol) in toluene (20 mL) at −50° C. via a cannula. A precipitate formed in the flask. The mixture was allowed to warm to −30° C. and stirred at this temperature for 3 h. Water (15 mL) was added drop-wise to the flask to quench the reaction and the solution was extracted with ether (2×30 mL). The organic layer was washed with brine and dried over magnesium sulfate. Concentration in vacuo gave a crude oil which was purified by silica gel flash chromatography (hexanes/ether 3:2 to 1:1) to obtain 420 mg (77%) of the title compound as an oil. $^1$H NMR (600 MHz, CDCl$_3$): δ 9.8 (s, 1H), 7.37 (s, 1H), 5.24 (s, 4H), 4.7 (t of d, 2H, J=49, 1.2 Hz), 4.3 (d of t, 2H, J=24, 1.2 Hz), 3.51 (s, 6H). $^{13}$C NMR (150 MHz, CDCl$_3$): δ 190.7, 151.4, 144.2, 132.3, 111.9, 104.2, 95.5, 82.61 (d, J=169 Hz), 72.3 (d, J=20.1 Hz), 56.4. HRMS: Calculated for $C_{13}H_{17}FO_6$ (M+H): 218.1081; Found: 289.1082.

Part D—Preparation of 1-(4-(2-Fluoroethoxy)-3,5-bis(methoxymethoxy)-phenyl)-2-nitropropan-1-ol

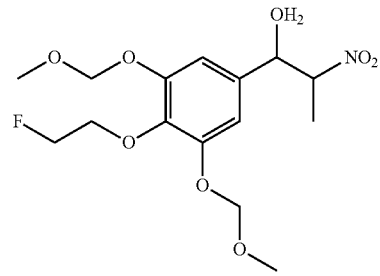 [SMILES: COCOc1cc(C(O)C(C)[N+](=O)[O-])cc(OCOC)c1OCCF]

A flame dried 15 mL round bottom flask was charged with product from Part C (270 mg, 0.93 mmol) and to this was added nitroethane (5 mL) and the solution was cooled to 0° C. Tetramethylguanidine (4 drops as measured by a Pasteur pipette) was added to the above mixture and the contents were stirred for 90 min. The mixture was poured into a separatory funnel containing water (5 mL) and extracted with ethyl acetate (2×15 mL). The organic layer was washed with brine and dried over magnesium sulfate. Concentration in vacuo gave a crude oil which was purified by silica gel flash chromatography (hexanes/ether 3:2) to obtain 130 mg (18%) of the title compound as an oil in a 3:1 (A:B) mixture of diastereomers. The OH proton in pair B and both the CHNO$_2$ protons in pair A were heavily overlaid with other signals causing ambiguity and are hence not reported. Pair A: $^1$H NMR (600 MHz, CDCl$_3$): δ 6.85 (s, 2H), 5.2 (s, 4H), 4.92 (d of d, 1H, J=4.2, 9 Hz), 4.7 (d of t, 2H, J=49, 1.2 Hz), 4.25 (d of t, 2H, J=24, 1.2 Hz), 3.5 (s, 6H), 2.5 (d, 1H, J=4.2 Hz), 1.35 (d, 3H, J=6.6 Hz). $^{13}$C NMR (150 MHz, CDCl$_3$): δ 151.4, 139.4, 134.3, 109.6, 95.6, 88.2, 82.64 (d, J=169 Hz), 76, 73.5, 72.3 (d, J=21 Hz), 56.3, 15.3. Pair B: $^1$H NMR (600 MHz, CDCl$_3$): δ 6.85 (s, 4H), 5.2 (s, 8H), 4.7 (d of t, 2H, J=49, 1.2 Hz), 4.25 (d of t, 2H, J=24, 1.2 Hz), 3.5 (s, 6H), 2.6 (d, 1H, J=3.6 Hz), 1.5 (d, 3H, J=7.2 Hz). $^{13}$C NMR (150 MHz, CDCl$_3$): δ 151.2, 138.9, 134.6, 108.8, 95.6, 87.2, 82.64 (d, J=169 Hz), 76, 73.5, 72.3 (d, J=21 Hz), 56.3, 12.2. HRMS: Calc'd for $C_{15}H_{22}FNO_8$ (M+Na): 386.1221; Found: 386.1220.

Part E—Preparation of 1-(4-(2-Fluoroethoxy)-3,5-bis(methoxymethoxy)phenyl)-1-hydroxypropan-2-aminium Trifluoroacetate

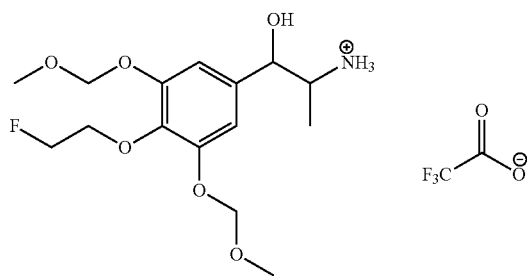 [SMILES: COCOc1cc(C(O)C(C)[NH3+])cc(OCOC)c1OCCF ; O=C([O-])C(F)(F)F]

The product of Part D (53 mg, 0.145 mmol) was charged to a flame dried 10 mL flask followed by methanol (1 mL). The flask was evacuated twice followed by purging with nitrogen. Pd—C(10 mg, 10 wt %) was added in one lot and the flask fitted with a hydrogen balloon. After stirring for one hour, ammonium formate (91 mg, 1.45 mmol) was added to the reaction followed by methanol (1 mL). The mixture was heated to reflux for 1 h and cooled to room temperature. The reaction mixture was filtered through a pad of Celite® and concentrated in vacuo to obtain a colorless solid. This crude solid was dissolved in water and subjected to preparative HPLC purification (Phenomenex Luna C18(2) column 10μ, 21.2×250 mm; gradient: 0-90% B over 30 min at 20 mL/min; Mobile phase A=0.1% TFA in water and B=0.1% TFA in 90% water) to obtain 10 mg (20%) of the title compound as a thick oil and as a diastereomeric mixture indistinguishable by NMR. $^1$H NMR (600 MHz, CD$_3$OD): δ 6.9 (s, 2H), 5.2 (s, 4H), 4.7 (d of t, 2H, J=49, 1.2 Hz), 4.25 (d of t, 2H, J=24, 1.2 Hz), 3.5 (s, 6H), 3.35 (m, 1H), 1.0 (d, 3H, J=6.6 Hz). $^{13}$C NMR (150 MHz, CD$_3$OD): δ 152.5, 140.6, 138.2, 110.8, 96.9, 84.1 (d, J=167 Hz), 76, 73.8 (d, J=21 Hz), 56.8, 54.6, 15.8. HRMS: Calc'd for C$_{15}$H$_{24}$FNO$_6$ (M+H): 334.1660; Found: 336.1662.

Part F—Preparation of 5-(2-Amino-1-hydroxypropyl)-2-(2-fluoroethoxy)-benzene-1,3-diol Hydrochloride To a flame dried 5 mL flask was added product of Part E (6 mg, 0.018 mmol) followed by methanol (1 mL). To this solution was added 2-3 drops of concentrated HCl and the solution was heated to reflux for 30 min. All solvent was removed in vacuo to obtain 3 mg (68%) of the title compound as a thick oil and as a mixture of diastereomers indistinguishable by NMR. $^1$H NMR (600 MHz, CD$_3$OD): δ 6.49 (s, 2H), 4.7 (d of t, 2H, J=49, 1.2 Hz), 4.31 (d, 1H, J=8.4 Hz), 4.25 (d of t, 2H, J=24, 1.2 Hz), 3.45 (m, 1H), 1.5 (m, 3H). HRMS: Calc'd for C$_{11}$H$_{16}$FNO$_4$ (M+H): 246.1136; Found: 246.1134.

Example 7

Synthesis of 3-Methoxy-4-fluorobenzylguanidinium Chloride

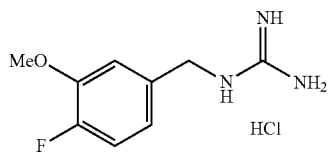 [SMILES: COc1cc(CNC(=N)N)ccc1F ; Cl]

Part A—Preparation of 3-Methoxy-4-fluorobenzylamine

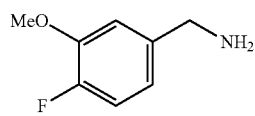 [SMILES: COc1cc(CN)ccc1F]

A flame dried 50 mL round bottom flask was charged with lithium aluminum hydride (0.63 g, 16.6 mmol) and to this was added tetrahydrofuran (25 mL). The solution was cooled to 0° C. and 3-methoxy-4-fluorobenzonitrile (1.0 g, 6.62 mmol) was added in one portion. The ice bath was removed after an hour and the resulting mixture was stirred for 16 h after which it was cooled to 0° C. and quenched by adding 0.63 mL water, 0.63 mL 15% NaOH and 1.89 mL water drop-wise and in succession. The mixture was stirred for 20 min and filtered. The filtrate was concentrated in vacuo to obtain 890 mg (86%) of the title compound as an oil. NMR indicated no further purification was required. $^1$H NMR (300 MHz, DMSO-d$_6$): δ 7.1 (m, 2H), 6.85 (m, 1H), 3.84 (s, 3H), 3.7 (s, 2H). $^{13}$C NMR (75 MHz, DMSO-d$_6$): δ 150.0 (d, J=240 Hz), 146.6 (d, J=10.5 Hz), 141.1 (d, J=3.75 Hz), 118.75 (d, J=6.75 Hz), 115.1 (d, J=18 Hz), 112.5, 55.75, 45.2. HRMS: Calc'd for C$_8$H$_{10}$FNO (M+H): 156.0819; Found: 156.0818.

Part B—Preparation of 3-Methoxy-4-fluorobenzyl-bis(tert-butoxycarbonyl)-guanidine

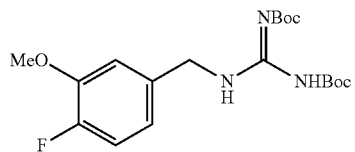

To a 10 mL flame dried flask was added the product of Part A (0.1 g, 0.644 mmol) and this was dissolved in MeCN. N,N-bis(tert-butoxycarbonyl)-1H-pyrazole-1-carboxamidine (0.2 g, 0.64 mmol) was added to the above solution and this was stirred for 30 min after which it was concentrated in vacuo to obtain a oil. This oil was purified by silica gel flash chromatography (dichloromethane) to obtain 0.22 g (86%) of the title compound as a colorless solid. $^1$H NMR (600 MHz, DMSO-d$_6$): δ 11.46 (s, 1H), 8.65 (t, 1H, J=5.4 Hz), 7.22 (d of d, 1H, J=8.4, 2.4 Hz), 7.15 (d of t, 1H, J=8.4, 3 Hz), 6.85 (m, 1H), 4.45 (d, 2H, J=6 Hz), 3.82 (s, 3H), 1.47 (s, 9H), 1.38 (s, 9H). $^{13}$C NMR (150 MHz, DMSO-d$_6$): δ 162.8, 155.1, 151.8, 149.8, 146.7 (d, J=10.6 Hz), 134.9, 119.5, 115.4 (d, J=18 Hz), 113.7, 82.8, 78.1, 55.7, 43.1, 27.8, 27.5. HRMS: Calc'd for C$_{19}$H$_{28}$FN$_3$O$_5$(M+H): 398.2085; Found: 398.2084.

Part C—Preparation of Preparation of 3-Methoxy-4-fluorobenzylguanidinium Chloride The product of Part B (0.06 g, 0.151 mmol) was charged to a 5 mL flame dried flask and to this was added dioxane (2 mL). Concentrated hydrochloric acid (0.5 mL) was added to the mixture and the solution was stirred at room temperature for 24 h. The reaction mixture was concentrated in vacuo, redissolved in 2 mL MeCN/water (1:1) mixture and lyophilized to obtain 35 mg (100%) of the product as the hydrochloride salt. $^1$H NMR (300 MHz, DMSO-d$_6$): δ 8.26 (t, 1H, J=6 Hz), 7.2 (m, 2H), 6.88 (m, 1H), 4.34 (d, 2H, J=6.6 Hz), 3.84 (s, 3H). $^{13}$C NMR (75 MHz, DMSO-d$_6$): δ 157, 152.4, 149.1, 147 (d, J=10.5 Hz), 133.9, 119.4 (d, J=6.75 Hz), 115.7 (d, J=18 Hz), 113.2, 55.9, 43.5. HRMS: Calc'd for C$_9$H$_{12}$FN$_3$O (M+H): 198.1037; Found: 198.1037.

Example 8

Synthesis of 3-Bromo-4-(2-fluoroethoxy)benzylguanidinium Chloride

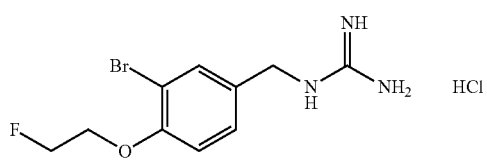 [SMILES: N=C(N)NCc1ccc(OCCF)c(Br)c1 ; Cl]

Part A—Preparation of 3-Bromo-4-(2-fluoroethoxy)benzonitrile

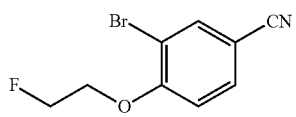 [SMILES: N#Cc1ccc(OCCF)c(Br)c1]

To a flame dried 50 mL round bottom flask was added 3-bromo-4-hydroxybenzonitrile (1.0 g, 5.05 mmol) followed by 5 mL of dimethyl sulfoxide. Potassium iodide (4.2 mg, 0.025 mmol) and potassium carbonate (1.05 g, 7.58 mmol) were added. The flask was immersed in an oil bath at 85° C. and 1-bromo-2-fluoroethane (0.769 g, 0.45 mL, 6.06 mmol) was added. The reaction was stirred at this temperature for 1 h after which it was cooled to room temperature and diluted with water (10 mL). The resulting solution was extracted with dichloromethane (2×20 mL). The organic layer was then washed with water (3×20 mL) and brine, and dried over magnesium sulfate. The solution was filtered and concentrated in vacuo to obtain an oil which was purified by silica gel flash chromatography using dichloromethane. Product (1.13 g, 92%) was obtained as a colorless solid. $^1$H NMR (600 MHz, CDCl$_3$): δ 7.83 (s, 1H), 7.57 (d of d, 1H, J=8.4, 1.8 Hz), 6.94 (d, 1H, J=8.4 Hz), 4.8 (t of d, 2H, J=49, 1.2 Hz), 4.35 (t of d, 2H, J=24, 1.2 Hz). 13C NMR (150 MHz, CDCl$_3$): δ 158.5, 136.9, 132.9, 117.5, 113, 106, 81.5 (d, J=171 Hz), 68.5 (d, J=21 Hz). HRMS: Calc'd for C$_9$H$_7$BrFNO (M+H): 243.9767; Found: 243.9767.

Part B—Preparation of 3-Bromo-4-(2-fluoroethoxy)benzylammonium Formate

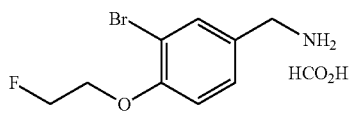

NiCl$_2$.6H$_2$O (180 mg, 0.758 mmol) was dried in a vacuum oven at 150° C. for 16 h to make anhydrous NiCl$_2$. This dried NiCl$_2$ was then charged to a flame-dried 15 mL two necked round bottom flask fitted with a reflux condenser. Anhydrous ethanol (2 mL) was added to the flask followed by the product from Part A (184 mg, 0.758 mmol) followed by sodium borohydride (86 mg, 2.27 mmol). Gas evolution was seen when sodium borohydride was added. After 90 min additional sodium borohydride (43 mg, 1.14 mmol) was added and the reaction mixture was stirred for an additional 10 min. The reaction mixture was filtered through a 0.2μ syringe filter, diluted with water (2.0 mL) and extracted with ethyl acetate (3×8 mL). The combined organic layers were washed with brine and dried over magnesium sulfate. The crude product obtained after concentration of the organic layer in vacuo was subjected to purification via preparative HPLC ((Phenomenex Luna C18(2) column 10μ, 21.2×250 mm; Mobile phase A=0.1% Formic acid in water and B=0.1% formic acid in 90% water at 20 mL/min) to obtain 38 mg (20%) of the product as the formate salt. $^1$H NMR (600 MHz, DMSO-d$_6$): δ 8.4 (s, 2H), 7.6 (s, 1H), 7.3 (m, 1H), 7.1 (m, 1H), 4.8 (d of t, 2H, J=48, 1.2 Hz), 4.3 (d of t, 2H, J=24, 1.2 Hz), 3.7 (m, 2H). HRMS: Calc'd for C$_9$H$_9$BrFO (M+H−NH$_3$): 230.9820; Found: 230.9821.

Part C—Preparation of 3-Bromo-4-(2-fluoroethoxy)benzyl-bis(tert-butoxycarbonyl)guanidine

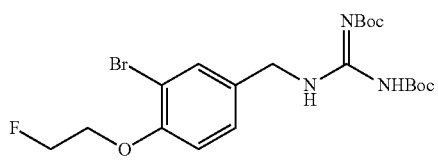

To a flame dried 10 mL round bottom flask was charged the product of Part B (30 mg, 0.102 mmol) and this was dissolved in MeCN (1.5 mL). Diisopropylethylamine (26.4 mg, 0.204 mmol) was then added to it followed by N,N-bis(tert-butoxycarbonyl)-1H-pyrazole-1-carboxamidine (31.7 mg, 0.102 mmol). The reaction mixture was stirred for 1 h after which it was concentrated and purified by silica gel flash chromatography using dichloromethane as eluant. The product (29 mg, 58%) was obtained as a sticky solid. $^1$H NMR (600 MHz, DMSO-d$_6$): δ 11.4 (s, 1H), 8.65 (t, 1H, J=6, 5.4 Hz), 7.58 (s, 1H), 7.28 (d of d, 1H, J=8.4, 1.8 Hz), 7.1 (d, 1H), 4.75 (d of t, 2H, J=48, 5.4, 1.2 Hz), 4.45 (d, 2H, J=6 Hz), 4.3 (d of t, 2H, J=24, 1.2 Hz), 1.47 (s, 9H), 1.39 (s, 9H). $^{13}$C NMR (150 MHz, CDCl$_3$): δ 162.8, 155.1, 153.5, 151.1, 132.3, 128.1, 113.9, 110.7, 82.8, 81.88 (d, J=166 Hz), 78.1, 68.25 (d, J=3.9 Hz), 42.3, 27.8, 27.5. HRMS: Calc'd for C$_{20}$H$_{29}$BrFN$_3$O$_5$(M+H): 490.1347; Found: 490.1349.

Part D—Preparation of 3-Bromo-4-(2-fluoroethoxy)benzylguanidinium Chloride

The product of Part C (23 mg, 0.046 mmol) was charged to a flame dried 10 mL round bottom flask and dissolved in dioxane (1.0 mL). Concentrated hydrochloric acid (1.0 mL) was added and the reaction was stirred for 16 h at ambient temperature. The reaction mixture was concentrated in vacuo, redissolved in 2 mL of MeCN/water (1:1), and lyophilized to obtain 15 mg (88%) of the product as the hydrochloride salt. $^1$H NMR (600 MHz, DMSO-d$_6$): δ 8.12 (t, 1H, J=6 Hz), 7.56 (d, 1H, J=2.4 Hz), 7.29 (d of d, 1H, J=8.7, 2.4 Hz), 7.15 (d, 1H, J=8.4 Hz), 4.75 (t of d, 2H, J=47.4, 4.2 Hz), 4.32 (t of d, J=30, 3.6 Hz), 4.31 (d, 2H, J=6.6 Hz). $^{13}$C NMR (150 MHz, CDCl$_3$): δ 158.8, 153.7, 131.9, 131.3, 127.9, 113.9, 110.9, 81.8 (d, J=166 Hz), 68.3

(d, J=18.9 Hz), 42.6. HRMS: Calc'd for $C_{10}H_{13}BrFN_3O$ (M+H): 290.0298; Found: 290.0298.

Example 9

Synthesis of 3-(2-Fluoroethoxy)benzylguanidinium Trifluoroacetate

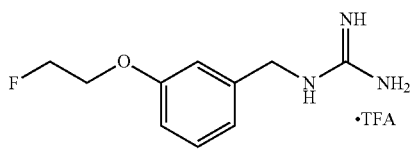 [SMILES: N=C(N)NCc1cccc(OCCF)c1]

Part A—Preparation of 3-(2-Fluoroethoxy)benzonitrile

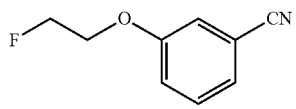 [SMILES: N#Cc1cccc(OCCF)c1]

To a flame dried 50 mL round bottom flask was added 3-cyanophenol (1.0 g, 8.39 mmol) followed by 10 mL dimethyl sulfoxide. Potassium iodide (7.0 mg, 0.042 mmol) and potassium carbonate (1.74 g, 12.6 mmol) were added. The flask was immersed in an oil bath at 85° C. and 1-bromo-2-fluoroethane (1.17 g, 0.686 mL, 9.23 mmol) was added. The reaction was stirred at this temperature for 30 min, cooled to room temperature, filtered, and the filtrate was diluted with water (100 mL). The resulting solution was extracted with dichloromethane (3×30 mL). The organic layer was then washed with water (5×20 mL) and brine, and dried over magnesium sulfate. The solution was filtered and concentrated in vacuo to obtain 1.31 g (94%) of an oil as the product. $^1$H NMR (600 MHz, CDCl$_3$): δ 7.37 (m, 1H), 7.26 (m, 1H), 7.15 (m, 2H), 4.75 (t of d, 2H, J=4.2, 46.8 Hz), 4.22 (t of d, 2H, J=4.2, 27.6 Hz). $^{13}$C NMR (75 MHz, CDCl$_3$): δ 158.4, 130.4, 125, 119.8, 117.9, 117.5, 113.3, 81 (d, J=171 Hz), 67.4 (d, J=10.1 Hz).

Part B—Preparation of 3-(2-Fluoroethoxy)benzylamine

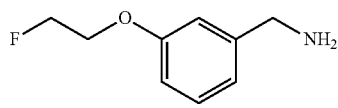 [SMILES: NCc1cccc(OCCF)c1]

Lithium aluminum hydride (0.67 g, 17.9 mmol) was charged to a flame dried 50 mL round bottom flask and the flask was cooled to 0° C. Tetrahydrofuran (14 mL) was added to the flask, followed by the product of Part A (1.18 g, 7.14 mmol). The ice bath was removed and the mixture stirred for 1.5 h, cooled to 0° C., and quenched by adding water (0.68 mL) and 15% NaOH (0.68 mL), followed by an addition of water (2.04 mL). This mixture was stirred for 20 min, filtered, and the filtrate was concentrated to afford 1.22 g (100%) of the product as an oil. This oil was pure by NMR. $^1$H NMR (300 MHz, CDCl$_3$): δ 7.25 (m, 1H), 6.9 (m, 2H), 6.8 (m, 1H), 4.75 (t of d, 2H, J=4.2, 47 Hz), 4.25 (t of d, 2H, J=4.2, 28 Hz), 3.8 (s, 2H). $^{13}$C NMR (75 MHz, CDCl$_3$): δ 158.6, 145.1, 129.5, 119.9, 113.3, 112.8, 81.9 (d, J=169 Hz), 67 (d, J=21 Hz), 46.3.

Part C—Preparation of 3-(2-Fluoroethoxy)benzyl bis(tert-butoxycarbonyl)guanidine

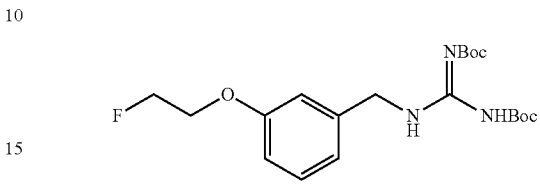

A 15 mL round bottom flask was flame dried and charged with the product of Part B (0.1 g, 0.59 mmol) and this was dissolved in MeCN (3.5 mL). N,N-bis(tert-butoxycarbonyl)-1H-pyrazole-1-carboxamidine (0.183 g, 0.591 mmol) was added, the solution was stirred for 90 min, and concentrated in vacuo to a oil. This crude oil was purified by silica gel flash chromatography using dichloromethane as eluant to give 199 mg (92%) of the product as a oil. $^1$H NMR (300 MHz, CDCl$_3$): δ 11.5 (br t, 1H), 8.4 (br t, 1H), 7.24 (d, 2H, J=9 Hz), 6.88 (d, 2H, J=9 Hz), 4.73 (t of d, 2H, J=6, 48 Hz), 4.54 (d, 2H, J=6 Hz), 4.2 (t of d, 2H, J=3, 27 Hz), 1.5 (s, 9H), 1.46 (s, 9H). $^{13}$C NMR (75 MHz, CDCl$_3$): δ 163.6, 157.9, 155.9, 153.1, 130, 129.2, 114.9, 83.1, 81.1 (d, J=169 Hz), 79.3, 67.1 (d, J=20 Hz), 44.4, 28.3, 28.

Part D—Preparation of 3-(2-Fluoroethoxy)benzylguanidinium Trifluoroacetate

The product of Part C (95 mg, 0.231 mmol) was charged to a flame dried 15 mL flask and dissolved in dioxane (0.5 mL). A solution of 4M HCl in dioxane (2.5 mL) was added followed by concentrated hydrochloric acid (0.5 mL). The reaction mixture was stirred for 16 h, and concentrated in vacuo to obtain a oil. This oil was purified by preparative HPLC (Phenomenex Luna C18(2) column 10μ, 21.2×250 mm; gradient: 0% B for 5 min then 0-30% B over 20 min at 20 mL/min; Mobile phase A=0.1% TFA in water and B=0.1% TFA in 90% water) to obtain 34 mg (52%) of the title compound. $^1$H NMR (600 MHz, CDCl$_3$+3 drops DMSO-d$_6$): δ 8.0 (t, 1H, J=6 Hz), 7.1 (t, 1H, 0.1=7.8 Hz), 6.85 (m, 2H), 6.76 (1H, d of d, 0.1=8.4, 1.8 Hz), 4.67 (t of d, 2H, J=4.2, 47.4 Hz), 4.31 (d, 2H, J=6 Hz), 4.16 (t of d, 2H, J=4.2, 28.8 Hz). HRMS: Calc'd for $C_{10}H_{14}FN_3O$ (M+H): 212.1193; Found: 212.1191.

Example 10

Synthesis of 3-Chloro-4-(2-fluoroethoxy)phenethylguanidinium Trifluoroacetate

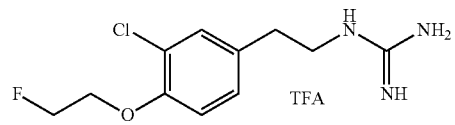 [SMILES: N=C(N)NCCc1ccc(OCCF)c(Cl)c1]

Part A—Preparation of 3-Chloro-4-hydroxyphenethylammonium Trifluoroacetate

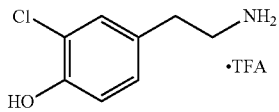 [SMILES: NCCc1ccc(O)c(Cl)c1]

To a 25 mL round bottom flask was added 3-chloro-4-methoxy phenethylamine hydrochloride and this was dissolved in hydrobromic acid (6.8 mL). The solution was heated to 110° C. for 5 h after which it was concentrated and dissolved in water (5 mL). The aqueous solution was purified by preparative HPLC (Phenomenex Luna C18(2) column 10μ, 21.2×250 mm; gradient: 0% B for 10 min then 0-30% B over 30 min at 20 mL/min; Mobile phase A=0.1% TFA in water and B=0.1% TFA in 90% water) to obtain 289 mg (51%) of the title compound. $^1$H NMR (600 MHz, DMSO-$d_6$): δ 10.1 (s, 1H), 7.8 (br, 3H), 7.23 (s, 1H), 7.01 (1H, d, J=8.4 Hz), 6.92 (d, 1H, J=8.4 Hz).

Part B—Preparation of N-(tert-Butoxycarbonyl)-3-chloro-4-hydroxyphenethylamine

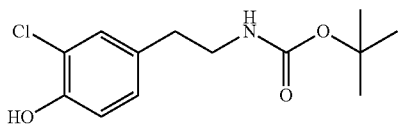 [SMILES: CC(C)(C)OC(=O)NCCc1ccc(O)c(Cl)c1]

To a flame dried 15 mL round bottom flask was added the product of Part A (97 mg, 0.34 mmol), followed by a mixture of dimethylformamide and dichloromethane (4 mL; 1:1) to dissolve it. Diisopropylethylamine (87.9 mg, 0.118 mL, 0.68 mmol) and di-tert-butyl dicarbonate (89 mg, 0.408 mmol) were then added successively and the mixture was stirred for 30 min. The reaction mixture was concentrated in vacuo and the crude oil subjected to silica gel flash chromatography in dichloromethane to give 72 mg (78%) of the product. $^1$H NMR (600 MHz, DMSO-$d_6$): δ 9.85 (s, 1H), 7.12 (s, 1H), 6.93 (d, 1H, J=8.4 Hz), 6.86 (m, 1H), 6.79 (br t, 1H), 3.075 (q, 2H, J=6.6 Hz), 2.57 (t, 2H, J=7.2 Hz), 1.35 (s, 9H).

Part C—Preparation of 3-Chloro-4-(2-fluoroethoxy)phenethylammonium Trifluoroacetate

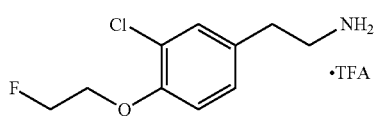 [SMILES: NCCc1ccc(OCCF)c(Cl)c1]

Powdered sodium hydroxide (14.2 mg, 0.356 mmol) was placed in a 15 mL round bottom flask. The product of Part B (69 mg, 0.254 mmol) was added followed by dimethylsulfoxide (2.5 mL). The resulting mixture was stirred for 5 min after which 1-p-tosyloxy-2-fluoroethane (prepared according to literature reference: *J. Med. Chem.* 1980, 23, 985-990) was added, and the flask immersed in a preheated oil bath at 75° C. The reaction was stirred for 60 min after which it was cooled to room temperature and diluted with dichloromethane (10 mL). The organic layer washed with water (5×6 mL) and brine, dried over magnesium sulfate, and concentrated in vacuo to give 120 mg of an oil. This oil was added a solution of trifluoroacetic acid in dichloromethane (3.0 mL, 1:1) and the resulting solution was stirred for 60 min at ambient temperature. The reaction mixture was concentrated in vacuo and subjected to preparative HPLC (Phenomenex Luna C18(2) column 10μ, 21.2×250 mm; gradient: 10-40% B over 20 min at 20 mL/min; Mobile phase A=0.1% TFA in water and B=0.1% TFA in 90% water) to obtain 52 mg (62% for two steps) of the title compound. $^1$H NMR (600 MHz, DMSO-$d_6$): δ 7.8 (br, 2H), 7.36 (d, 1H, J=1.8 Hz), 7.19 (d of d, 1H, J=2.4, 8.4 Hz), 7.13 (d, 1H, J=8.4 Hz), 4.75 (t of d, 2H, J=4.2, 41.4 Hz), 4.32 (t of d, 2H, J=3.6, 32 Hz), 3.0 (br t, 2H), 2.8 (t, 2H, J=7.8 Hz). $^{13}$C NMR (150 MHz, DMSO-$d_6$): δ 152.3, 130.9, 130.1, 128.5, 121.4, 114.2, 81.9 (d, J=166 Hz), 68.2 (d, J=18.9 Hz). HRMS: Calc'd for $C_{10}H_{13}FClNO$ (M+H): 218.0742; Found: 218.0743.

Part D—Preparation of 3-Chloro-4-(2-fluoroethoxy)phenethylguanidinium Trifluoroacetate To a flame dried 5 mL flask was added product of Part C (47 mg, 0.142 mmol). To this was added MeCN (1.4 mL) and diisopropylethylamine (37 mg, 50 μL, 0.248 mmol), followed by N,N-bis(tert-butoxycarbonyl)-1H-pyrazole-1-carboxamidine (44 mg, 0.142 mmol). The solution was stirred for 90 min after which it was concentrated in vacuo to an oil. This oil was passed through a plug of silica gel and eluted with hexanes/DCM (1:1 to 1:2). The eluant was concentrated to obtain 64 mg (98%) of an oil. This oil was redissolved in trifluoroacetic acid (1 mL) and heated to 55° C. for 5 min after which it was concentrated and purified by preparative HPLC (Phenomenex Luna C18(2) column 10μ, 21.2×250 mm; gradient: 10-40% B over 20 min at 20 mL/min; Mobile phase A=0.1% TFA in water and B=0.1% TFA in 90% water) to obtain 37 mg (54% for last step) of the title compound. $^1$H NMR (600 MHz, DMSO-$d_6$): δ 7.56 (br t, 1H), 7.38 (d, 1H, J=2.4 Hz), 7.185 (d of d, 1H, J=2.4, 8.4 Hz), 7.15 (d, 1H, J=8.4 Hz), 4.75 (t of d, 2H, J=4.2, 48 Hz), 4.3 (t of d, 2H, J=3.6, 30 Hz), 3.6 (br, 2H), 3.33 (AB q, 2H, J=6.6 Hz), 2.72 (t, 2H, J=7.8 Hz). $^{13}$C NMR (150 MHz, DMSO-$d_6$): δ 156.6, 152.1, 132., 130.2, 128.5, 121.2, 117.9, 114, 81.9 (d, J=165.9 Hz), 68.21 (d, J=18.75 Hz), 41.8, 33.1. HRMS: Calc'd for $C_{11}H_{15}ClFN_3O$ (M+H): 260.0960; Found: 260.0962.

Example 11

Synthesis of 1-(4-Fluoro-3-hydroxyphenyl)-1-hydroxy-N-methylpropan-2-aminium Trifluoroacetate

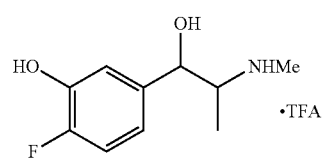

Part A—Preparation of
1-(4-Fluoro-3-methoxyphenyl)-2-nitropropan-1-ol

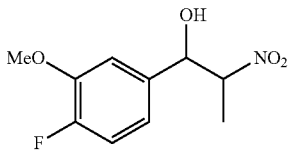 [SMILES: COc1cc(C(O)C(C)[N+](=O)[O-])ccc1F]

To a flame dried 100 mL round bottom flask was added 3-methoxy-4-fluorobenzaldehyde (367 mg, 2.38 mmol) and this was dissolved in methanol (23 mL). The reaction solution was cooled to 0° C. and nitroethane (357 mg, 4.76 mmol) was added to it followed by 5M NaOH (0.476 mL, 2.38 mmol). The solution was stirred for 80 min at 0° C. after which acetic acid (2% solution, 32 mL) was added and stirred for an additional 30 min. The reaction mixture was concentrated and water (10 mL) was added. The solution was extracted with dichloromethane (4×20 mL). The combined organic layers were washed with brine, dried over magnesium sulfate, and concentration to give afford an oil which was purified by silica gel flash chromatography using dichloromethane as eluant. Product (391 mg, 72%) product was obtained as a colorless oil in a 1.88:1 ratio (A:B) of diastereorners. Pair A: $^1$H NMR (600 MHz, CDCl$_3$): δ 7.07 (m, 1H), 7.0 (m, 1H), 6.8 (m, 1H), 5.34 (t, 1H, J=3 Hz), 4.65 (d of q, 1H, J=3.6, 6.6 Hz), 3.9 (s, 3H), 2.697 (d, 1H, J=3.6 Hz), 1.5 (d, 3H, J=6.6 Hz). $^{13}$C NMR (75 MHz, CDCl$_3$): δ 153.3, 150.1, 147.44 (d, J=10.8 Hz), 134.1, 117.7 (d, J=7 Hz), 115.7 (d, J=18.6 Hz), 110.6, 86.8, 72.8, 55.8, 11.7. Pair B: $^1$H NMR (600 MHz, CDCl$_3$): δ 7.07 (m, 1H), 7.0 (m, 1H), 6.8 (m, 1H), 4.9 (d of d, 1H, J=3.6, 9 Hz), 4.72 (m, 1H), 3.9 (s, 3H), 2.57 (d, 1H, J=4.2 Hz), 1.33 (d, 3H, J=5.4 Hz). $^{13}$C NMR (75 MHz, CDCl$_3$): δ 153.8, 150.5, 147.76 (d, J=10.8 Hz), 134.1, 119 (d, J=7 Hz), 115.8 (d, J=18.6 Hz), 111, 87.7, 75.3, 55.8, 15.9. HRMS: Calc'd for C$_{10}$H$_{12}$FNO$_4$ (M+Na): 252.0642; Found: 252.0643.

Part B—Preparation of
1-(4-Fluoro-3-methoxyphenyl)-2-aminopropan-1-ol

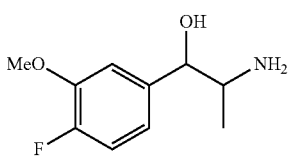

The product of Part A (301 mg, 1.31 mmol) was dissolved in a mixture of tetrahydrofuran and methanol (13 mL, 1:1) in a 50 mL flame dried round bottom flask. To this solution was added Pd—C(10 wt %, 69.7 mg, 0.065 mmol) followed by ammonium formate (413 mg, 6.55 mmol). The reaction solution was stirred at ambient temperature for 20 h after which an additional 413 mg ammonium formate and 70 mg Pd—C catalyst were added. The reaction mixture was stirred an additional 3 h after which it was filtered through a pad of Celite® and the filtrate concentrated in vacuo to obtain an oil. This oil was subjected to silica gel flash chromatography (DCM/MeOH/aqueous ammonia 8.9:1:0.1) to obtain 115 mg (44%) of the product as an oil in a 2:1 (A:B) mixture of diastereomers. Pair A: $^1$H NMR (600 MHz, DMSO-d$_6$): δ 7.0 (m, 2H), 6.84 (m, 1H), 4.1 (d, 1H, J=6.6 Hz), 3.82 (s, 3H), 2.79 (dddd, 1H, J=6.6 Hz), 0.79 (d, 3H, J=6.6 Hz). $^{13}$C NMR (150 MHz, CDCl$_3$): δ 151.2, 149.6, 146.4, 140.7, 118.65, 114.75, 112, 77.8, 55.8, 52.6, 19.3. Pair B: $^1$H NMR (600 MHz, DMSO-d$_6$): δ 7.0 (m, 2H), 6.84 (m, 1H), 4.28 (d, 1H, J=6.6 Hz), 3.82 (s, 3H), 2.87 (dddd, 1H, J=6.6 Hz), 0.85 (d, 3H, J=6.6 Hz). $^{13}$C NMR (150 MHz, CDCl$_3$): δ 151.2, 149.6, 146.4, 140.3, 118.65, 114.75, 112, 77.0, 55.8, 52.1, 18.1. HRMS: Calc'd for C$_{10}$H$_{14}$FNO$_2$ (M+H): 200.1081; Found: 200.1078.

Part C—Preparation of 1-(4-Fluoro-3-methoxyphenyl)-2-(methylamino)propan-1-ol

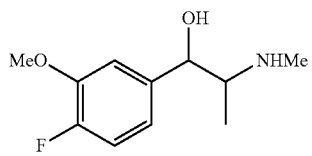

The product of Part B (101 mg, 0.507 mmol) was dissolved in ethyl formate (10 mL) in a flame dried 50 mL round bottom flask fitted with a reflux condenser. The solution was heated at 60° C. for 16 h, concentrated in vacuo, and the crude oil obtained was purified by silica gel flash chromatography (dichloromethane/methanol/ammonia 8.9:1:0.1) to yield 101 mg of the intermediate aldehyde. This aldehyde (50 mg, 0.22 mmol) was dissolved in tetrahydrofuran (5.0 mL) and added drop-wise to a solution of lithium aluminum hydride in tetrahydrofuran (1.27 mL of a 1.0M solution) at 0° C. The reaction was stirred at 0° C. for 30 min after which the bath was removed and the solution stirred at ambient temperature for 30 min and at reflux for 30 min. The reaction was then quenched by adding 59 µL water, 59 µL 15% NaOH and finally 0.2 mL water. The suspension was stirred for 20 min, filtered, and concentrated to an oil. This oil was subjected to purification using silica gel flash chromatography (dichloromethane/methanol/ammonia 8.9:1:0.1) to yield 38 mg (81%) of product as a 2.5:1 (A:B) mixture of diastereomers. Pair A: $^1$H NMR (300 MHz, DMSO-d$_6$): δ 7.11 (m, 2H), 6.85 (m, 1H), 4.21 (d, 1H, J=9 Hz), 3.83 (s, 3H), 2.57 (m, 1H), 2.29 (s, 3H), 0.71 (d, 3H, J=6 Hz). $^{13}$C NMR (75 MHz, DMSO-d$_6$): δ 152.1, 148.8, 146.47, 140.37 (d, J=3 Hz), 119.17 (d, J=6.75 Hz), 114.87, 112.2, 75.6, 60.5, 55.8, 33.3, 15.1. Pair B: $^1$H NMR (300 MHz, DMSO-d$_6$): δ 7.11 (m, 2H), 6.85 (m, 1H), 4.57 (d, 1H, J=6 Hz), 3.83 (s, 3H), 2.62 (m, 1H), 2.29 (s, 3H), 0.79 (d, 3H, J=6 Hz). $^{13}$C NMR (75 MHz, DMSO-d$_6$): δ 151.7, 148.5, 146.47, 140.6 (d, J=3 Hz), 118.29 (d, J=6.75 Hz), 114.87, 111.68, 72.7, 60.0, 55.8, 33.3, 13.95. HRMS: Calc'd for C$_{11}$H$_{16}$FNO$_2$ (M+H): 214.1237; Found: 214.1239.

Part D—Preparation of 1-(4-Fluoro-3-hydroxyphenyl)-1-hydroxy-N-methylpropan-2-aminium Trifluoroacetate To a flame dried 15 mL round bottom flask was added the product of Part C (30 mg, 0.141 mmol) and this was dissolved in dichloromethane (2.0 mL). The contents were cooled to −78° C. and a solution of boron tribromide (0.353 mL, 1.0M in DCM) was added drop-wise. The reaction mixture was stirred for 5 h after which it poured into a beaker containing cold water (2 mL) and stirred for another 1 hr. This mixture was then poured into a separatory funnel and the layers separated. The organic layer was washed with saturated sodium bicarbonate and extracted with 2M NaOH (3×5 mL). The combined NaOH solution was then acidified to pH 3 using 5N HCl and extracted with dichloromethane (3×10 mL). The aqueous layer was lyophilized to obtain a solid which was triturated with a MeCN/water mixture (10 mL, 1:1). This mixture was subjected to preparative HPLC ((Phenomenex Luna C18(2) column 10μ, 21.2×250 mm; gradient: 10% B for 10 min the 10-30% B over 20 min at 20 mL/min; Mobile phase A=0.1% TFA in water and B=0.1% TFA in 90% water) to obtain 20 mg (45%) of the title compound as a 2:1 (A:B) mixture of diastereomers. Pair A: $^1$H NMR (600 MHz, DMSO-$d_6$): δ 9.99 (s, 1H), 8.52 (br, 1H), 7.13 (m, 1H), 6.9 (m, 1H), 6.77 (m, 1H), 6.3 (d, 1H, J=3.6 Hz), 4.4 (d, 1H, J=6 Hz), 3.3 (br, 1H), 2.5 (s, 3H), 0.95 (d, 3H, J=6.6 Hz). $^{13}$C NMR (150 MHz, DMSO-$d_6$): δ 149.9, 144.75 (d, J=12.3 Hz), 137.5, 117.8, 116.2, 115.5, 72.6, 58, 48, 29, 11.9. Pair B: $^1$H NMR (600 MHz, DMSO-$d_6$): δ 9.90 (s, 1H), 8.38 (br, 1H), 7.13 (m, 1H), 6.9 (m, 1H), 6.77 (m, 1H), 6.1 (d, 1H, J=3.6 Hz), 4.9 (br t, 1H), 3.21 (br t, 1H), 2.59 (s, 3H), 0.91 (d, 3H, J=6.6 Hz). $^{13}$C NMR (150 MHz, DMSO-$d_6$): δ 149.3, 144.5 (d, J=12.3 Hz), 137.3, 116.4, 116.2, 115.5, 69, 58, 48, 30.4, 9.1. HRMS: Calc'd for $C_{10}H_{14}FNO_2$ (M+H): 200.1081; Found: 200.1081.

Example 12

Norepinephrine Transporter Binding Assay

Inhibitors to be tested were dissolved in incubation buffer (50 mM Tris-HCl, 10% sucrose, pH 7.4) at appropriate dilutions. The inhibitor solutions were added to the wells of a microtiter plate (40 μL/well) in triplicate. Each well of test agent (and appropriate control wells) was treated with a mixture of MDCK cell membrane preparation (22.4 μg of membrane) expressing human norepinephrine transporter (Bmax=3.7 pmol norepinephrine transporter/mg protein), and [$^3$H]desipramine (2 nM, 64.8 Ci/mmol) in a total volume of 0.2 mL. The resulting mixtures were incubated for 2 h on ice. A 96 well GF/C filter plate was presoaked with coating buffer (0.5% polyvinylpyrrolidine and 0.1% Tween 20) for 2 h at room temperature. The presoaked filter plate was washed with incubation buffer (6×0.2 mL). The NET reactions were transferred to the coated filter plate and filtered. The filter plate was washed (6×0.2 mL) with ice cold wash buffer (50 mM Tris-HCl, 0.9% NaCl, pH 7.4). The plate was dried overnight, incubated briefly with 25 μL scintillant, and read on a Micro Beta plate reader.

TABLE 1

NET Affinity of Examples 1-11

| Example # | NET Affinity, μM |
| --- | --- |
| 1 | 17.94 |
| 2 | <20 |
| 3 | 1.45 |
| 4 | 7.27 |
| 5 | 4.10 |
| 6 | 102.8 |
| 7 | 20.71 |
| 8 | 5.65 |
| 9 | 4.36 |
| 10 | 1.80 |
| 11 | 54.85 |

Examples 13-15

General Procedure for [$^{18}$F]Fluorination via [$^{18}$F]2-Fluoroethyl Tosylate Part A—Preparation of [$^{18}$F]2-Fluoroethyl Tosylate An MP1 anion exchange cartridge containing 1,000 mCi of [$^{18}$F]NaF was eluted with 0.20% aqueous $K_2CO_3$ (1.0 mL) into a 25 mL conical-bottomed silanized flask using an automated liquid handling system. The solution was evaporated by applying a gentle stream of heated $He_{(g)}$ and applied vacuum. The contents of the flask were reconstituted with 0.5 mL of MeCN, and the MeCN was removed by heated $He_{(g)}$ and applied vacuum to eliminate residual $H_2O$ (azeotropic evaporation). A separate 5 mL conical-bottomed Wheaton™ vial was used to prepared a solution of 4,7,13,16,21,24-hexaoxa-1,10-diazabicyclo[8.8.8]hexacosane (22.5 mg) (referred to as Kryptofix™ and henceforth abbreviated as $K_{222}$) and ethylene di-(p-toluenesulfonate) (3.0 mg) in MeCN (1.0 mL). The constituents of the vial were transferred to the 25 mL flask containing [$^{18}$F]KF, and the flask was positioned inside a microwave cavity (model 520 Resonance Instruments, Skokie, Ill.) and subjected to microwave radiation for 3 min at a power setting of 100 watts. The contents of the microwave reaction vial were filtered through an anion exchange resin to remove residual fluoride ion and collected in a conical-bottomed 5 mL Wheaton™ reaction vial.

Part B—[$^{18}$F]Fluorination Via [$^1$F]2-Fluoroethyl Tosylate

The product of Part A was transferred to a conical-bottomed 5 mL Wheaton™ reaction vial containing the product of either Example 8, Example 9 or Example 10 (4.0 mg) dissolved in anhydrous DMSO (300 μL). The contents of the vial were heated at 85° C. for 30 min and cooled to ambient temperatures. The solution was treated with TFA (1.5 mL) and stirred for 30 min at ambient temperature. The solution was transferred to a clean 25 mL pear-shaped flask and diluted with $H_2O$ (18.5 mL). The contents of the pear shaped flask were passed through a Sep Pak™ C18 cartridge and the cartridge was rinsed with $H_2O$ (5.0 mL). The desired product was eluted from the cartridge with MeCN (3.0 mL) into a conical-bottomed 5 mL Wheaton™ vial. The product solution was purified by HPLC using a Phenomenex LUNA C18(2) column (250×10 mm, 5 micron particle size, 100 Angstrom pore size) using a 5.0%/min gradient of 0-100% ACN containing 0.1% formic acid at a flow rate of 2.0 mL/min. The product eluted from the column in 13-14 min and was collected into a pear shaped flask. The solvent was evaporated with gentle heating under vacuum. The contents of the flask were reconstituted with 10% aqueous ethanol solution for biological experiments. The final product yield was ~50 mCi (not decay corrected). Radiochemical purity and decay corrected radiochemical yield data is shown in Table 2. Radiosynthesis and purification time was ~150 min.

TABLE 2

| | | Radiochemical Yield and Purity | |
|---|---|---|---|
| Example # | Cold Example # | Radiochemical Yield, % | Radiochemical Purity, % |
| 13 | 8 | 7.4 | 100 |
| 14 | 9 | 10.0 | 100 |
| 15 | 10 | 5.0 | 100 |

Example 16-22 Synthesis of Fluorinated Piperazines General Synthesis of Fluorinated CAAP Analogs

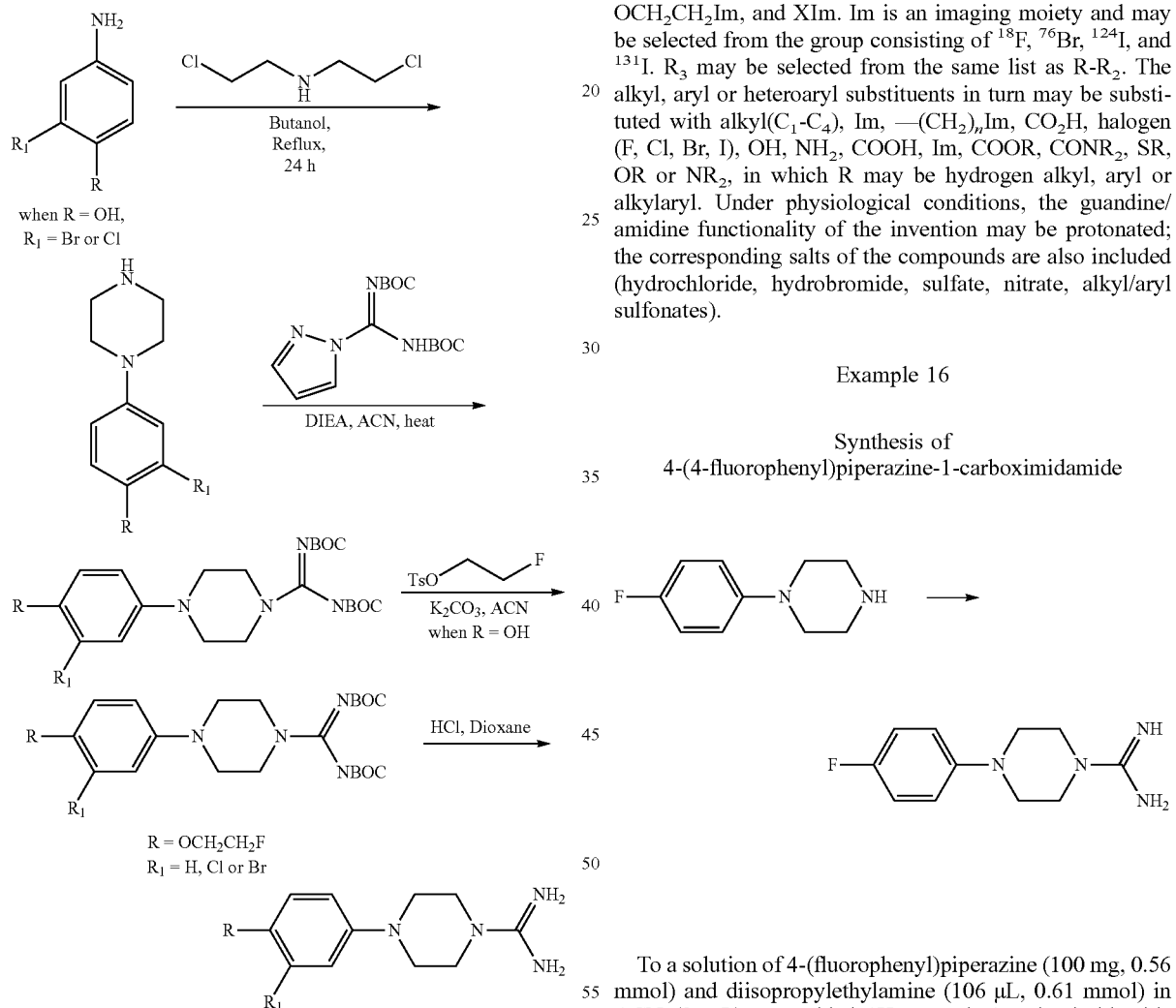

Substituted anilines can be alkylated with bis(2-chloroethyl)amine at elevated temperatures to yield the phenyl piperazine with the desired substitution pattern on the phenyl ring. The yield for this transformation is often moderate to low (<50% yield), however various phenyl piperazines are commercially available. Introduction of the guanidine moiety was carried out via alkylation of the piperazine moiety with N,N-'bis(tert-butoxycarbonyl-1H-pyrazole) 1-carbonxamidine. Deprotection of the guanidine functionality with HCl afforded the final compounds, which did not contain a fluoroethoxy moiety. For compounds where R is defined as a fluoroethoxy moiety alkylation of the hydroxyl precursor with fluoroethyl tosylate affords the desired substitution pattern. Typically $^{18}F$ compounds are made by the nucleophilic displacement of an appropriate leaving group, e.g., tosylate, mesylate, trifluoromethane sulfonate, nitro, trimethyl ammonium or a halide. Alternatively a cyclic sulfate or an epoxide may also be used as a leaving group. Typically these compounds are made from highly activated, dry $K^{18}F$, that is made "hotter" by the addition of cryptands such as krytofix[2.2.2]. Purification is generally via salt removal by reverse-phase chromatography (Sep-Pak).

R, $R_1$ and $R_2$ are independently selected from the list of H, $OR_3$, F, Cl, Br, I, $CH_2F$, $OCH_2CH_2F$, alkyl ($C_1$-$C_4$), aryl, heteroaryl, aralkyl, alkylarl, C(=O)$R_3$, $CO_2R_3$, Im, $OCH_2CH_2Im$, and XIm. Im is an imaging moiety and may be selected from the group consisting of $^{18}F$, $^{76}Br$, $^{124}I$, and $^{131}I$. $R_3$ may be selected from the same list as R-$R_2$. The alkyl, aryl or heteroaryl substituents in turn may be substituted with alkyl($C_1$-$C_4$), Im, —(CH$_2$)$_n$Im, $CO_2H$, halogen (F, Cl, Br, I), OH, $NH_2$, COOH, Im, COOR, $CONR_2$, SR, OR or $NR_2$, in which R may be hydrogen alkyl, aryl or alkylaryl. Under physiological conditions, the guandine/amidine functionality of the invention may be protonated; the corresponding salts of the compounds are also included (hydrochloride, hydrobromide, sulfate, nitrate, alkyl/aryl sulfonates).

Example 16

Synthesis of 4-(4-fluorophenyl)piperazine-1-carboximidamide

To a solution of 4-(fluorophenyl)piperazine (100 mg, 0.56 mmol) and diisopropylethylamine (106 µL, 0.61 mmol) in ACN (2 mL) was added 1H-pyrazole-1-carboximidamide hydrochloride (89 mg, 0.61 mmol). The reaction stirred at room temperature overnight. A precipitate formed, which was collected via filtration and washed with ACN to obtain 4-(4-fluorophenyl)piperazine-1-carboximidamide as a white solid (119 mg, 97% yield). $^1$H NMR (300 MHz, DMSO-d6): δ 7.77 (br s, 3H), 7.10-6.97 (m, 4H), 3.60 (dd, 4H, J=5.3, 4.7 Hz), 3.14 (dd, 4H, J=5.4, 4.7 Hz); $^{13}$C NMR (75.5 MHz, DMSO-d6): δ 157.9 (154.8), 156.3, 147.2, 118.0, 115.5 (115.2), 48.3, 44.7; $^{19}$F NMR (282.4 MHz, DMSO-d6): δ −124.70-124.78 (m, 1F); HRMS calcd for $C_{11}H_{15}FN_4$: 223.13535 found 223.1353.

Example 17

Synthesis of 4-(3-(fluoromethyl)phenyl)piperazine-1-carboximidamide

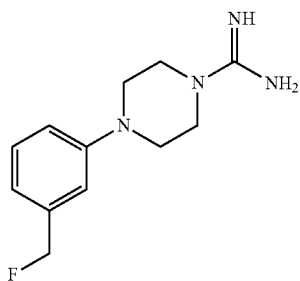 [SMILES: N=C(N)N1CCN(c2cccc(CF)c2)CC1]

Synthesis of 4-(3-hydroxymethyl-phenyl)-piperazine-1-carboxylic acid tert-butyl ester

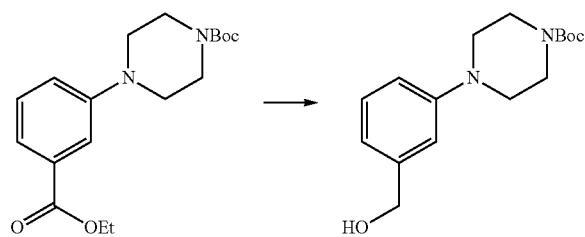 [SMILES: CCOC(=O)c1cccc(N2CCN(C(=O)OC(C)(C)C)CC2)c1 ; CC(C)(C)OC(=O)N1CCN(c2cccc(CO)c2)CC1]

To a solution of 4-(3-formyl-phenyl)-piperazine-1-carboxylic acid tert-butyl ester (2.0 g, 5.98 mmol) in THF (14 mL) at 0° C. was added LAH (6.0 mL, 1M solution in THF). The reaction mixture stirred at 0° C. for 30 min. followed by a quench of H$_2$O (239 μL), 15% NaOH (aq., 239 μL), and H$_2$O (718 μL). After completion of the additions the mixture stirred for 20 min. and was then filtered over a pad of celite. The solvent of the filtrate was removed en vacuo to obtain 4-(3-hydroxymethyl-phenyl)-piperazine-1-carboxylic acid tert-butyl ester as a brown solid (1.47 g, 84% yield), which was taken on to the next reaction without further purification. $^1$H NMR (300 MHz, DMSO-d6): δ 7.17 (t, 1H, J=8.0 Hz), 6.91 (br s, 1H), 6.82-6.76 (m, 2H), 5.06 (t, 1H, J=5.80 Hz), 4.44 (d, 2H, J=5.6 Hz), 3.45 (dd, 4H, J=5.5, 4.9 Hz), 3.08 (dd, 4H, J=5.3, 5.1 Hz), 1.42 (s, 9H).

Synthesis of tert-butyl 4-(3-fluoromethyl-phenyl)-piperazine-1-carboxylic acid tert-butyl ester

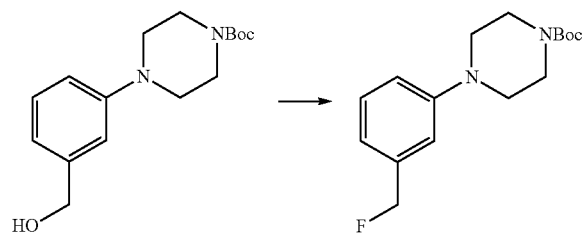 [SMILES: CC(C)(C)OC(=O)N1CCN(c2cccc(CO)c2)CC1 ; CC(C)(C)OC(=O)N1CCN(c2cccc(CF)c2)CC1]

To a solution of 4-(3-hydroxymethyl-phenyl)-piperazine-1-carboxylic acid tert-butyl ester (200 mg, 0.68 mmol), triethylamine (143 μL, 1.03 mmol), and tetramethylethylenediamine (10 μL, 0.07 mmol) in toluene (2 mL) at 0° C. was added methanesulfonyl chloride (79 μL, 1.03 mmol) drop-wise. After completion of addition the reaction mixture stirred at 0° C. for 40 min. EtOAc (5 mL) was added to the reaction mixture and the organic layer was separated, washed with brine, dried over Na$_2$SO$_4$, and concentrated to obtain 4-(3-(methanesulfonyloxymethyl-phenyl)-piperazine-1-carboxylic acid tert-butyl ester as a brown oil.

In a Wheaton vial TBAF (268 mg, 1.03 mmol) was added to a solution of crude 4-(3-(methanesulfonyloxymethyl-phenyl)-piperazine-1-carboxylic acid tert-butyl ester in ACN (2.3 mL). After completion of addition the reaction mixture was heated to 130° C. for 10 min. before being quenched with water (1.0 mL). The reaction mixture was extracted with EtOAc (3×5.0 mL) and the organic layers were washed with brine, dried over Na$_2$SO$_4$, and concentrated to obtain tert-butyl 4-(3-(fluoromethyl)phenyl)piperazine-1-carboxylate along with minor impurities (201.3 mg, 100% crude yield). $^1$H NMR (300 MHz, DMSO-d6): δ 7.29-7.24 (m, 1H), 6.99-6.94 (m, 2H), 6.86-6.84 (m, 1H), 5.34 (d, J=48 Hz, 2H), 3.47-3.44 (m, 4H), 3.13-3.10 (m, 4H), 1.42 (s, 9H).

Synthesis of 4-(3-(fluoromethyl)phenyl)piperazine-1-carboximidamide

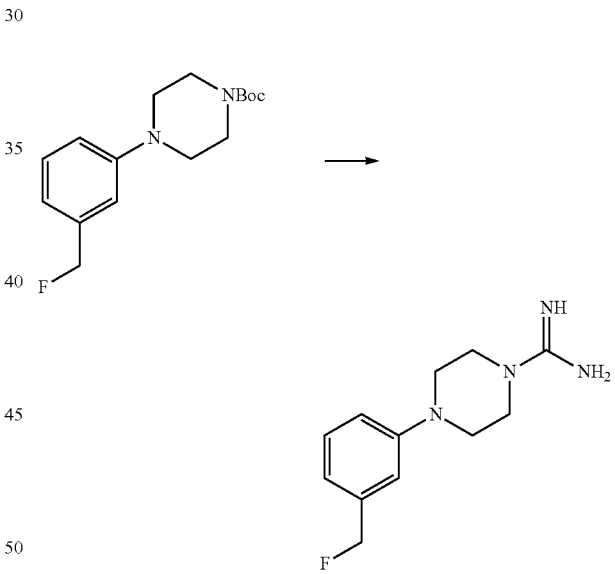

Tert-butyl 4-(3-(fluoromethyl)phenyl)piperazine-1-carboxylate (201.3 mg, mmol) was dissolved in a 4.0M solution of HCl and dioxane (2 mL) and stirred at room temperature. After 45 min. the reaction mixture was concentrated and re-dissolved in ACN (2 mL). Diisopropylethylamine (22 μL, 1.51 mmol) and 1H-pyrazole-1-carboximidamide (110 mg, 0.75 mmol) were added to the stirring reaction mixture. The next day, the reaction mixture was concentrated to yield a crude oil, which was purified by HPLC using a Phenomenex Luna C-18 (2) column (10μ, 250×21.2 mm, gradient method 0-100% B over 14 min., where B=90% ACN in water using 0.1% TFA as a modifier and A=water using 0.1% TFA as a modifier) with a flow rate of 20 mL/min to isolate 4-(3-(fluoromethyl)phenyl)piperazine-1-carboximidamide as a white solid (42.7 mg, 23% isolated yield over 4 steps). $^1$H NMR (300 MHz, DMSO-d6): δ 7.58 (br s, 3H), 7.28 (t, 1H, J=7.8 Hz), 7.01 (br s, 1H), 6.98 (br s, 1H), 6.87 (d, 1H, J=7.3 Hz), 5.35 (d, 2H, J=47.9 Hz), 3.58 (dd, 4H, J=5.4, 4.9 Hz), 3.26 (dd, 4H, J=5.4, 4.8 Hz); $^{13}$C NMR (75.5 MHz, DMSO-d6): δ 156.1, 150.3, 137.1 (136.8), 129.2, 118.8 (118.7), 115.9, 114.9 (114.8), 84.6 (83.4), 47.2, 44.7; HRMS calcd for $C_{12}H_{17}FN_4$: 237.15100 found 237.1514.

Example 18

Synthesis of 4-[4-(2-fluoro-ethoxy)-phenyl]-piperazine-1-carboxamidine

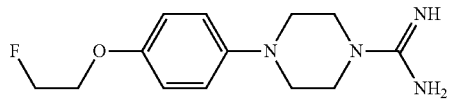 [SMILES: N=C(N)N1CCN(c2ccc(OCCF)cc2)CC1]

Synthesis of tert-butyl 4-(4-(2-fluoroethoxy)phenyl)piperazine-1-carboxylate

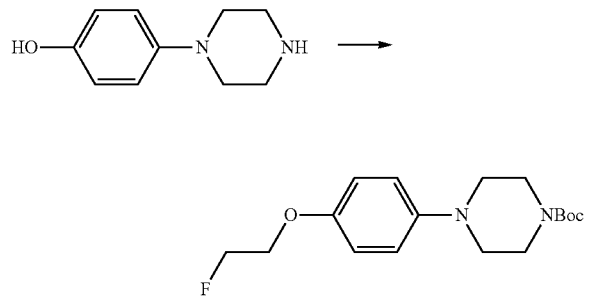

To a solution of 4-hydroxyphenylpiperazine (2.0 g, 11.22 mmol) in water (56 mL) was added NaOH (673 mg, 16.83 mmol) followed by di-tert-butyl dicarbonate (2.7 g, 12.34 mmol). The reaction mixture stirred at room temperature overnight. The next day, the reaction mixture was filtered to collect tert-butyl 4-(4-hydroxyphenyl)-piperazine-1-carboxylate as a tan solid (3.1 g, 99% yield), which was washed with water (50 mL) and taken on to the next step without further purification. $^1$H NMR (300 MHz, DMSO-d6): δ 6.79 (AA'BB', 2H, $J_{AB}$=9.1 Hz, $J_{AA'}$=2.4 Hz), 6.66 (AA'BB', 2H, $J_{AB}$=9.1 Hz, $J_{BB'}$=2.4 Hz), 3.43 (dd, 4H, J=5.3, 4.9 Hz), 2.88 (dd, 4H, J=5.2, 5.1 Hz), 1.41 (s, 9H); $^{13}$C NMR (75.5 MHz, DMSO-d6): δ 153.8, 151.4, 144.0, 118.5, 115.4, 78.8, 50.3, 28.0.

To a solution of tert-butyl 4-(4-hydroxyphenyl)-piperazine-1-carboxylate (1.0 g, 3.59 mmol) in DMSO (12 mL) was added potassium carbonate (745 mg, 5.39 mmol), potassium iodide (18 mg, 0.11 mmol) and 1-bromo-2-fluoroethane (294 μL, 3.95 mmol). The reaction stirred at 50° C. overnight. The next day, additional amounts of potassium carbonate (745 mg, 5.39 mmol), 1-bromo-2-fluoroethane (134 μL, 1.79 mmol), and potassium iodide (18 mg, 0.11 mmol) were added. The reaction mixture continued to stir at 50° C. After 5 h the reaction mixture was cooled to room temperature, quenched with water (10 mL), and extracted with EtOAc (3×50 mL). The combined organic layers were washed with water (100 mL), brine (50 mL), dried over Na$_2$SO$_4$, and concentrated to obtain a brown solid. The crude material was purified using silica gel chromatography (1:4 hexanes: EtOAc) to obtain tert-butyl 4-(4-(2-fluoroethoxy)phenyl)piperazine-1-carboxylate as a white solid (440 mg, 38% yield). $^1$H NMR (300 MHz, DMSO-d6): δ 6.92-6.84 (m, 4H), 4.78 (m, 1H), 4.62 (m, 1H), 4.20 (m, 1H), 4.10 (m, 1H), 3.45 (dd, 4H, J=5.2, 5.0 Hz), 2.96 (dd, 4H, J=5.3, 5.0 Hz), 1.42 (s, 9H); $^{19}$F NMR (282.4 MHz, DMSO-d6): δ −222.04 (m, 1F); $^{13}$C NMR (75.5 MHz, DMSO-d6): δ 153.8, 152.1, 145.5, 117.9, 115.1, 83.2 (81.1), 78.9, 67.4 (67.2), 49.7, 43.2, 28.0; HRMS calcd. for $C_{17}H_{25}FN_2O_3$: 325.19220 found 325.19230.

Synthesis of 4-[4-(2-fluoro-ethoxy)-phenyl]-piperazine-1-carboxamidine

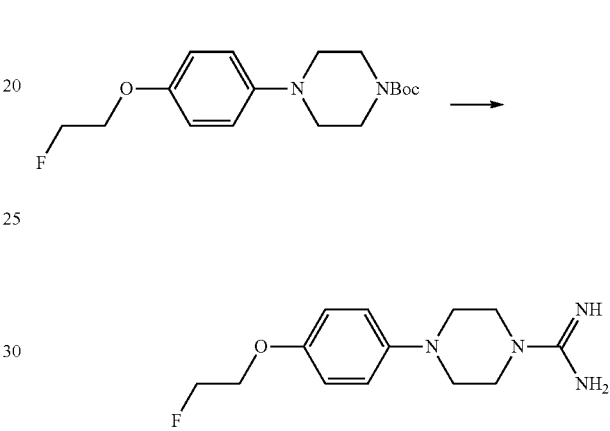

A solution of tert-butyl 4-(4-(2-fluoroethoxy)phenyl)piperazine-1-carboxylate (440 mg, 1.36 mmol) in 4.0M HCl in Dioxane (7 mL) stirred for 30 min. at room temperature. A precipitate formed, which was collected via filtration and washed with Dioxane to obtain the desired product as a white powder. The crude material was purified on the Prep HPLC using a 0-100% B over 14 min. method (% B=0.1% TFA in 90% ACN). The pure fractions were collected and lyophilized overnight to afford 1-(4-(2-fluoroethyl)phenyl)-piperazine as a white cake TFA salt (362 mg, 79% yield). $^1$H NMR (300 MHz, DMSO-d6): δ 9.00 (br s, 1H), 6.97-6.87 (m, 4H), 4.78 (m, 1H), 4.62 (m, 1H), 4.21 (m, 1H), 4.11 (m, 1H); 3.22 (s, 8H) $^{19}$F NMR (282.4 MHz, DMSO-d6): δ −222.07 (m, 1F); $^{13}$C NMR (75.5 MHz, DMSO-d6): 152.5, 144.5, 118.0, 115.2, 83.3 (81.1), 67.4 (67.2), 46.7, 42.8; HRMS calcd. for $C_{12}H_{17}FN_2O$: 225.13977 found: 225.13961.

To a solution of 1-(4-(2-fluoroethoxy)phenyl)piperazine (50 mg, 0.15 mmol) and diisopropylethylamine (59 μL, 0.34 mmol) in ACN (1 mL) was added 1H-pyrazole-1-carboximidamide (25 mg, 0.17 mmol). The reaction stirred at room temperature for 1 h, monitored by LC-MS. The precipitate was then filtered and washed with ACN to obtain the desired product as a white solid (33.8 mg, 58% yield). $^1$H NMR (300 MHz, DMSO-d6): δ 7.55 (br s, 3H), 6.95-6.86 (m, 4H), 4.78 (m, 1H), 4.62 (m, 1H), 4.21 (m, 1H), 4.11 (m, 1H), 3.57 (dd, 4H, J=5.2, 4.9 Hz), 3.09 (dd, 4H, J=5.1, 5.0 Hz); $^{19}$F NMR (DMSO-d6): δ −222.037 (m, 1F); $^{13}$C NMR (75.5 MHz, DMSO-d6): δ 156.0, 152.2, 144.9, 119.2, 115.1, 82.2 (81.1), 67.4 (67.2), 48.9, 44.9; HRMS calcd. for $C_{12}H_{17}FN_2O$: 267.16157 found 267.16146.

Example 19

Synthesis of 4-(3-chloro-4-(2-fluoroethoxy)phenyl)piperazine-1-carboximidamide

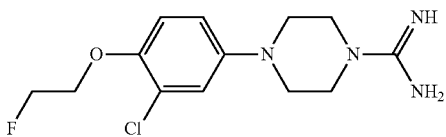

Synthesis of 4-(3-chloro-4-(2-fluoroethoxy)phenyl)piperazine-1-carboximidamide

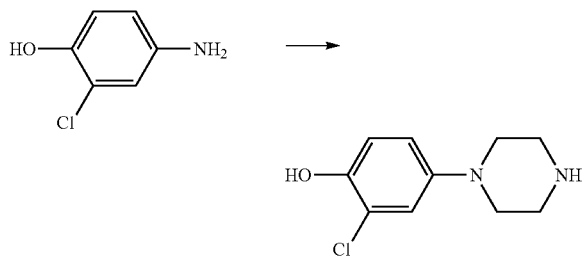

To a solution of 4-amino-2-chlorophenol (1.0 g, 6.97 mmol) in n-butanol (2 mL) was added bis(2-chloroethyl)amine hydrochloride (1.2 g, 6.97 mmol). After completion of addition the reaction mixture was heated at reflux for 60 h. Solid $Na_2CO_3$ (740 mg, 6.97 mmol) was added to the hot reaction mixture in one portion and the reaction mixture continued stirring at reflux. After 7 h the reaction mixture was cooled to RT and 2-chloro-4-(piperazin-1-yl)phenol was collected via filtration. The purple solid was washed with heptanes before proceeding to the next step without further purification (554 mg, 37% yield). $^1$H NMR (300 MHz, DMSO-d6): δ 6.95 (dd, 1H, J=2.8, 1.9 Hz), 6.91 (s, 1H), 6.81 (m, 1H), 3.21 (m, 4H), 3.16 (m, 4H).

Synthesis of tert-butyl (4-(3-chloro-4-hydroxyphenyl)piperazin-1-yl)methanediylidenedicarbamate

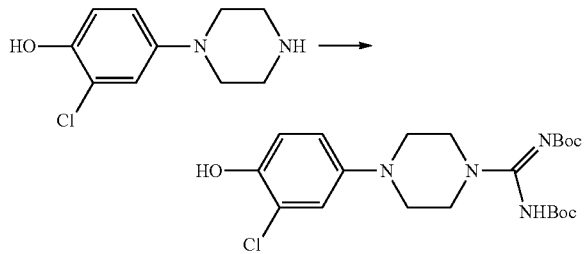

To a solution of 2-chloro-4-(piperazin-1-yl)phenol (200 mg, 0.94 mmol) and diisopropylethylamine (180 μL, 1.03 mmol) in DMF (3 mL) was added tert-butyl (1H-pyrazol-1-yl)methanediylidenedicarbamate (321 mg, 1.03 mmol). After stirring at room temperature for 1.5 h the reaction mixture was diluted with water (10 mL) and extracted with EtOAc (3×20 mL). The organic layers were separated and washed with brine, dried over $Na_2SO_4$, and concentrated to yield a crude oil. Purification of the crude material using silica gel chromatography (gradient of 20 to 100% EtOAc in hexanes) afforded tert-butyl (4-(3-chloro-4-hydroxyphenyl)piperazin-1-yl)methanediylidenedicarbamate as an oil, which crystallized upon standing (186 mg, 43% yield). $^1$H NMR (300 MHz, DMSO-d6): δ 9.61 (s, 1H), 9.48 (s, 1H), 6.91 (d, 1H, J=2.8 Hz), 6.86 (m, 1H), 6.79 (dd, 1H, J=8.9, 2.8 Hz), 3.50 (dd, 4H, J=5.2, 4.3 Hz), 2.99 (dd, 4H, J=5.0, 4.8 Hz), 1.42 (s, 9H), 1.37 (s, 9H); $^{13}$C NMR (75.5 MHz, DMSO-d6): δ 159.7, 151.2, 150.8, 146.6, 144.5, 119.8, 117.9, 116.9, 116.7, 80.1, 77.1, 49.2, 45.3, 27.9 (2C); HRMS calcd. for $C_{21}H_{31}ClN_4O_5$: 455.20557 found 455.20573.

Synthesis of tert-butyl (4-(3-chloro-4-(2-fluoroethoxy)phenyl)piperazin-1-yl)methanediylidenedicarbamate

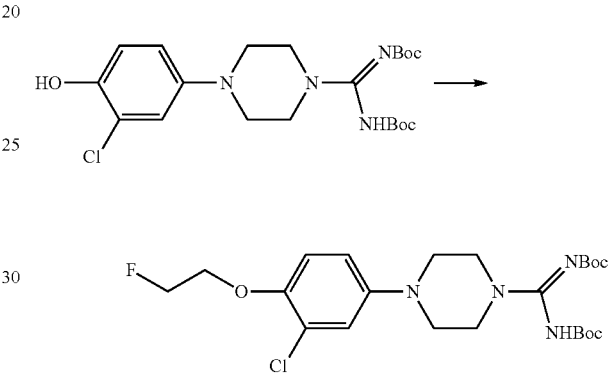

To a solution of Tert-butyl (4-(3-chloro-4-hydroxyphenyl)piperazin-1-yl)methanediylidenedicarbamate (182 mg, 0.40 mmol) in DMSO (4 mL) was added potassium carbonate (83 mg, 0.60 mmol), potassium iodide (3 mg, 0.02 mmol), and 1-bromo-2-fluoroethane (33 μL, 0.44 mmol). After completion of the additions the reaction mixture stirred at 50° C. After 4.5 h the reaction mixture was cooled to room temperature and quenched with water (10 mL). The aqueous layer was extracted with EtOAc (4×20 mL) and all combined organic layers were washed with water (50 mL), brine (50 mL), dried over $Na_2SO_4$, and concentrated to yield a crude oil.

Purification of the crude material via HPLC using a Phenomenex Luna C-18 (2) column (10μ, 250×21.2 mm, gradient method 40-80% B over 20 min., where B=90% ACN in water using 0.1% formic acid as a modifier and A=water using 0.1% formic acid as a modifier) with a flow rate of 20 mL/min to obtain tert-butyl (4-(3-chloro-4-(2-fluoroethoxy)phenyl)piperazin-1-yl)methanediylidenedicarbamate as a white solid (28.8 mg, 12% yield based on recovered starting material). $^1$H NMR (300 MHz, DMSO-d6): δ 9.62 (s, 1H), 7.06 (d, 1H, J=9.1 Hz), 7.04 (d, 1H, J=2.9 Hz), 6.89 (dd, 1H, J=9.0, 2.9 Hz), 4.75 (m, 1H), 4.67 (m, 1H), 4.25 (m, 1H), 4.20 (m, 1H), 3.51 (dd, 4H, J=6.1, 4.1 Hz), 3.08 (dd, 4H, J=5.1, 4.8 Hz), 1.42 (s, 9H), 1.37 (s, 9H); $^{19}$F NMR (282.4 MHz, DMSO-d6): δ −222.03 (m, 1F); $^{13}$C NMR (75.5 MHz, DMSO-d6): δ 159.7, 151.2, 150.7, 147.1, 145.9, 122.3, 117.9, 115.7, 115.6, 82.1 (81.6), 80.1, 77.1, 68.8 (68.7), 48.6, 45.1, 27.9 (2C) Minor rotomeric population is also visible; HRMS calcd. for $C_{23}H_{34}ClFN_4O_5$: 501.22745 found 501.2272.

Synthesis of 4-(3-chloro-4-(2-fluoroethoxy)phenyl)piperazine-1-carboximidamide

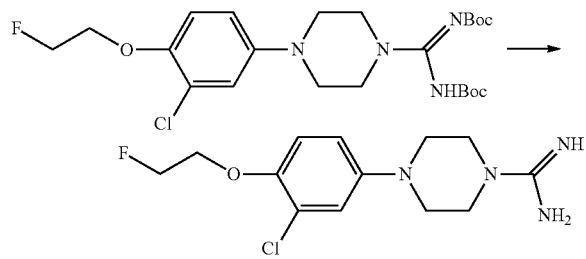

Tert-butyl (4-(3-chloro-4-(2-fluoroethoxy)phenyl)piperazin-1-yl)methanediylidenedicarbamate (26 mg, 0.05 mmol) was dissolved in a 4.0M solution of HCl in dioxane (0.5 mL) and stirred at room temperature overnight. The next day the reaction mixture was concentrated to yield a crude oil. Purification of the crude material via HPLC using a Phenomenex Luna C-18 (2) column (10μ, 250×21.2 mm, gradient method 0-100% B over 14 min., where B=90% ACN in water using 0.1% TFA as a modifier and A=water using 0.1% TFA as a modifier) with a flow rate of 20 mL/min afforded 4-(3-chloro-4-(2-fluoroethoxy)phenyl)piperazine-1-carboximidamide as a white solid (22 mg). $^1$H NMR (DMSO-d6): δ 7.53 (br s, 3H), 7.09 (d, 1H, J=2.8 Hz), 7.07 (d, 1H, J=8.1 Hz), 6.93 (dd, 1H, J=9.1, 2.9 Hz), 4.80 (m, 1H), 4.64 (m, 1H), 4.28 (m, 1H), 4.18 (m, 1H), 3.55 (dd, 4H, J=5.1, 4.9 Hz), 3.14 (dd, 4H, J=5.6, 4.4 Hz); $^{19}$F NMR (282.4 MHz, DMSO-d6): δ -222.03 (m, 1F); $^{13}$C NMR (75.5 MHz, DMSO-d6): δ 155.9, 147.2, 145.5, 122.3, 117.9, 115.8, 115.5, 82.7 (81.6), 68.8 (68.7), 48.1, 44.7; HRMS calcd. for $C_{13}H_{18}ClFN_4O$: 301.12259 found 301.1225.

Example 20

Synthesis of 4-(3-Bromo-4-(2-fluoroethoxy)phenyl)piperazine-1-carboximidamide

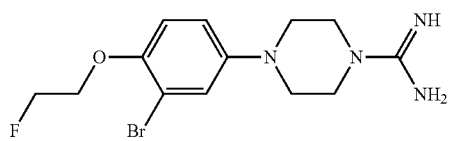 [SMILES: N=C(N)N1CCN(c2ccc(OCCF)c(Br)c2)CC1]

Synthesis of tert-butyl (4-(3-bromo-4-hydroxyphenyl)piperazin-1-yl)methanediylidenedicarbamate

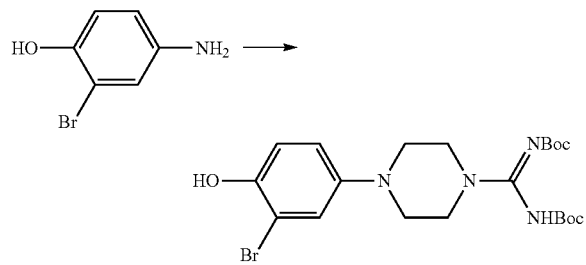

To a solution of the 4-amino-2-bromophenol (1.0 g, 5.32 mmol) in n-butanol (5 mL) was added bis(2-chloroethyl)amine hydrochloride (949 mg, 5.32 mmol). After completion of addition, the reaction mixture was heated at reflux for 60 h. Solid $Na_2CO_3$ (564 mg, 5.32 mmol) was added to the hot reaction mixture in one portion and the reaction mixture continued stirring at reflux. After 7 h the reaction mixture was cooled to RT and 2-bromo-4-(piperazin-1-yl)phenol was collected via filtration. The purple solid was washed with heptanes before proceeding to the next step without further purification.

To a solution of 2-bromo-4-(piperazin-1-yl)phenol (500 mg, 1.95 mmol) and diisopropylethylamine (373 μL, 2.14 mmol) in DMF (6 mL) was added the tert-butyl (1H-pyrazol-1-yl)methanediylidenedicarbamate (664 mg, 2.14 mmol). After stirring at room temperature for 45 min. the reaction mixture was diluted with water (20 mL) and extracted with EtOAc (3×50 mL). The organic layers were separated and washed with brine, dried over $Na_2SO_4$, and concentrated to yield a crude oil. Purification of the crude material using silica gel chromatography (gradient of 0% to 100% EtOAc in hexanes) afforded tert-butyl (4-(3-bromo-4-hydroxyphenyl)piperazin-1-yl)methanediylidenedicarbamate was obtained as a white foam (171 mg, 40% yield). $^1$H NMR (300 MHz, DMSO-d6): δ 9.64, (br s, 1H), 9.60 (s, 1H), 7.05 (br s, 1H), 6.84 (br s, 2H), 3.49 (dd, 4H, J=5.0, 4.4 Hz), 2.99 (dd, 4H, J=4.5, 4.3 Hz), 1.44-1.37 (m, 18H); $^{13}$C (75.5 MHz, DMSO-d6): δ 159.5, 151.2, 150.8, 147.7, 144.7, 120.8, 117.5, 116.6, 109.5, 80.1, 77.1, 49.3, 45.3, 27.9 (2C); Minor rotomeric population is also visible; HRMS calcd for $C_{21}H_{31}BrN_4O_5$: 499.15506 found 499.15446.

Synthesis of tert-butyl (4-(3-bromo-4-(2-fluoroethoxy)phenyl)piperazin-1-yl)methanediylidenedicarbamate

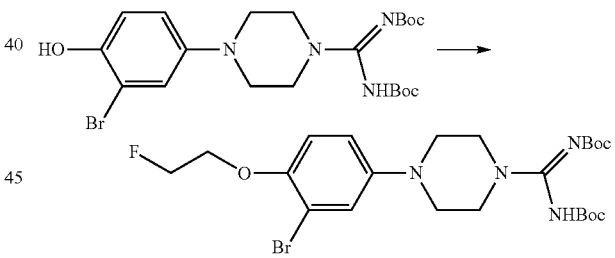

To a solution of tert-butyl (4-(3-bromo-4-hydroxyphenyl)piperazin-1-yl)methanediylidenedicarbamate (110 mg, 0.22 mmol) in DMSO (2.2 mL) was added potassium carbonate (46 mg, 0.33 mmol), potassium iodide (2 mg, 0.01 mmol), and 1-bromo-2-fluoroethane (18 μL, 0.24 mmol). After completion of the additions the reaction mixture stirred at 50° C. After 6 h the reaction mixture was cooled to room temperature and quenched with water (5 mL). The aqueous layer was extracted with EtOAc (4×20 mL) and all combined organic layers were washed with water (50 mL), brine (50 mL), dried over $Na_2SO_4$, and concentrated to yield a crude oil.

Purification of the crude material via HPLC using a Phenomenex Luna C-18 (2) column (10μ, 250×21.2 mm, gradient method 40-80% B over 20 min., where B=90% ACN in water using 0.1% formic acid as a modifier and A=water using 0.1% formic acid as a modifier) with a flow rate of 20 mL/min afforded tert-butyl (4-(3-bromo-4-(2- fluoroethoxy)phenyl)piperazin-1-yl)methanediylidenedicarbamate as a white solid (19 mg, 15% yield). $^1$H NMR (300 MHz, DMSO-d6): δ 9.56 (s, 1H), 7.05 (d, 1H, J=2.5 Hz), 6.91-6.82 (m, 2H), 4.83 (m, 1H), 4.67 (m, 1H), 4.26 (m, 1H), 4.17 (m, 1H), 3.79 (dd, 4H, J=4.7, 4.6 Hz), 3.08 (dd, 4H, J=4.5, 4.6 Hz), 1.49 (s, 18H); $^{19}$F NMR (282.4 MHz, DMSO-d6): δ −222.03 (m, 1F); $^{13}$C NMR (150 MHz, CDCl$_3$): δ 152.6, 150.9, 150.2, 145.6, 122.9, 117.6, 115.8, 113.8, 85.0, 82.5 (81.3), 69.6 (69.4), 50.3, 49.3, 27.8; HRMS calcd for $C_{23}H_{34}BrFN_4O_5$: 501.22745 found 501.2272.

Synthesis of 4-(3-bromo-4-(2-fluoroethoxy)phenyl)piperazine-1-carboximidamide

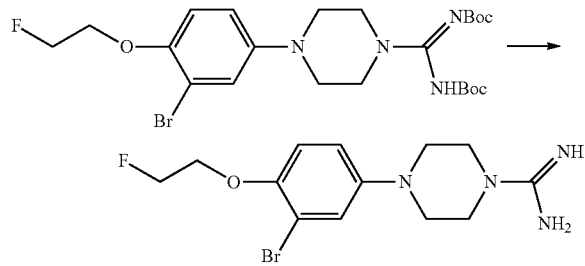

Tert-butyl (4-(3-bromo-4-(2-fluoroethoxy)phenyl)piperazin-1-yl)methanediylidenedicarbamate (26 mg, 0.044 mmol) was dissolved in a 4.0M solution of HCl in dioxane (0.6 mL) and stirred at room temperature overnight. The next day the reaction mixture was concentrated and purified via HPLC using a Phenomenex Luna C-18 (2) column (10μ, 250×21.2 mm, gradient method 40-80% B over 20 min., where B=90% ACN in water using 0.1% formic acid as a modifier and A=water using 0.1% formic acid as a modifier) with a flow rate of 20 mL/min afforded 4-(3-bromo-4-(2-fluoroethoxy)phenyl)piperazine-1-carboximidamide as a white solid (7.4 mg, 44% yield). $^1$H NMR (300 MHz, DMSO-d6): δ 8.45 (br s, 3H), 7.22 (d, 1H, J=2.8 Hz), 7.00 (m, 2H), 4.80 (m, 1H), 4.64 (m, 1H), 4.28 (m, 1H), 4.18 (m, 1H), 3.52 (dd, 4H, J=5.4, 4.6 Hz), 3.12 (dd, 4H, J=5.3, 4.9 Hz); $^{19}$F NMR (282.4 MHz, DMSO-d6): δ −222.03 (m, 1F); $^{13}$C NMR (75.5 MHz, DMSO-d6): δ 156.7, 148.2, 145.9, 120.8, 116.5, 115.2, 111.9, 82.7 (81.6), 68.9 (68.8), 48.3, 44.4; HRMS calcd for $C_{13}H_{18}BrFN_4O$: 301.12259 found 301.1225.

Example 21

Synthesis of 4-(4-((2-fluoroethoxy)methyl)phenyl)piperazine-1-carboximidamide

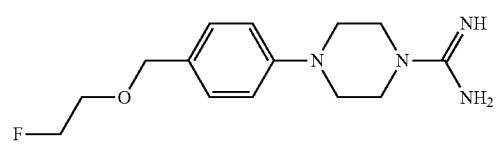 [SMILES: N=C(N)N1CCN(c2ccc(COCCF)cc2)CC1]

Synthesis of tert-butyl 4-(4-(hydroxymethyl)phenyl)piperazine-1-carboxylate

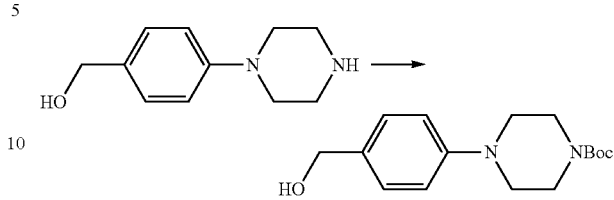

To a cooled (0° C.) solution of tert-butyl 4-(4-formylphenyl)piperazine-1-carboxylate (1.0 g, 3.44 mmol) in ether (17 mL) and THF (3 mL) was added solid lithium borohydride (38 mg, 1.72 mmol) in one portion. The reaction mixture stirred for 1 h at 0° C. before being quenched with 1N HCl to reach pH=7. The resulting organic layer was filtered through a pad of celite and concentrated to obtain tert-butyl 4-(4-(hydroxymethyl)phenyl)piperazine-1-carboxylate as an orange solid (1 g) $^1$H NMR (300 MHz, CDCl$_3$): δ 7.30 (d, 2H, J=8.6 Hz), 6.93 (d, 2H, J=8.6 Hz), 4.61 (d, 2H, J=5.0 Hz), 3.59 (dd, 4H, J=5.3, 5.1 Hz), 3.14 (dd, 4H, J=5.2, 5.0 Hz), 1.49 (m, 9H); $^{13}$C NMR (150 MHz, CDCl$_3$): δ 154.94, 151.11, 132.92, 128.59, 116.84, 80.14, 65.24, 49.66, 43.48, 28.64; Minor rotomeric populations are also visible; HRMS calcd for $C_{16}H_{24}N_2O_3$: 293.185969 found 293.18590.

Synthesis of tert-butyl 4-(4-((2-fluoroethoxy)methyl)phenyl)piperazine-1carboxylate

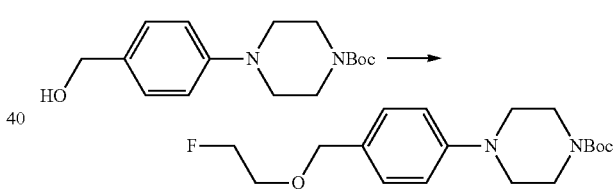

To a solution of tert-butyl 4-(4-(hydroxymethyl)phenyl)piperazine-1-carboxylate (100 mg, 0.34 mmol) in THF (1 mL) was added triphenylphosphine (135 mg, 0.51 mmol), 2-fluoroethanol (24 μL, 0.41 mmol) and diisopropylazodicarboxylate (99 μL, 0.51 mmol). The reaction mixture stirred at room temperature overnight. The next day the reaction mixture was diluted with water (5 mL) and extracted with EtOAc (2×10 mL). The combined organic layers were washed with water (20 mL) and brine (20 mL), dried over Na2SO4, and concentrated to obtain a crude oil. Purification of the crude material using silica gel chromatography (gradient of 0% to 100% EtOAc in hexanes) afforded tert-butyl 4-(4-((2-fluoroethoxy)methyl)phenyl)piperazine-1carboxylate as a colorless oil (26 mg, 22% yield). $^1$H NMR (300 MHz, CDCl$_3$) δ 7.27 (d, 2H, J=9.0 Hz), 6.89 (d, 2H, J=9.0 Hz), 4.65 (m, 1H), 4.52 (s, 2H), 4.49 (m, 1H), 3.74 (m, 1H), 3.64 (m, 1H), 3.58 (dd, 4H, J=6.0, 3.0 Hz), 3.13 (dd, 4H, J=6.0, 3.0 Hz), 1.49 (s, 9H); $^{19}$F NMR (282.4 MHz, CDCl$_3$): δ −223.01 (m, 1F); $^{13}$C NMR (75.5 MHz, CDCl$_3$); δ 154.7, 150.9, 129.4, 129.2, 116.5, 84.3 (82.0), 79.9, 73.0, 68.8 (68.7), 49.3, 44.0, 28.4; HRMS calcd for $C_{18}H_{27}FN_2O_5$: 339.20785 found 339.20790.

Synthesis of 1-(4-((2-fluoroethoxy)methyl)-phenyl)piperazine hydrochloride

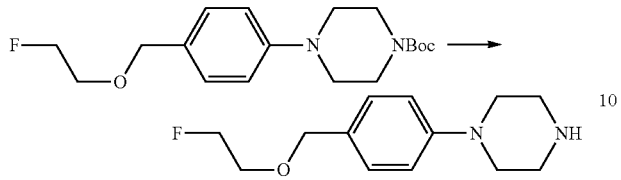

Tert-butyl 4-(4-((2-fluoroethoxy)methyl)phenyl)piperazine-1-carboxylate (100 mg, 0.29 mmol) was dissolved in a 4.0M solution of HCl in dioxane (1 mL) and stirred at room temperature. After 1 h, 1-(4-((2-fluoroethoxy)methyl)-phenyl)piperazine hydrochloride was collected as a white solid via filtration (74 mg, 91% yield). $^1$H NMR (300 MHz, DMSO-d6): δ 10.45 (br s, 1H), 9.71 (br s, 1H), 7.26 (d, 2H, J=8.7 Hz), 7.05 (d, 2H, J=8.7 Hz), 4.61 (m, 1H), 4.45 (m, 1H), 4.43 (s, 2H), 3.67 (m, 1H), 3.57 (m, 1H), 3.45 (dd, 4H, J=5.5, 4.9 Hz), 3.22 (m, 4H); $^{19}$F NMR (282.4 MHz, CDCl$_3$): δ −221.40 (m, 1F); $^{13}$C NMR (75.5 MHz, DMSO): δ 148.5, 130.7, 128.9, 116.4, 84.0 (82.0), 71.7, 68.7 (68.6), 46.0, 42.2; HRMS calcd for $C_{13}H_{19}FN_2O$: 239.15542 found 239.15540.

Synthesis of 4-(4-((2-fluoroethoxy)methyl)phenyl)piperazine-1-carboximidamide

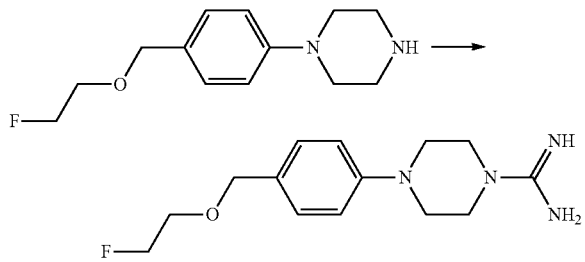

To a solution of 1-(4-((2-fluoroethoxy)methyl)-phenyl)piperazine hydrochloride (50 mg, 0.12 mmol) and diisopropylethylamine (67 µL, 0.38 mmol) in DMF (1 mL) was added 1H-pyrazole-1-carboximidamide hydrochloride (29 mg, 0.20 mmol). The reaction stirred at room temperature for 24 h. The next day, the reaction mixture was concentrated to yield a crude oil, which was purified via HPLC using a Phenomenex Luna C-18 (2) column (10µ, 250×21.2 mm, gradient method 15-55% B over 20 min., where B=90% ACN in water using 0.1% formic acid as a modifier and A=water using 0.1% formic acid as a modifier) with a flow rate of 20 mL/min afforded 4-(4-((2-fluoroethoxy) methyl)phenyl)piperazine-1-carboximidamide as a white solid (20 mg, 41% yield based on recovered starting material). $^1$H NMR (300 MHz, DMSO-d6): δ 7.58 (br s, 4H), 7.211 (d, 2H, J=8.5 Hz), 6.96 (d, 2H, J=8.6 Hz), 4.61 (m, 1H), 4.45 (m, 1H), 4.41 (s, 2H), 3.67 (m, 1H), 3.58 (dd, 4H, J=4.2, 3.9 Hz), 3.22 (m, 5H); $^{19}$F NMR (282.4 MHz, DMSO-d6): δ −221.39 (m, 1F); $^{13}$C NMR (75.5 MHz, DMSO-d6): δ 156.1, 149.8, 128.9, 115.4, 84.1 (81.9), 71.8, 68.6 (68.4), 47.5, 44.7; HRMS calcd for $C_{14}H_{21}FN_4O$: 281.177216 found 281.17720.

Example 22

Synthesis of 4-(4-(3-fluoropropyl)phenyl)piperazine-1-carboximidamide

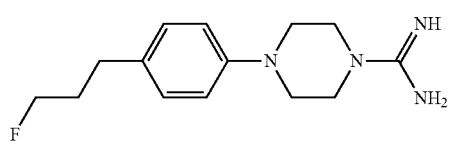 [SMILES: N=C(N)N1CCN(c2ccc(CCCF)cc2)CC1]

Synthesis of tert-butyl 4-(4-iodophenyl)piperazine-1-carboxylate

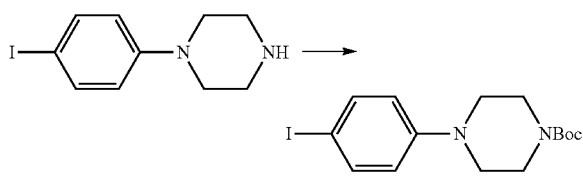

To a solution of 4-iodophenylpiperazine hydrochloride (1.0 g, 3.08 mmol) in water (15 mL) was added sodium hydroxide (246 mg, 6.16 mmol), followed by di-tert-butyl dicarbonate (740 mg, 3.39 mmol). The reaction mixture stirred at room temperature overnight. The next day, the reaction mixture was filtered to collect tert-butyl 4-(4-iodophenyl)piperazine-1-carboxylate as a tan solid (1.1 g, 92% yield), which was washed with water (50 mL) and taken on to the next step without further purification. $^1$H NMR (600 MHz, CDCl$_3$): δ 7.53 (d, 2H, J=9.0 Hz), 6.68 (d, 2H, J=9.0 Hz), 3.57 (dd, 4H, J=5.2, 5.0 Hz), 3.11 (dd, 4H, J=4.9, 4.9 Hz), 1.49 (s, 9H); $^{13}$C NMR (150 MHz, CDCl$_3$): δ 154.9, 151.1, 138.1, 118.8, 82.3, 80.2, 67.3, 49.2, 28.7; HRMS calcd for $C_{15}H_{21}IN_2O_5$: 389.07205 found 389.07165.

Synthesis of tert-butyl 4-(4-(3-hydroxyprop-1-ynyl) phenyl)piperazine-1-carboxylate

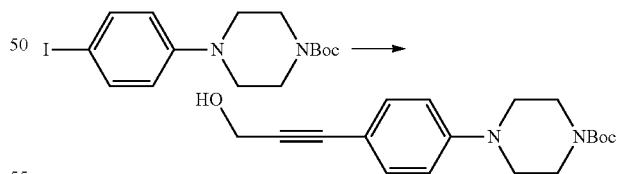

To a slurry of tert-butyl 4-(4-iodophenyl)piperazine-1-carboxylate (200 mg, 0.515 mmol), triphenylphosphine (1.4 mg, 0.005 mmol), and palladium chloride (0.5 mg, 0.003 mmol) in DEA (2 mL) was added DMF (400 µL) and copper iodide (1 mg, 0.005 mmol). The reaction mixture stirred at room temperature for 24 h. The next day, the reaction mixture was concentrated and purified using silica gel chromatography (gradient method 0%-100% EtOAc in hexanes) to afford tert-butyl 4-(4-(3-hydroxyprop-1-ynyl) phenyl)piperazine-1-carboxylate as a yellow solid (92 mg, 75% yield based on recovered starting material). $^1$H NMR (300 MHz, CDCl$_3$): δ 7.34 (d, 2H, J=8.8 Hz), 6.82 (d, 2H, J=8.9 Hz), 4.48 (d, 2H, J=5.6 Hz), 3.57 (dd, 4H, J=5.5, 4.9 Hz), 3.18 (dd, 4H, J=5.4, 5.0 Hz), 1.87 (t, 1H, J=5.7 Hz), 1.49 (s, 9H); $^{13}$C NMR (75 MHz, CDCl$_3$): δ 154.7, 150.9, 132.8, 115.5, 113.1, 85.9, 80.0, 51.7, 48.4, 44.8, 28.4; HRMS calcd for C$_{18}$H$_{24}$N$_2$O$_3$: 317.18597 found 317.1861.

Synthesis of tert-butyl 4-(4-(3-hydroxypropyl)phenyl)piperazine-1-carboxylate

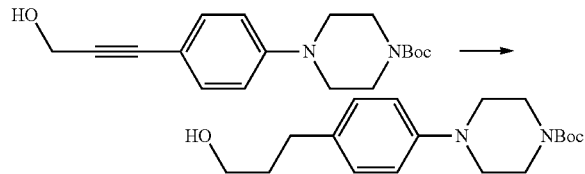

To a solution of tert-butyl 4-(4-(3-hydroxyprop-1-ynyl)phenyl)piperazine-1-carboxylate (3.2 g, 10.11 mmol) in EtOH (253 mL) was added EtOAc (200) and Pd/C (10% mol on carbon, 3.2 g). The reaction mixture was shaken at 50 psi of H$_2$ atm. overnight. The next day, the catalyst was removed from the reaction mixture via a filtration over a pad of celite and the filtrate was concentrated to yield a crude oil. Purification of the crude material using silica gel chromatography (gradient method of 0%-100% EtOAc in hexanes) yielded tert-butyl 4-(4-(3-hydroxypropyl)phenyl)piperazine-1-carboxylate as an off-white solid (2.3 g, 71% yield). $^1$H NMR (300 MHz, CDCl$_3$): δ 7.11 (d, 2H, J=8.7 Hz), 6.89 (d, 2H, J=8.7 Hz), 3.67 (br t, 2H, J=6.4 Hz), 3.58 (dd, 4H, J=5.2, 5.1 Hz), 3.09 (dd, 4H, J=5.2, 5.0 Hz), 2.65 (dd, 2H, J=8.0, 7.4 Hz), 1.87 (m, 2H), 1.49 (s, 9H); $^{13}$C NMR (150 MHz, CDCl$_3$): δ 154.9, 149.7, 133.9, 129.3, 117.1, 80.1, 62.4, 49.9, 44.1, 34.5, 31.3, 28.6; HRMS calcd for C$_{18}$H$_{28}$N$_2$O$_3$: 321.21727 found 321.2174.

Synthesis of tert-butyl 4-(4-(3-fluoropropyl)phenyl)piperazine-1-carboxylate

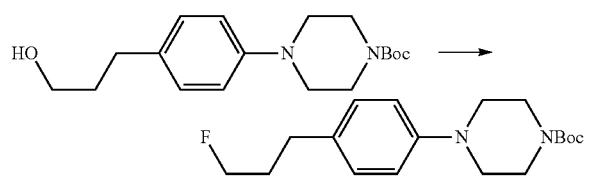

To a solution of deoxofluor (152 μL, 0.69 mmol) in DCM (1.0 mL) at −78° C. was added tert-butyl 4-(4-(3-hydroxypropyl)phenyl)piperazine-1-carboxylate (200 mg, 0.625 mmol) dissolved in DCM (1.0 mL). After stirring at 0° C. for 1 h the reaction mixture was quenched with saturated NaHCO$_3$, and extracted with DCM (2×5 mL). All combined organic layers were washed with water (10 mL) and brine (10 mL), dried over Na$_2$SO$_4$, filtered, and concentrated to obtain a crude oil. The crude material was purified using silica gel chromatography (0%-100% gradient of EtOAc in Hexanes) to obtain tert-butyl 4-(4-(3-fluoropropyl)phenyl)piperazine-1-carboxylate (78 mg, 46% yield was on recovered starting material). $^1$H NMR (300 MHz, CDCl$_3$): δ 7.12 (d, 2H, J=8.7 Hz), 6.89 (d, 2H, J=8.6 Hz), 4.53 (t, 1H, J=6.0 Hz), 4.38 (t, 1H, J=6.0 Hz), 3.59 (dd, 4H, J=5.3, 5.1 Hz), 3.10 (dd, 4H, J=5.2, 5.0 Hz), 2.68 (dd, 2H, J=8.1, 7.2 Hz), 2.07-1.90 (m, 2H), 1.49 (s, 9H); $^{19}$F NMR (282 MHz, CDCl$_3$): δ −220.02 (m, 1F); $^{13}$C NMR (75 MHz, CDCl$_3$): δ 154.9, 149.8, 133.2, 129.4, 117.1, 84.5 (82.3), 80.1, 49.9, 43.9, 32.5 (32.2), 30.6 (30.5), 28.65; HRMS calcd for C$_{18}$H$_{27}$FN$_2$O$_2$: 323.212933 found 323.21320.

Synthesis of 1-(4-(3-fluoropropyl)phenyl)piperazine

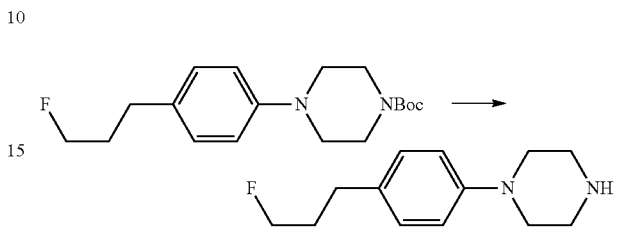

Tert-butyl 4-(4-(3-fluoropropyl)phenyl)piperazine-1-carboxylate (78 mg, 0.24 mmol) was dissolved in a 4.0M solution of HCl in dioxane (3 mL) and stirred at room temperature. After 1 h 1-(4-(3-fluoropropyl)phenyl)piperazine hydrochloride was collected as a white solid via filtration (63 mg). $^1$H NMR (300 MHz, CDCl$_3$): δ 9.58 (br s, 2H), 9.38 (br s, 1H), 7.15 (d, 2H, J=8.7 Hz), 7.00 (d, 2H, J=8.6 Hz), 4.49 (t, 1H, J=6.0 Hz), 4.34 (t, 1H, J=6.0 Hz), 3.40 (dd, 4H, J=5.5, 4.7 Hz), 3.22 (br s, 4H), 2.59 (dd, 2H, J=8.1, 6.3 Hz), 1.98-1.80 (m, 2H); $^{19}$F NMR (282.4 MHz, CDCl$_3$): δ −217.98 (m, 1F); $^{13}$C NMR (75.5 MHz, CDCl$_3$): δ 147.3, 133.6, 128.9, 116.71, 83.6 (82.5), 46.2, 42.2, 31.5 (31.4), 29.7 (29.6); HRMS calcd for C$_{13}$H$_{19}$FN$_2$:223.160503 found 223.16060.

Synthesis of 4-(4-(3-fluoropropyl)phenyl)piperazine-1-carboximidamide

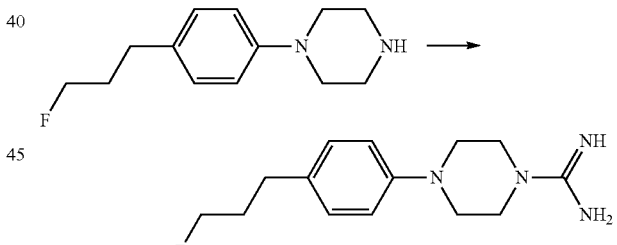

To a solution of 1-(4-(3-fluoropropyl)phenyl)piperazine hydrochloride (50 mg, 0.22 mmol) and diisopropylethylamine (82 μL, 0.47 mmol) in DMF (1 mL) was added 1H-pyrazole-1-carboximidamide hydrochloride (36 mg, 0.25 mmol). After stirring at room temperature for 9 h, the reaction mixture was purified via HPLC using a Phenomenex Luna C-18 (2) column (10μ, 250×21.2 mm, gradient method 15-55% B over 40 min., where B=90% ACN in water using 0.1% TFA as a modifier and A=water using 0.1% TFA as a modifier) with a flow rate of 20 mL/min afforded 4-(4-(3-fluoropropyl)phenyl)piperazine-1-carboximidamide as a white solid (36 mg, 42% yield). $^1$H NMR (300 MHz, DMSO-d6): δ 7.53 (br s, 3H), 7.09 (d, 2H, J=8.6 Hz), 6.92 (d, 2H, J=8.6 Hz), 4.50 (t, 1H, J=6.0 Hz), 4.34 (t, 1H, J=6.0 Hz), 3.57 (dd, 4H, J=5.3, 4.8 Hz), 3.17 (dd, 4H, J=5.2, 4.9 Hz), 2.58 (dd, 2H, J=8.1, 6.4 Hz), 1.98-1.80 (m, 2H); $^{19}$F NMR (282.4 MHz, DMSO-d6): δ −217.97 (m, 1F); $^{13}$C NMR (150 MHz, DMSO-d6): δ 156.1, 148.5, 132.1, 128.8, 116.2, 83.6 (82.5), 47.8, 44.8, 31.7 (31.6), 29.7 (29.6); HRMS calcd. for $C_{14}H_{21}FN_4$: 265.18230 found 265.18240.

Examples 23 and 24

Synthesis of N-[3-bromo-4-(3-fluoro-propoxy)-benzyl]-guanidine hydrochloride and N-[3-bromo-4-(3-[18F]fluoropropoxy)-benzyl]-guanidine hydrochloride Part A—Synthesis of 3-bromo-4-(tert-butyl-dimethyl-silanyloxy)-benzaldehyde

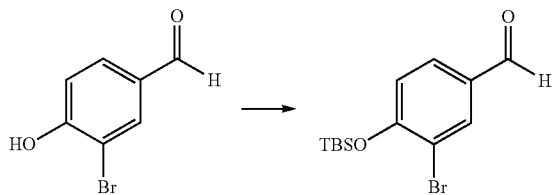 [SMILES: O=Cc1ccc(O)c(Br)c1 ; CC(C)(C)[Si](C)(C)Oc1ccc(C=O)cc1Br]

To a solution of 3-bromo-4-hydroxy-benzaldehyde (7.14 g, 35.52 mmol) dissolved in DMF (35.5 mL) was added imidazole (5.80 g, 85.24 mmol) and TBDMS-Cl (6.42 g, 42.62 mmol). The reaction mixture stirred for 4 h and was then diluted with water (50 mL). The aqueous layer was extracted with EtOAc (3×50 mL). The organic layer was dried over $Na_2SO_4$ and concentrated to yield a crude oil. Purification using silica gel chromatography afforded 3-bromo-4-(tert-butyl-dimethyl-silanyloxy)-benzaldehyde as a yellow oil (5.13 g, 46% yield). $^1$H NMR (CDCl$_3$, 300 MHz): δ 9.83 (s, 1H), 8.06 (d, J=3.0 Hz, 1H), 7.71 (dd, J=3.0, 9.0 Hz, 1H), 6.97 (d, J=9.0 Hz, 1H), 1.17 (s, 9H), 0.28 (s, 6H); $^{13}$C NMR (CDCl$_3$, 75 MHz): δ 189.8, 158.3, 135.5, 131.5, 130.5, 120.2, 116.6, 25.8, 18.6, −4.0.

Part B—Synthesis of [3-bromo-4-(tert-butyl-dimethyl-silanyloxy)-phenyl]-methanol

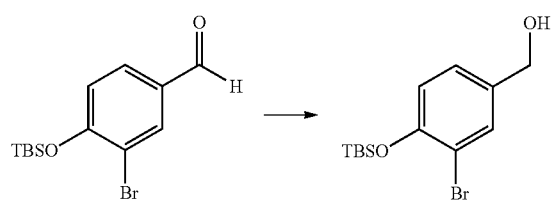 [SMILES: CC(C)(C)[Si](C)(C)Oc1ccc(C=O)cc1Br ; CC(C)(C)[Si](C)(C)Oc1ccc(CO)cc1Br]

To a cooled (0° C.) solution of 3-bromo-4-(tert-butyl-dimethyl-silanyloxy)-benzaldehyde (5.13 g, 16.33 mmol) dissolved in MeOH (16.5 mL) was added $Na_2BH_4$ (0.309 g, 8.17 mmol) portion-wise. Once all the reducing agent was added the reaction mixture stirred at room temperature for 30 minutes before being quenched with water (15 mL). MeOH was removed en vacuo and DCM (20 mL) was added to the remaining crude reaction mixture. The aqueous layer was extracted with DCM (3×20 mL). Combined organics were dried over $Mg_2SO_4$ and concentrated to yield a crude oil. Purification using silica gel chromatography afforded [3-bromo-4-(tert-butyl-dimethyl-silanyloxy)-phenyl]-methanol as a colorless oil (4.22 g, 82% yield). $^1$H NMR (CDCl$_3$, 300 MHz): δ 7.55 (m, 1H), 7.17 (dd, J=3.0, 9.0 Hz, 1H), 6.86 (d, J=9.0 Hz, 1H), 4.61 (s, 2H), 1.05 (s, 9H), 0.26 (s, 6H); $^{13}$C NMR (CDCl$_3$, 75 MHz): δ 152.4, 135.3, 132.5, 127.3, 120.5, 115.6, 64.6, 26.0, 18.6, −4.0.

Part C—Synthesis of 1,3-bis(tert-butoxy-carbonyl)-[3-bromo-4-(tert-butyl-dimethyl-silanyloxy)-benzyl]-guanidine

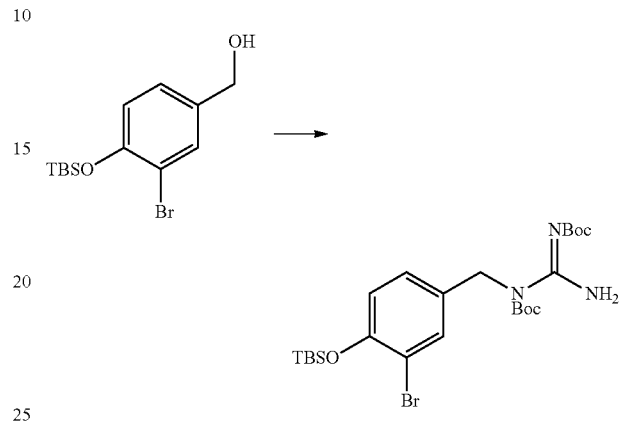

To a solution of [3-bromo-4-(tert-butyl-dimethyl-silanyloxy)-phenyl]-methanol (3.11 g, 9.84 mmol) dissolved in THF (98.4 mL) was added PPh$_3$ (3.87 g, 14.76 mmol), 1,3 bis(tert-butoxy-carbonyl)guanidine (3.83 g, 11.81), and DIAD (2.86 mL, 14.76 mmol). The reaction mixture stirred at room temperature for 30 minutes before being concentrated en vacuo. The resulting yellow oil was purified using silica gel chromatography (4:1 hexanes: EtOAc) to afford 1,3-bis(tert-butoxy-carbonyl)-[3-bromo-4-(tert-butyl-dimethyl-silanyloxy)-benzyl]-guanidine (5.14 g, 94% yield). $^1H$ NMR (CDCl$_3$, 300 MHz): δ 9.48 (br s, 2H), 7.48 (m, 1H), 7.12 (dd, J=3.0, 9.0 Hz, 1H), 6.80 (d, J=9.0 Hz, 1H), 5.07 (s, 2H), 1.55 (s, 9H)$^1$1.34 (s, 9H), 1.03 (s, 9H), 0.24 (s, 6H); $^{13}$C NMR (CDCl$_3$, 75 MHz): δ 155.0, 151.8, 133.3, 133.0, 127.7, 120.2, 115.0, 84.6, 46.8, 28.5, 28.1, 26.0, 18.6, −4.0.

Part D—Synthesis of 1,3-bis(tert-butoxy-carbonyl)-[3-bromo-4-hydroxy-benzyl]-guanidine

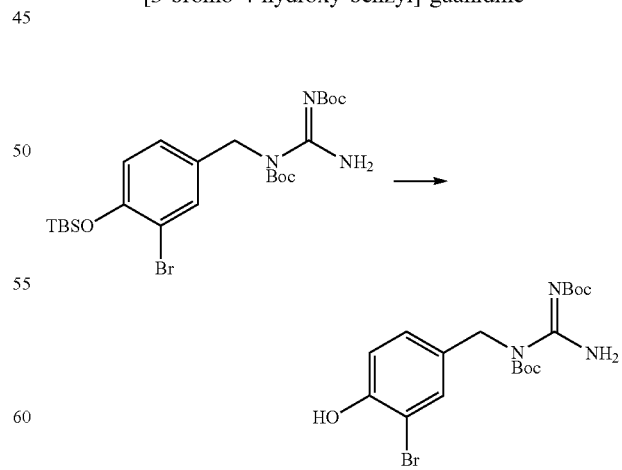

To a solution of AA (5.14 g, 9.22 mmol) dissolved in THF (92.2 mL) was added a solution of TBAF (18.56 mL of 1M THF solution, 18.46 mmol) drop-wise. After completion of addition the reaction mixture continued to stir at room temperature for 20 minutes. The reaction mixture was concentrated en vacuo to yield a crude oil, which was purified using silica gel chromatography (4:1 hexanes:EtOAc) to afford a white solid (3.52 g, 88% yield). ¹H NMR (CDCl₃, 300 MHz): δ 9.48 (br s, 2H), 7.45 (m, 1H), 7.15 (dd, J=3.0, 9.0 Hz, 1H), 6.92 (d, J=9.0 Hz, 1H), 5.08 (s, 2H), 1.52 (s, 9H) 1.42 (s, 9H).

Part E—Synthesis of 1,3-bis(tert-butoxy-carbonyl-[3-bromo-4-(3-fluoro-propoxy)-benzyl]-guanidine

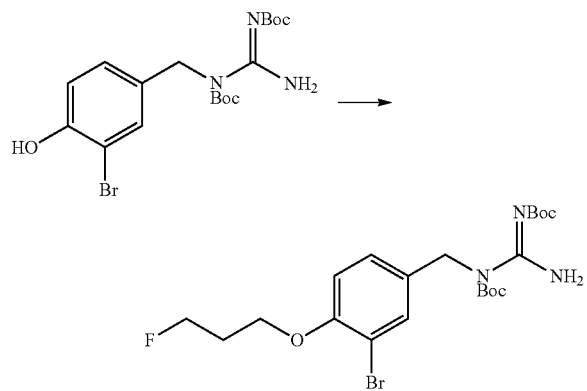

To a solution of phenol (300 mg, 0.677 mmol) dissolved in DMF (7 mL) was added 1-bromo-3-fluoro propane (123.16 mg, 0.880 mmol) and K₂CO₃ (140.3 mg, 1.02 mmol). The reaction mixture was heated to 50 C for 2.5 h before being quenched with water (10 mL). The aqueous layer was extracted with EtOAc (20 mL). Organic layer was dried over Na₂SO₄, filtered, and concentrated to yield a yellow oil. Purification of the crude material using silica gel chromatography afforded 1,3-bis(tert-butoxy-carbonyl-[3-bromo-4-(3-fluoro-propoxy)-benzyl]-guanidine (208.5 mg, 61% yield). ¹H NMR (CDCl₃, 600 MHz): δ 9.43 (br s, 2H), 7.54 (m, 1H), 7.54 (d, J=7.8 Hz, 1H), 6.84 (d, J=8.4 Hz, 1H), 5.09 (s, 2H), 4.74 (m, 1H), 4.67 (m, 1H), 4.14 (m, 1H), 2.26-2.18 (m, 2H), 1.51 (s, 9H) 1.42 (s, 9H); ¹³C NMR (CDCl₃, 150 MHz): δ 155.0, 154.4, 133.2, 128.1, 113.2, 111.9, 81.4 (80.3), 65.0 (64.9), 46.8, 30.7 (30.5), 28.5, 28.0; ¹⁹F NMR (CDCl₃, 282 MHz): δ −222.68 (m, 1F).

Part F—Example 23—Synthesis of N-[3-bromo-4-(3-fluoro-propoxy)-benzyl]-guanidine hydrochloride

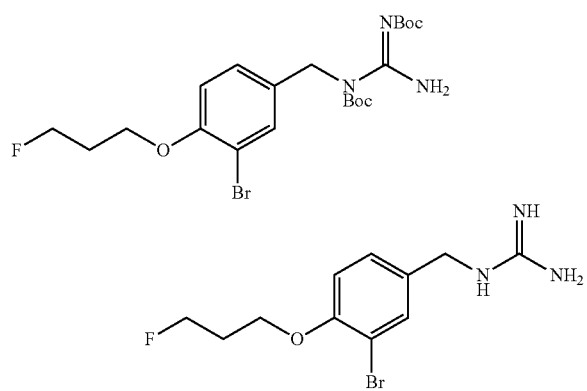

A solution of 1,3-bis(tert-butoxy-carbonyl-[3-bromo-4-(3-fluoro-propoxy)-benzyl]-guanidine (250.6 mg, 50 mmol) in 4N HCl in dioxane (6 mL) was heated to 50° C. for 2 h. The reaction mixture was diluted with water (4 mL) and ACN (1 mL) and lyophilized to afford N-[3-bromo-4-(3-fluoro-propoxy)-benzyl]-guanidine hydrochloride as a white solid (169.1 mg, 99% yield). ¹H NMR (DMSO-d6, 600 MHz): δ 8.03 (br t, 1H), 7.55 (m, 1H), 7.31-7.27 (m, 2H), 7.15 (d, J=9 Hz, 1H), 4.72 (t, J=6 Hz, 1H), 4.56 (t, J=6 Hz, 1H), 4.30 (m, 2H), 4.15 (t, J=6 Hz, 2H), 2.19-2.06 (m, 2H).

Part G—Example 24—Synthesis of N-[3-bromo-4-(3-[18F]fluoropropoxy)-benzyl]-guanidine hydrochloride

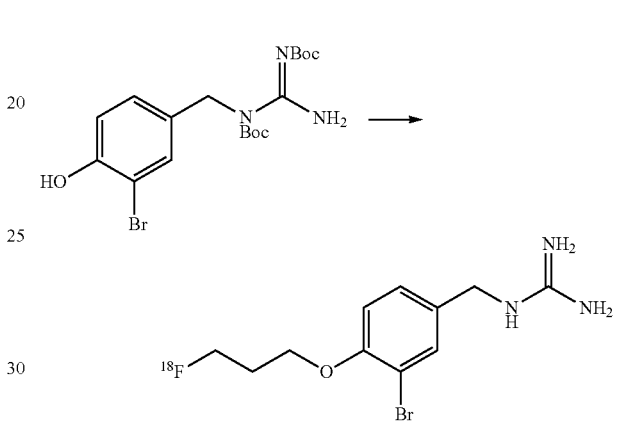

To a solution of phenol (3 mg, 6.77 umol) dissolved in acetonitrile (0.7 mL) was added 3-[18F]fluoropropyl toluenesulfonate (350 uCi) and K₂CO₃ (1.40 mg). The reaction mixture was heated to 80° C. for 45 minutes and cooled to room temperature. The solvent was evaporated in a stream of warm nitrogen under partial vacuum. 4N HCl in dioxane (1.0 mL) was added and the resultant mixture was heated to 50° C. for 15 minutes. The reaction mixture was diluted with water (15 mL) deposited onto a reverse-phase (C-18) cartridge. The salts were removed by washing the column with distilled water, and the compound was eluted with pure acetonitrile (2.0 mL). An aliquot was purified via reversed phase HPLC to afford a ca. 10 mCi sample of pure N-[3-bromo-4-(3-[18F]fluoropropoxy)-benzyl]-guanidine hydrochloride.

Example 25—Animal Preparation

Male Sprague Dawley rats (300-500 g, Taconic), male New Zealand rabbits (3-4 kg, Covance) and male non-human primates (NHP, Cynomolgus monkeys 2-4 kg) were used in this study in concordance with our Institutional Animal Care and Use Committee. In tissue biodistribution and imaging studies, rats were anesthetized with sodium pentobarbital (50 mg/kg, i.p.) and the left femoral vein was canulated with PE50 tubing for drug injection. Rabbits were pre-sedated with acepromazine (0.75 mg/kg i.m.) and then anesthetized with ketamine (40 mg/kg, i.m.) and xylazine (8 mg/kg, i.m). The ear marginal vein was canulated for drug injection. NHPs were anesthetized with acepromazine (0.3 mg/kg, i.m.) and ketamine (10 mg/kg, i.m.), orally intubated and maintained with isoflurane (0.4-1.5%). The saphenous vein in the legs was canulated for drug injection. Additional doses of anesthetics were given as needed.

Tissue Biodistribution in Rats and Rabbits

After anesthesia and vein canulation, each animal received a bolus injection of $^{18}$F labeled agent via the venous catheter. Rats and rabbits were euthanized after the injection and samples of the blood, heart, lung, liver, spleen, kidney, femur and muscle were collected. All samples were weighed and counted for radioactivity (Wallac Wizard 1480, PerkinElmer Life and Analytical Sciences, Shelton, Conn.). The net amount of activity administered in each animal was calculated by subtracting the residual activities in the syringe and venous catheter. The tissue uptake of each agent was determined as % injected dose per gram tissue (% ID/g).

Cardiac PET Imaging in Animals

Cardiac PET imaging was performed in anesthetized rats, rabbits and NHP. Each animal was anesthetized and a venous catheter was established for imaging agent injection. Then the animal was positioned in a microPET camera (Focus220, CTI Molecular Imaging, Inc. Knoxville, Tenn.) for cardiac imaging. Labeled agent was injected intravenously and animals imaged up to 120 minutes.

Image Reconstruction and Analysis

After the acquisition, images were reconstructed in a matrix of 256×256 pixels with 95 transverse slices using the filtered back projection algorithm and decay corrected (microPET Manager and ASIPro, CTI Molecular Imaging, Inc. Knoxville, Tenn.). The pixel size was 0.47 mm and the slice thickness was 0.80 mm. The images were reoriented regarding cardiac axis and serial tomographic cardiac image frames were then generated for every 10-minute period from 5 to 125 minutes.

Figure 2:
FIG. 2 is a second series of cardiac short- and long-axis images in a non-human primate according to a further embodiment of the invention.

FIGS. 1 and 2 represent the images derived from cardiac scanning according to the invention.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A compound having Structure Chi as follows:

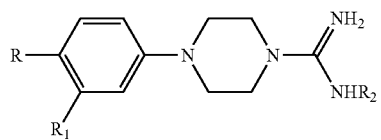

or a salt thereof;
wherein R selected from the group consisting of $OR_3$, $OCH_2CH_2F$, and $OCH_2CH_2Im$;
$R_1$ is selected from the group consisting of H, $OR_3$, F, Cl, Br, and I; and
$R_2$ is H;
$R_3$ is alkyl;
wherein said alkyl, of $R_3$ is substituted with one or more groups selected from halogen, Im, $COOR_4$, $CON(R_4)_2$, $SR_4$, $OR_4$, and $NHC(=O)NH_2$;
$R_4$ is alkyl; and
wherein Im is an imaging agent selected from the group consisting of $^{18}$F, $^{76}$Br, $^{124}$I, and $^{131}$I.

2. The compound of claim 1, wherein the alkyl group is substituted with a functional group selected from the group consisting of F, Cl, Br, I, Im, $COOR_4$, $CON(R_4)_2$, $SR_4$, $OR_4$ and $NHC(=O)NH2$.

3. The compound of claim 1, wherein Im is $^{18}$F.

4. A compound of the formula:

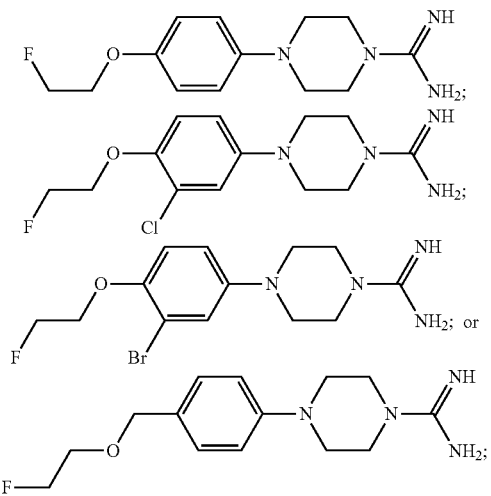

or a pharmaceutically acceptable salt thereof.

* * * * *